(12) United States Patent
Parekh et al.

(10) Patent No.: US 9,809,867 B2
(45) Date of Patent: Nov. 7, 2017

(54) CARBON PURIFICATION OF CONCENTRATED SUGAR STREAMS DERIVED FROM PRETREATED BIOMASS

(71) Applicant: SWEETWATER ENERGY, INC., Rochester, NY (US)

(72) Inventors: Sarad Parekh, Pittsford, NY (US); Carl P. Felice, Churchville, NY (US)

(73) Assignee: SWEETWATER ENERGY, INC., Rochester, NY (US)

( * ) Notice: Subject to any disclaimer, the term of this patent is extended or adjusted under 35 U.S.C. 154(b) by 0 days.

(21) Appl. No.: 14/776,411

(22) PCT Filed: Mar. 14, 2014

(86) PCT No.: PCT/US2014/027850
§ 371 (c)(1),
(2) Date: Sep. 14, 2015

(87) PCT Pub. No.: WO2014/143753
PCT Pub. Date: Sep. 18, 2014

(65) Prior Publication Data
US 2016/0032414 A1    Feb. 4, 2016

Related U.S. Application Data

(60) Provisional application No. 61/800,001, filed on Mar. 15, 2013.

(51) Int. Cl.
C13K 1/04 (2006.01)
C13K 13/00 (2006.01)
C12P 19/02 (2006.01)

(52) U.S. Cl.
CPC ............ *C13K 1/04* (2013.01); *C12P 19/02* (2013.01); *C13K 13/002* (2013.01); *C13K 13/007* (2013.01); *C12P 2203/00* (2013.01)

(58) Field of Classification Search
None
See application file for complete search history.

(56) References Cited

U.S. PATENT DOCUMENTS 1,447,461 A  *  3/1923  Brewster ............... C13B 20/123
                                                              127/55
1,867,750 A      7/1932  Naugle
(Continued)

FOREIGN PATENT DOCUMENTS

CA    1267407 B    4/1990
EP    0037912 A2   10/1981
(Continued)

OTHER PUBLICATIONS

Kamal et al, Detoxification of sago trunk hydrolysate using activated charcoal for xylitol production, 2011, Procedia Food Science, 1, pp. 908-913.*

(Continued)

*Primary Examiner* — Melvin C Mayes
*Assistant Examiner* — Stefanie Cohen
(74) *Attorney, Agent, or Firm* — Wilson Sonsini Goodrich & Rosati

(57) ABSTRACT

Provided are methods and compositions using activated carbon for optimizing purification and clarification of sugar streams produced from cellulosic or lignocellulosic biomass. Also provided are methods and compositions for decreasing one or more undesirable products during pretreatment.

18 Claims, 15 Drawing Sheets

Total Peak Area: 25,590,756 mV

(56) References Cited

U.S. PATENT DOCUMENTS

| | | | |
|---|---|---|---|
| 2,362,357 A * | 11/1944 | Cummins | C13B 20/005 127/46.1 |
| 2,388,222 A * | 10/1945 | Behrman | C13B 20/14 127/46.2 |
| 2,594,544 A | 4/1952 | Elving et al. | |
| 2,763,580 A * | 9/1956 | Zabor | C13B 20/123 127/55 |
| 3,563,799 A | 2/1971 | James et al. | |
| 3,730,770 A | 5/1973 | Zievers et al. | |
| 4,048,341 A | 9/1977 | Lagerstrom et al. | |
| 4,070,232 A | 1/1978 | Funk | |
| 4,182,780 A | 1/1980 | Lagerstrom et al. | |
| 4,186,658 A | 2/1980 | Brown | |
| 4,201,596 A | 5/1980 | Burroughs et al. | |
| 4,214,947 A | 7/1980 | Berger | |
| 4,237,226 A | 12/1980 | Grethlein | |
| 4,288,551 A | 9/1981 | Gudnason et al. | |
| 4,326,032 A | 4/1982 | Grove | |
| 4,350,766 A | 9/1982 | Mehlberg | |
| 4,395,488 A | 7/1983 | Rowe | |
| 4,414,330 A | 11/1983 | Zucker et al. | |
| 4,447,534 A | 5/1984 | Moebus et al. | |
| 4,478,644 A | 10/1984 | Berger et al. | |
| 4,478,854 A | 10/1984 | Adler-Nissen et al. | |
| 4,502,890 A | 3/1985 | Urbanic | |
| 4,520,105 A | 5/1985 | Sinner et al. | |
| 4,600,590 A | 7/1986 | Dale | |
| 4,612,286 A | 9/1986 | Sherman et al. | |
| 4,615,742 A | 10/1986 | Wright | |
| 4,632,795 A | 12/1986 | Huber et al. | |
| 4,644,060 A | 2/1987 | Chou | |
| 4,650,689 A | 3/1987 | Hedrick | |
| 4,728,367 A | 3/1988 | Huber et al. | |
| 4,806,475 A | 2/1989 | Gould | |
| 4,935,183 A | 6/1990 | Wenger et al. | |
| 5,037,663 A | 8/1991 | Dale | |
| 5,114,488 A | 5/1992 | Huber et al. | |
| 5,144,008 A | 9/1992 | Ikeda et al. | |
| 5,171,592 A | 12/1992 | Holtzapple et al. | |
| 5,177,008 A | 1/1993 | Kampen | |
| 5,177,009 A | 1/1993 | Kampen | |
| 5,338,366 A | 8/1994 | Grace et al. | |
| 5,378,491 A | 1/1995 | Stanley et al. | |
| 5,454,911 A | 10/1995 | Rafferty | |
| 5,473,061 A | 12/1995 | Bredereck et al. | |
| 5,693,296 A | 12/1997 | Holtzapple et al. | |
| 5,726,046 A | 3/1998 | Farone et al. | |
| 5,846,787 A | 12/1998 | Ladisch et al. | |
| 5,865,898 A | 2/1999 | Holtzapple et al. | |
| 5,916,780 A | 6/1999 | Foody et al. | |
| 5,939,544 A | 8/1999 | Karstens et al. | |
| 5,969,189 A | 10/1999 | Holtzapple et al. | |
| 5,986,133 A | 11/1999 | Holtzapple et al. | |
| 6,043,392 A | 3/2000 | Holtzapple et al. | |
| 6,106,888 A | 8/2000 | Dale et al. | |
| 6,176,176 B1 | 1/2001 | Dale et al. | |
| 6,258,175 B1 | 7/2001 | Lightner | |
| 6,262,313 B1 | 7/2001 | Holtzapple et al. | |
| 6,332,542 B2 | 12/2001 | Bilodeau et al. | |
| 6,355,456 B1 | 3/2002 | Hallberg et al. | |
| 6,365,732 B1 | 4/2002 | Van Thorre | |
| 6,409,841 B1 | 6/2002 | Lombard | |
| 6,416,621 B1 | 7/2002 | Karstens | |
| 6,475,552 B1 | 11/2002 | Shah et al. | |
| 6,478,965 B1 | 11/2002 | Holtzapple et al. | |
| 6,509,180 B1 | 1/2003 | Verser et al. | |
| 6,990,459 B2 | 1/2006 | Schneider | |
| 7,109,005 B2 | 9/2006 | Eroma et al. | |
| 7,198,925 B2 | 4/2007 | Foody | |
| 7,218,975 B2 | 5/2007 | Stevens et al. | |
| 7,503,981 B2 | 3/2009 | Wyman et al. | |
| 7,807,419 B2 | 10/2010 | Hennessey et al. | |
| 7,819,976 B2 | 10/2010 | Friend et al. | |
| 7,909,895 B2 | 3/2011 | Dickinson et al. | |
| 7,910,338 B2 | 3/2011 | Hennessey et al. | |
| 7,930,085 B2 | 4/2011 | Anderson et al. | |
| 7,932,063 B2 | 4/2011 | Dunson, Jr. et al. | |
| 7,932,065 B2 | 4/2011 | Medoff | |
| 7,935,840 B2 | 5/2011 | Leveson et al. | |
| 8,003,352 B2 | 8/2011 | Foody et al. | |
| 8,024,074 B2 | 9/2011 | Stelford et al. | |
| 8,086,354 B2 | 12/2011 | Bondar et al. | |
| 8,103,385 B2 | 1/2012 | Macharia et al. | |
| 8,110,383 B2 | 2/2012 | Joensson et al. | |
| 8,123,864 B2 | 2/2012 | Christensen et al. | |
| 8,168,840 B2 | 5/2012 | Brady et al. | |
| 8,318,453 B2 | 11/2012 | Medoff | |
| 8,323,923 B1 | 12/2012 | Horton | |
| 8,328,947 B2 | 12/2012 | Anand et al. | |
| 8,394,277 B2 | 3/2013 | Bonanni et al. | |
| 8,426,161 B1 | 4/2013 | Horton | |
| 8,445,236 B2 | 5/2013 | Hennessey et al. | |
| 8,529,765 B2 | 9/2013 | Horton | |
| 8,561,533 B2 | 10/2013 | Burke | |
| 8,563,277 B1 | 10/2013 | Parekh et al. | |
| 8,691,050 B2 | 4/2014 | Christensen | |
| 8,722,924 B1 | 5/2014 | Overheul et al. | |
| 8,765,430 B2 | 7/2014 | Parekh et al. | |
| 9,004,742 B2 | 4/2015 | Burke et al. | |
| 9,056,294 B2 | 6/2015 | Fink et al. | |
| 9,115,214 B2 | 8/2015 | Nguyen et al. | |
| 9,150,936 B2 | 10/2015 | Dottori et al. | |
| 9,499,635 B2 | 11/2016 | Chesonis et al. | |
| 2002/0038058 A1 | 3/2002 | Holtzapple et al. | |
| 2002/0153317 A1 | 10/2002 | Heikkila et al. | |
| 2002/0164730 A1 | 11/2002 | Ballesteros Perdices et al. | |
| 2002/0164731 A1 | 11/2002 | Eroma et al. | |
| 2002/0192774 A1 | 12/2002 | Ahring et al. | |
| 2002/0197686 A1 | 12/2002 | Lightner | |
| 2003/0109011 A1 | 6/2003 | Hood et al. | |
| 2003/0199049 A1 | 10/2003 | Nguyen et al. | |
| 2003/0221361 A1 | 12/2003 | Russell et al. | |
| 2003/0224088 A1 | 12/2003 | Burdick | |
| 2004/0152881 A1 | 8/2004 | Holtzapple et al. | |
| 2004/0168960 A1 | 9/2004 | Holtzapple et al. | |
| 2004/0171136 A1 | 9/2004 | Holtzapple et al. | |
| 2005/0054064 A1 | 3/2005 | Talluri et al. | |
| 2005/0203291 A1 | 9/2005 | Svenson et al. | |
| 2005/0244934 A1 | 11/2005 | Foody et al. | |
| 2005/0271770 A1 | 12/2005 | Hughes | |
| 2005/0272134 A1 | 12/2005 | Hughes | |
| 2006/0003064 A1 | 1/2006 | James | |
| 2006/0024801 A1 | 2/2006 | Holtzapple et al. | |
| 2006/0032113 A1 | 2/2006 | Whitney | |
| 2006/0069244 A1 | 3/2006 | Holtzapple et al. | |
| 2006/0090749 A1 | 5/2006 | Rein et al. | |
| 2006/0188980 A1 | 8/2006 | Holtzapple et al. | |
| 2006/0211101 A1 | 9/2006 | Chotani et al. | |
| 2006/0251764 A1 | 11/2006 | Abbas et al. | |
| 2006/0281157 A1 | 12/2006 | Chotani et al. | |
| 2007/0016095 A1 | 1/2007 | Low et al. | |
| 2007/0037259 A1 | 2/2007 | Hennessey et al. | |
| 2007/0118916 A1 | 5/2007 | Puzio et al. | |
| 2007/0148750 A1 | 6/2007 | Hoshino et al. | |
| 2007/0148751 A1 | 6/2007 | Griffin et al. | |
| 2007/0190626 A1 | 8/2007 | Wilkening et al. | |
| 2007/0275447 A1 | 11/2007 | Lewis et al. | |
| 2008/0014617 A1 | 1/2008 | Cerea | |
| 2008/0057555 A1 | 3/2008 | Nguyen | |
| 2008/0121359 A1 | 5/2008 | Holtzapple et al. | |
| 2008/0145903 A1 | 6/2008 | Holmes et al. | |
| 2008/0176301 A1 | 7/2008 | Granda et al. | |
| 2008/0227162 A1 | 9/2008 | Varanasi et al. | |
| 2008/0280338 A1 | 11/2008 | Hall et al. | |
| 2008/0286193 A1 | 11/2008 | Bento et al. | |
| 2009/0023187 A1 | 1/2009 | Foody et al. | |
| 2009/0042259 A1 | 2/2009 | Dale et al. | |
| 2009/0043686 A1 | 2/2009 | Matsumoto | |
| 2009/0064566 A1 | 3/2009 | Brummerstedt Iversen et al. | |
| 2009/0098617 A1 | 4/2009 | Burke et al. | |
| 2009/0117635 A1 | 5/2009 | Bradley et al. | |
| 2009/0181434 A1 | 7/2009 | Aikens et al. | |
| 2009/0298149 A1 | 12/2009 | Wang et al. | |
| 2010/0021980 A1 | 1/2010 | McDonald et al. | |

(56) References Cited

U.S. PATENT DOCUMENTS

| | | |
|---|---|---|
| 2010/0041119 A1 | 2/2010 | Christensen et al. |
| 2010/0055741 A1 | 3/2010 | Galvez, III et al. |
| 2010/0056774 A1 | 3/2010 | Anand et al. |
| 2010/0082139 A1 | 4/2010 | Macharia et al. |
| 2010/0082140 A1 | 4/2010 | Macharia et al. |
| 2010/0082166 A1 | 4/2010 | Macharia et al. |
| 2010/0143974 A1 | 6/2010 | Chung et al. |
| 2010/0144001 A1 | 6/2010 | Horton |
| 2010/0216201 A1 | 8/2010 | Soong et al. |
| 2010/0221805 A1 | 9/2010 | Kelly |
| 2010/0221819 A1 | 9/2010 | Foody et al. |
| 2010/0227369 A1 | 9/2010 | Narendranath et al. |
| 2010/0317053 A1 | 12/2010 | Stromberg et al. |
| 2011/0020874 A1 | 1/2011 | Hata |
| 2011/0079219 A1 | 4/2011 | McDonald et al. |
| 2011/0081689 A1 | 4/2011 | Flanegan et al. |
| 2011/0114765 A1 | 5/2011 | Brady et al. |
| 2011/0129886 A1 | 6/2011 | Howard et al. |
| 2011/0197496 A1 | 8/2011 | O'Connor et al. |
| 2011/0201084 A1 | 8/2011 | Wyman et al. |
| 2011/0212487 A1 | 9/2011 | Emme et al. |
| 2011/0223641 A1 | 9/2011 | Stephanopoulos et al. |
| 2011/0244499 A1 | 10/2011 | Realff et al. |
| 2011/0258911 A1 | 10/2011 | Hanson et al. |
| 2011/0258913 A1 | 10/2011 | Stamires et al. |
| 2011/0275860 A1 | 11/2011 | Beldring et al. |
| 2011/0300586 A1 | 12/2011 | Liu et al. |
| 2012/0006320 A1 | 1/2012 | Nguyen |
| 2012/0037325 A1 | 2/2012 | Beldring et al. |
| 2012/0041186 A1 | 2/2012 | Pschorn et al. |
| 2012/0100045 A1 | 4/2012 | Beldring et al. |
| 2012/0100577 A1 | 4/2012 | Medoff et al. |
| 2012/0107888 A1 | 5/2012 | Schmalisch et al. |
| 2012/0122162 A1 | 5/2012 | Romero et al. |
| 2012/0125324 A1 | 5/2012 | Fisk |
| 2012/0190092 A1 | 7/2012 | Jaquess et al. |
| 2012/0196233 A1 | 8/2012 | Ni et al. |
| 2012/0211427 A1 | 8/2012 | Bonanni et al. |
| 2012/0214205 A1 | 8/2012 | Iida et al. |
| 2012/0214216 A1 | 8/2012 | Brady et al. |
| 2012/0269715 A1 | 10/2012 | Kamegawa et al. |
| 2012/0282655 A1 | 11/2012 | Gibbs |
| 2013/0210101 A1 | 8/2013 | Parekh et al. |
| 2013/0274455 A1 | 10/2013 | Parekh et al. |
| 2013/0274456 A1 | 10/2013 | Parekh et al. |
| 2013/0323830 A1 | 12/2013 | Jerry |
| 2014/0038244 A1 | 2/2014 | Chesonis et al. |
| 2014/0106418 A1 | 4/2014 | Parekh et al. |
| 2014/0178944 A1 | 6/2014 | Parekh et al. |
| 2014/0188543 A1 | 7/2014 | Pearlmutter et al. |
| 2014/0342423 A1 | 11/2014 | Parekh et al. |
| 2015/0018584 A1 | 1/2015 | Parekh et al. |
| 2015/0196893 A1 | 7/2015 | Mennell et al. |
| 2015/0224428 A1 | 8/2015 | Lehoux et al. |
| 2015/0329927 A1 | 11/2015 | Parekh |
| 2016/0273009 A1 | 9/2016 | Lumpkin |

FOREIGN PATENT DOCUMENTS

| | | |
|---|---|---|
| EP | 0105937 B1 | 11/1987 |
| EP | 1259466 B1 | 10/2008 |
| EP | 1307735 B1 | 11/2008 |
| EP | 1299170 B1 | 8/2010 |
| JP | 2006149343 A | 6/2006 |
| KR | 20100123093 A | 11/2010 |
| KR | 20110046090 A | 5/2011 |
| KR | 20130115577 A | 10/2013 |
| KR | 101391435 B1 | 5/2014 |
| KR | 20140072866 A | 6/2014 |
| WO | WO-0132715 A1 | 5/2001 |
| WO | WO-0160752 A1 | 8/2001 |
| WO | WO-0200324 A1 | 1/2002 |
| WO | WO-0201220 A2 | 1/2002 |
| WO | WO-02001220 A3 | 9/2002 |
| WO | WO-2004081193 A2 | 9/2004 |
| WO | WO-2004108969 A1 | 12/2004 |
| WO | WO-2004113551 A1 | 12/2004 |
| WO | WO-2005052195 A1 | 6/2005 |
| WO | WO-2005087937 A2 | 9/2005 |
| WO | WO-2005118828 A1 | 12/2005 |
| WO | WO-2006024242 A1 | 3/2006 |
| WO | WO-2006101832 A2 | 9/2006 |
| WO | WO-2007009463 A2 | 1/2007 |
| WO | WO-2007009463 A3 | 7/2007 |
| WO | WO-2008020901 A2 | 2/2008 |
| WO | WO-2008073186 A2 | 6/2008 |
| WO | WO-2006101832 A3 | 4/2009 |
| WO | WO-2009063138 A2 | 5/2009 |
| WO | WO-2009087680 A2 | 7/2009 |
| WO | WO-2010011328 A1 | 1/2010 |
| WO | WO-2010037780 A1 | 4/2010 |
| WO | WO-2010056940 A2 | 5/2010 |
| WO | WO-2010068637 A1 | 6/2010 |
| WO | WO-2010115488 A1 | 10/2010 |
| WO | WO-2010123932 A1 | 10/2010 |
| WO | WO-2011003962 A2 | 1/2011 |
| WO | WO-2011022811 A1 | 3/2011 |
| WO | WO-2011028554 A1 | 3/2011 |
| WO | WO-2011028853 A1 | 3/2011 |
| WO | WO-2011103033 A1 | 8/2011 |
| WO | WO-2012051523 A1 | 4/2012 |
| WO | WO-2012099967 A1 | 7/2012 |
| WO | WO-2012155239 A1 | 11/2012 |
| WO | WO-2013186184 A1 | 12/2013 |

OTHER PUBLICATIONS

Agbor, et al. Biomass pretreatment: fundamentals toward application. Biotechnol Adv. Nov.-Dec. 2011;29(6):675-85. doi: 10.1016/j.biotechadv.2011.05.005. Epub May 23, 2011.

Alcohol and Tobacco Tax and Trade Bureau, treasury. 27 C.F.R. §19.134 Bonded warehouse not on premises qualified for production of spirits, p. 381, Apr. 1, 1997 revision.

Aldrich. 2003-2004. Particle size conversion Table, 2 Pages or Page T848 of the Aldrich 2003-2004 Catalog/ Handbook of Fine Chemicals.

Ballesteros, et al. Ethanol from lignocellulose materials by a simultaneous saccharification and fermentation process (SFS) with Kluyveromyces marxianus CECT 10875. Process Biochemistry, vol. 39, pp. 1843-1848, 2004.

Boggan. 2003. Alcohol, Chemistry and You Sources and Uses of Ethyl Alcohol. Kennesaw State University, pp. 1-5, Printed May 17, 2010. http://www.chemcases.com/alcohol/alc-03.htm/.

Bolsen, et al. Silage Fermentation and Silage Additives: Review. AJAS 1996 vol. 9 (No. 5). pp. 483-493.

Brigham, et al. Bacterial Carbon Storage to Value Added Products. J Microbial Biochem Technol 2011, S3-002.

Co-pending U.S. Appl. No. 14/971,481, filed Dec. 16, 2015.

Dale, et al. Hydrolysis of lignocellulosics at low enzyme levels: Application of the AFEX process. Bioresource Technology. Apr. 1996; 56(1):111-116.

Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.

Dionex CarboPac PA10. Column Product Manual. Thermo Scientific. P/N: 065495-01. Dec. 2012.

Dowe, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Dowe, et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages) 2008.

European search report and search opinion dated Sep. 25, 2015 for EP Application No. 13747149.6.

(56) References Cited

OTHER PUBLICATIONS

European search report and search opinion dated Sep. 28, 2015 for EP Application No. 13775895.9.
Felix et al. In vitro and in vivo digestibility of soya-bean straw treated with various alkalis. Anim Prod. 1990; 51:47-61.
Gibreel, et al. Fermentation of barley by using *Saccharomyces cerevisiae*: examination of barley as a feedstock for bioethanol production and value-added products. Appl Environ Microbiol. Mar. 2009;75(5):1363-72. doi: 10.1128/AEM.01512-08. Epub Dec. 29, 2008.
Gum,et al. Structural characterization of a glycoprotein cellulase, 1,4-beta-D-glucan cellubiohydrolase C from trichodermaviride. Biochem. Biophys. Acta. 1976; 446:370-86.
International search report and written opinion dated Jan. 26, 2010for PCT/US2009/67221.
International search report and written opinion dated Mar. 8, 2016 for PCT Application No. US2014/033567.
International search report and written opinion dated Apr. 1, 2016 for PCT Application No. US2015/064850.
International search report and written opinion dated May 30, 2013 for PCT/US2013/025457.
International search report and written opinion dated Jun. 20, 2013 for PCT/US2013/036497.
International search report and written opinion dated Jul. 26, 2013 for PCT Application No. US2013/032955.
International search report and written opinion dated Jul. 29, 2015 for PCT Application No. US2015/031146.
International search report and written opinion dated Nov. 19, 2013 for PCT/US2013/054411.
International search report dated Aug. 25, 2014 for PCT Application No. US2014/027850.
International search report dated Sep. 8, 2014 for PCT Application No. US2014/039399.
Jones, et al. (1994, Ethanolic Fermentation of Blackstrap Molasses and Sugarcane Juice Using Very High Gravity Technology. J. Agric. Food Chem, vol. 42, pp. 1242-1246).
Kim, et al. Lime pretreatment and enzymatic hydrolysis of corn stover. Bioresour Technol. Dec. 2005;96(18):1994-2006.
Kim, et al. Pretreatment and fractionation of corn stover by ammonia recycle percolation process. Bioresour Technol. Dec. 2005;96(18):2007-13.
Larsson, et al. Comparison of different methods for the detoxification of lignocellulose hydrolyzates of spruce. Applied Biochemistry and Biotechnology. 1999; 77-79:91-103.
Lloyd, et al. Combined sugar yields for dilute sulfuric acid pretreatment of corn stover followed by enzymatic hydrolysis of the remaining solids. Bioresour Technol. Dec. 2005;96(18):1967-77.
Malherbe, et al. Lignocellulose biodegradation: Fundamentals and applications. Re/Views in Environmental Science & Bio/Technology. 2001; 1:105-114.
Mosier, et al. Features of promising technologies for pretreatment of lignocellulosic biomass. Bioresour Technol. Apr. 2005;96(6):673-86.
Mosier, et al. Optimization of pH controlled liquid hot water pretreatment of corn stover. Bioresour Technol. Dec. 2005;96(18):1986-93.
Nevoigt, et al. Osmoregulation and glycerol metabolism in the yeast *Saccharomyces cerevisiae*. FEMS Microbiol Rev. Nov. 1997;21(3):231-41.
Notice of allowance dated Jan. 9, 2013 for U.S. Appl. No. 13/646,425.
Notice of allowance dated Feb. 20, 2014 for U.S. Appl. No. 13/731,633.
Notice of allowance dated Jun. 7, 2013 for U.S. Appl. No. 12/633,555.
Notice of allowance dated Jul. 8, 2013 for U.S. Appl. No. 13/686,477.
Notice of allowance dated Jul. 14, 2016 for U.S. Appl. No. 14/050,244.
Notice of allowance dated Aug. 8, 2013 for U.S. Appl. No. 12/633,555.
Notice of allowance dated Oct. 15, 2012 for U.S. Appl. No. 11/974,129.
Office action dated Jan. 5, 2016 for U.S. Appl. No. 14/050,244.
Office action dated Feb. 5, 2016 for U.S. Appl. No. 13/947,368.
Office action dated Feb. 20, 2013 for U.S. Appl. No. 13/686,477.
Office action dated Mar. 10, 2015 for U.S. Appl. No. 13/931,303.
Office action dated Mar. 12, 2015 for U.S. Appl. No. 14/050,244.
Office action dated Mar. 20, 2013 for U.S. Appl. No. 12/633,555.
Office action dated Mar. 24, 2014 for U.S. Appl. No. 13/724,763.
Office action dated May 24, 2010 for U.S. Appl. No. 11/974,129.
Office action dated Jun. 25, 2013 for U.S. Appl. No. 13/731,633.
Office action dated Jul. 6, 2012 for U.S. Appl. No. 11/974,129.
Office action dated Jul. 9, 2015 for U.S. Appl. No. 13/793,860.
Office action dated Jul. 28, 2016 for U.S. Appl. No. 14/254,441.
Office action dated Sep. 11, 2015 for U.S. Appl. No. 14/254,441.
Office action dated Sep. 21, 2015 for U.S. Appl. No. 13/842,941.
Office action dated Oct. 3, 2012 for U.S. Appl. No. 12/633,555.
Office action dated Oct. 8, 2014 for U.S. Appl. No. 13/793,860.
Office action dated Oct. 18, 2013 for U.S. Appl. No. 13/724,763.
Office action dated Nov. 8, 2010 for U.S. Appl. No. 11/974,129.
Office action dated Dec. 29, 2014 for U.S. Appl. No. 13/842,941.
Office action dated Apr. 7, 2016 for U.S. Appl. No. 14/050,244.
Palmqvist, et al. Fermentation of lignocellulosic hydrolysates. I: inhibition and detoxification. Bioresource Technology. 2000; 74(1):17-24.
Parekh, et al. Production of glycerol by hansenula anomala. Biotechnol Bioeng. Jul. 1985;27(7):1089-91.
Quantitative Instrument Analysis, https://www.gmu.edu/depts/SRIF/tutorial/gcd/quant.htm, p. s1-3; Updated May 8, 1998, Printed Jun. 23, 2015.
Santoro, et al. A High-throughput Platform for Screening Milligram Quantities of Plant Biomass for Lignocellulose Digestibility. Bioenerg. Res. Jan. 2010; 3:93-102.
Shapouri, et al. 2006. The Economic Feasibility of Ethanol Production From Sugar in the United States, USDA, 78 Pages, Jul. 2006.
Silva, et al. Downstream processing for xylitol recovery from fermented sugar cane bagasse hydrolysate using aluminium polychloride. Z Naturforsch C. Jan.-Feb. 2000;55(1-2):10-5.
Sluiter, et al. Determination of structural carbohydrates and lignin in biomass. National Renewable Energy Laboratory. Technical report NREL/TP-510-42618. Revised Jun. 2010.
Sun, et al. Dilute acid pretreatment of rye straw and bermudagrass for ethanol production. Bioresour Technol. Sep. 2005;96(14):1599-606. Epub Feb. 24, 2005.
Taherzadeh, et al. Pretreatment of Lignocellulosic Wastes to Improve Ethanol and Biogas Production: A Review. International Journal of Molecular Sciences. 2008(9). pp. 1621-1651.
Taylor. From Raw Sugar to Raw materials. Chemical innovation. 2000; 30:45-48.
USDA, "The Economic Feasibility of Ethanol Production From Sugar in the United States"; Jul. 2006, 69 pages.
Varhegyi, et al. (1989. Kinetics of the thermal decomposition of cellulose, hemicellulose, and sugarcane bagasse. Energy Fuels, vol. 3, No. 3, pp. 329-335).
Waiss, et al. Improving Digestibility of Straws for Ruminant Feed by Aqueous Ammonia. Journal of Animal Science. 1972; 35(1):109-112.
Wallace., "Feasibility Study of Co-Locating and Integrating Ethanol Production Plants from Corn Starch and Lignocellulosic Feedstocks. United States Department of Agriculture, United States Department of Energy, 2005, NREL, Golden Colorado, Wyndmoor, PA."
Waltermann, et al. *Rhodococcus opacus* strain PD630 as a new source of high-value single-cell oil? Isolation and characterization of triacylglycerols and other storage lipids. Microbiology. 2000; 146:1143-1149.
Woiciechowski, et al. Acid and Enzymatic Hydrolysis to Recover Reducing Sugars from Cassava Bagasse: an Economic Study. Brazilian Archives of Biology and Technology, vol. 45, No. 3, pp. 393-400, 2002.

(56) References Cited

OTHER PUBLICATIONS

Zheng, et al. Extrusion Pretreatment of Lignocellulosic Biomass: A Review. Int. J. Mol. Sci. Oct. 2014, 15, 18967-18984.
Co-pending U.S. Appl. No. 15/267,617, filed Sep. 16, 2016.
Co-pending U.S. Appl. No. 15/293,478, filed Oct. 14, 2016.
Co-pending U.S. Appl. No. 15/418,204, filed Jan. 27, 2017.
Co-pending U.S. Appl. No. 15/430,370, filed Feb. 10, 2017.
International search report and written opinion dated Nov. 30, 2016 for PCT Application No. US-2016052143.
Office action dated Sep. 16, 2016 for U.S. Appl. No. 13/947,368.
Office action dated Jan. 19, 2017 for U.S. Appl. No. 14/340,179.
Office action dated Dec. 5, 2016 for U.S. Appl. No. 13/842,941.
Office action dated Jan. 23, 2017 for U.S. Appl. No. 14/140,880.

\* cited by examiner

A.

US 9,809,867 B2

CARBON PURIFICATION OF CONCENTRATED SUGAR STREAMS DERIVED FROM PRETREATED BIOMASS

CROSS-REFERENCE

This application is a National Stage Entry of International Application No. PCT/US2014/027850, filed Mar. 14, 2014, which claims the benefit of U.S. Provisional Application No. 61/800,001, filed Mar. 15, 2013, each of which application is incorporated herein by reference in its entirety.

BACKGROUND OF THE INVENTION

Bioplastics are an increasingly well-know alternative to petroleum-based plastics. Derived from sugars, compounds such as PLA (polylactic acid), PHB (poly-3-hydroxybutyrate), and PHA (polyhydroxyalkanoates) have found their way into the marketplace and the demand for them is growing. Similar demands are being made for biochemicals made from sugars instead of fossil oil supplies. To compete, however, the bioplastic and biochemical industries require sugars that are decolorized and highly refined to enable their proprietary microbes or chemical catalysis technology to produce the initial chemical derivatives, such as succinic acid, for synthesizing plastics. For cellulosic and lignocellulosic sugar suppliers, this can necessitate clarifying and reducing the toxic compounds in the sugar streams during and/or after pretreatment to assure that the custom-designed sugar stream meet the necessary specifications for these industries. Inhibitors such as furfural, HMF (hydroxymethylfurfural), acetic acid and other phenolics must be reduced to an acceptable level.

The use of activated carbon has been used to sequester color in the chemical industry as well as reduce inhibitors found in various sugar broths. To date, however, clarification and reduction of inhibitors in sugar streams derived from cellulosic or lignocellulosic materials has been limited to dilute streams. This refinement is often only partially effective and can increase the cost of the sugars due to the high cost of evaporation later to concentrate the sugars. There is a need for improve carbon filtration methods that can be used on a concentrated sugar stream from cellulosic or lignocellulosic biomass to reduce pigmentation as well as the inhibitor concentration within the sugar stream.

SUMMARY OF THE INVENTION

Disclosed herein are methods of refining a sugar stream, the methods comprising: (a) heating activated carbon to a temperature of from about 100° C. to about 300° C. to produce heat activated carbon; (b) contacting the sugar stream with the heat activated carbon for a sufficient time to produce a refined sugar stream, wherein the heat activated carbon is at a temperature greater than the sugar stream.

Also disclosed herein are methods of refining a sugar stream, the methods comprising: (a) acidifying the sugar stream to a pH of from about 1 to about 4 by adding an acid to produce an acidified sugar stream; and (b) contacting the acidified sugar stream with activated carbon for a sufficient time to produce a refined sugar stream. Some embodiments further comprise heating the activated carbon to a temperature of from about 100° C. to about 300° C. to produce heat activated carbon, wherein the contacting is performed with heat activated carbon, and wherein the heat activated carbon is at a temperature greater than the sugar stream.

Also disclosed herein are methods of producing a refined sugar stream, the methods comprising: (a) pretreating or hydrolyzing a biomass comprising cellulosic, hemicellulosic, or lignocellulosic material to produce a sugar stream, wherein the sugar stream has a total sugar concentration of about 15% or greater; and (b) contacting the sugar stream with activated carbon for a sufficient time to produce the refined sugar stream. Some embodiments further comprise heating the activated carbon to a temperature of from about 100° C. to about 300° C. to produce heat activated carbon, wherein the contacting is performed with heat activated carbon, wherein the heat activated carbon is at a temperature greater than the sugar stream. Some embodiments further comprise acidifying the sugar stream to a pH of from about 1 to about 4 by adding an acid to produce an acidified sugar stream, wherein contacting is performed with the acidified sugar stream. Some embodiments further comprise heating the activated carbon to a temperature of from about 100° C. to about 300° C. to produce heat activated carbon and acidifying the sugar stream to a pH of from about 1 to about 4 by adding an acid to produce an acidified sugar stream, wherein contacting is performed with heat activated carbon and the acidified sugar stream, wherein the heat activated carbon is at a temperature greater than the acidified sugar stream.

Also disclosed are methods of refining a sugar stream, the methods comprising: (a) heating activated carbon to produce heat activated carbon; (b) storing the heat activated carbon in a non-oxidizing environment; and (c) contacting the sugar stream with the heat activated carbon for a sufficient time to produce a refined sugar stream. Some embodiments further comprise acidifying the sugar stream to a pH of from about 1 to about 4 by adding an acid to produce an acidified sugar stream, wherein contacting is performed with the acidified sugar stream.

The sugar stream is a liquid. The activated carbon is a solid.

Some embodiments further comprise pretreating or hydrolyzing a biomass comprising cellulosic, hemicellulosic, or lignocellulosic material to produce the sugar stream.

In some embodiments, the activated carbon adsorbs less than about 20% of the sugars in the sugar stream during contacting. In some embodiments, the activated carbon adsorbs less than about 10% of the sugars in the sugar stream during contacting.

In some embodiments, the sugar stream comprises one or more inhibitors and wherein contacting the sugar stream with activated carbon removes about 70% or more of at least one of the inhibitors from the sugar stream. In some embodiments, the one or more inhibitors comprise furfural, hydroxymethylfurfural, or a combination thereof. In some embodiments, contacting the sugar stream with activated carbon removes about 80% or more of at least one of the inhibitors.

In some embodiments, contacting the sugar stream with activated carbon increases the transparency of the sugar stream by about 50% or more. In some embodiments, the transparency is measured at 600 nm. In some embodiments, the transparency is increased by 75% or more.

In some embodiments, the sugar stream comprises one or more aromatic or phenolic compounds and wherein contacting the sugar stream with activated carbon removes about 30% or more of at least one of the aromatic or phenolic compounds from the sugar stream. In some embodiments, contacting the sugar stream with activated carbon removes about 50% or more of at least one of the aromatic or phenolic compounds. In some embodiments, contacting the sugar stream with activated carbon removes about 70% or more of at least one of the aromatic or phenolic compounds.

In some embodiments, heating the activated carbon is to a temperature of from about 150° C. to about 900° C. In some embodiments, heating the activated carbon is to a temperature of from about 150° C. to about 750° C. In some embodiments, heating the activated carbon is to a temperature of from about 150° C. to about 500° C. In some embodiments, heating the activated carbon is to a temperature of from about 150° C. to about 250° C. In some embodiments, heating the activated carbon is to a temperature of from about 175° C. to about 225° C. In some embodiments, heating the activated carbon is to a temperature of about 200° C.

In some embodiments, heating the activated carbon is for a time of from about 1 hour to about 48 hours. In some embodiments, heating the activated carbon is for a time of from about 4 hours to about 24 hours.

In some embodiments, heating the activated carbon is performed in an oven.

In some embodiments, heating the activated carbon is performed in an autoclave.

In some embodiments, heating the activated carbon is performed in a vacuum.

In some embodiments, contacting is performed within about 4 hours of heating. In some embodiments, contacting is performed within about 1 hour of heating. In some embodiments, contacting is performed within about 45 minutes of heating. In some embodiments, contacting is performed within about 30 minutes of heating.

In some embodiments, the heat activated carbon is stored in a non-oxidizing environment before contacting.

In some embodiments, the heat activated carbon is stored in an inert gas before contacting. In some embodiments, the inert gas is nitrogen, argon, helium, neon, krypton, xenon, radon, carbon dioxide, or a combination thereof.

In some embodiments, the heat activated carbon is in an oxygen-free environment before contacting.

In some embodiments, the heat activated carbon is stored is a water-free environment before contacting.

In some embodiments, the temperature of the heat activated carbon during contacting is greater than room temperature. In some embodiments, the temperature of the heat activated carbon during contacting is about 65° C. or greater. In some embodiments, the temperature of the heat activated carbon during contacting is about 100° C. or greater.

In some embodiments, the temperature of the heat activated carbon during contacting is from about 50° C. to about 250° C. In some embodiments, the temperature of the heat activated carbon during contacting is from about 75° C. to about 200° C. In some embodiments, the temperature of the heat activated carbon during contacting is about 200° C.

In some embodiments, acidifying the sugar stream is to the pH of from about 1.5 to about 3.

In some embodiments, the sugar stream has a total sugar concentration of from about 5% to about 60%. In some embodiments, the sugar stream has a total sugar concentration of from about 15% to about 40%.

In some embodiments, the sugar stream was produced by pretreating or hydrolyzing a biomass comprising cellulosic, hemicellulosic, or lignocellulosic material. In some embodiments, pretreating or hydrolyzing the biomass comprises mechanical size reduction, hot water treatment, acid treatment, base treatment, steam explosion, acid-catalyzed steam explosion, ammonia fiber/freeze explosion, enzymatic hydrolysis, or a combination thereof. In some embodiments, pretreating or hydrolyzing the biomass comprises mechanical size reduction, acid treatment and enzymatic hydrolysis.

In some embodiments, the sugar stream was produced by (1) pretreating a biomass comprising lignocellulosic material with hot water or an acid to solubilize hemicellulose in the biomass, (2) substantially separating solubilized hemicellulose from remaining lignocellulosic solids, and (3) enzymatically hydrolyzing cellulose in the remaining lignocellulosic solids.

In some embodiments, the sugar stream was produced by: (a) pretreating a biomass comprising cellulosic, hemicellulosic, or lignocellulosic material to produce a pretreated biomass comprising solid particles and optionally a yield of C5 monomers and/or dimers that is at least 50% of a theoretical maximum, wherein pretreating comprises: (i) hydration of the biomass in an aqueous medium to produce a hydrated biomass, (ii) mechanical size reduction of the hydrated biomass to produce the solid particles, and (iii) heating the hydrated biomass for a time sufficient to produce the pretreated biomass comprising the optional yield of C5 monosaccharides and/or disaccharides; and (b) hydrolyzing the pretreated biomass composition with one or more enzymes for a time sufficient to produce the sugar stream. In some embodiments, the aqueous medium comprises and acid. In some embodiments, the acid is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

In some embodiments, the sugar stream is a crude sugar stream.

In some embodiments, the sugar stream is a hydrolysate from the pretreatment and hydrolysis of a biomass comprising cellulose, hemicellulose, or lignocellulose.

In some embodiments, the sugar stream comprises C5 sugars, C6 sugars, or a combination thereof. In some embodiments, sugars in the sugar stream are monomers, dimers, or a combination thereof.

In some embodiments, at least about 70% of sugars in the sugar stream are C5 sugars. In some embodiments, at least about 80% of sugars in the sugar stream are C5 sugars. In some embodiments, at least about 90% of sugars in the sugar stream are C5 sugars. In some embodiments, at least about 70% of sugars in the sugar stream are C6 sugars.

In some embodiments, at least about 80% of sugars in the sugar stream are C6 sugars. In some embodiments, at least about 90% of sugars in the sugar stream are C6 sugars. In some embodiments, at least about 95% of sugars in the sugar stream are C6 sugars.

Some embodiments further comprise heating the sugar stream prior to contacting with the activated carbon. In some embodiments, the sugar stream is at a temperature of from about 45° C. to about 100° C. In some embodiments, the sugar stream is at a temperature of from about 55° C. to about 75° C.

In some embodiments, the sufficient time is from about 30 minutes to about 5 hours. In some embodiments, the sufficient time is from about 1 hour to about 2 hours.

In some embodiments, the activated carbon is granular activated carbon, powdered activated carbon, graphene, or a combination thereof. In some embodiments, the activated carbon is powdered activated carbon.

In some embodiments, the activated carbon is contained within the sugar stream at a concentration of from about 1% to about 20% during contacting. In some embodiments, the activated carbon is contained within the sugar stream at a concentration of from about 5% to about 15% during contacting. In some embodiments, the activated carbon is contained within the sugar stream at a concentration of about 10% during contacting.

In some embodiments, the activated carbon has a particle size of from about 5 microns to about 40 microns. In some embodiments, the activated carbon has a particle size averaging from about 5 microns to about 10 microns.

In some embodiments, the sugar stream is agitated, mixed, stirred, blended, shaken, sonicated, subjected to bubbling with a gas, subjected to bubbling with an inert gas, or any combination thereof during some or all of the contacting.

Some embodiments further comprise contacting the sugar stream with diatomaceous earth.

Some embodiments further comprise removing the activated carbon from the sugar stream after the sufficient time.

Also disclosed are refined sugar streams produced by any of the methods disclosed herein.

Also disclosed are refined sugar stream comprising one or more of the following: (a) a concentration of total sugars that is at least about 15% w/v; (b) a concentration of one or more inhibitors that is at least about 70% less than an originator sugar stream; (c) a concentration of one or more aromatic or phenolic compounds that is at least about 30% less than the originator sugar stream; or (d) a transparency that is at least 50% higher than the originator sugar stream, wherein the refined sugar stream was contacted with activated carbon.

In some embodiments, the concentration of total sugars is from about 15% to about 60% w/v.

In some embodiments, the concentration of one or more inhibitors is at least about 80% less than in the originator sugar stream.

In some embodiments, the concentration of one or more aromatic or phenolic compounds is at least about 50% less than in the originator sugar stream. In some embodiments, the concentration of one or more aromatic or phenolic compounds is at least about 70% less than in the originator sugar stream.

In some embodiments, the transparency is at least 75% higher than in the originator sugar stream. In some embodiments, the transparency is measured at 600 nm.

In some embodiments, the refined sugar stream has a concentration of total sugars of from about 5% to about 60%. In some embodiments, the refined sugar stream has a concentration of total sugars of from about 15% to about 40%.

In some embodiments, the originator sugar stream was produced by pretreating or hydrolyzing a biomass comprising cellulosic, hemicellulosic, or lignocellulosic material. In some embodiments, pretreating or hydrolyzing the biomass comprises mechanical size reduction, hot water treatment, acid treatment, base treatment, steam explosion, acid-catalyzed steam explosion, ammonia fiber/freeze explosion, enzymatic hydrolysis, or a combination thereof. In some embodiments, pretreating or hydrolyzing the biomass comprises mechanical size reduction, acid treatment and enzymatic hydrolysis.

In some embodiments, the originator sugar stream was produced by (1) pretreating a biomass comprising lignocellulosic material with hot water or an acid to solubilize hemicellulose in the biomass, (2) substantially separating solubilized hemicellulose from remaining lignocellulosic solids, and (3) enzymatically hydrolyzing cellulose in the remaining lignocellulosic solids.

In some embodiments, the originator sugar stream was produced by: (a) pretreating a biomass comprising cellulosic, hemicellulosic, or lignocellulosic material to produce a pretreated biomass comprising solid particles and optionally a yield of C5 monomers and/or dimers that is at least 50% of a theoretical maximum, wherein pretreating comprises: (i) hydration of the biomass in an aqueous medium to produce a hydrated biomass, (ii) mechanical size reduction of the hydrated biomass to produce the solid particles, and (iii) heating the hydrated biomass for a time sufficient to produce the pretreated biomass comprising the optional yield of C5 monosaccharides and/or disaccharides; and (b) hydrolyzing the pretreated biomass composition with one or more enzymes for a time sufficient to produce the sugar stream. In some embodiments, the aqueous medium comprises and acid. In some embodiments, the acid is sulfuric acid, peroxyacetic acid, lactic acid, formic acid, acetic acid, citric acid, phosphoric acid, hydrochloric acid, sulfurous acid, chloro acetic acid, dichloroacetic acid, trichloroacetic acid, trifluoroacetic acid, oxalic acid, benzoic acid, or a combination thereof.

In some embodiments, the originator sugar stream is a crude originator sugar stream.

In some embodiments, the originator sugar stream is a hydrolysate from the pretreatment and hydrolysis of a biomass comprising cellulose, hemicellulose, or lignocellulose.

In some embodiments, the refined sugar stream comprises C5 sugars, C6 sugars, or a combination thereof.

In some embodiments, at least about 70% of sugars in the refined sugar stream are C5 sugars. In some embodiments, at least about 80% of sugars in the refined sugar stream are C5 sugars. In some embodiments, at least about 90% of sugars in the refined sugar stream are C5 sugars In some embodiments, at least about 70% of sugars in the refined sugar stream are C6 sugars. In some embodiments, at least about 80% of sugars in the refined sugar stream are C6 sugars. In some embodiments, at least about 90% of sugars in the refined sugar stream are C6 sugars. In some embodiments, at least about 95% of sugars in the refined sugar stream are C6 sugars.

In some embodiments, sugars in the refined sugar stream are monomers, dimers, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference. In the event that a term incorporated by reference conflicts with a term defined herein, this specification shall control.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
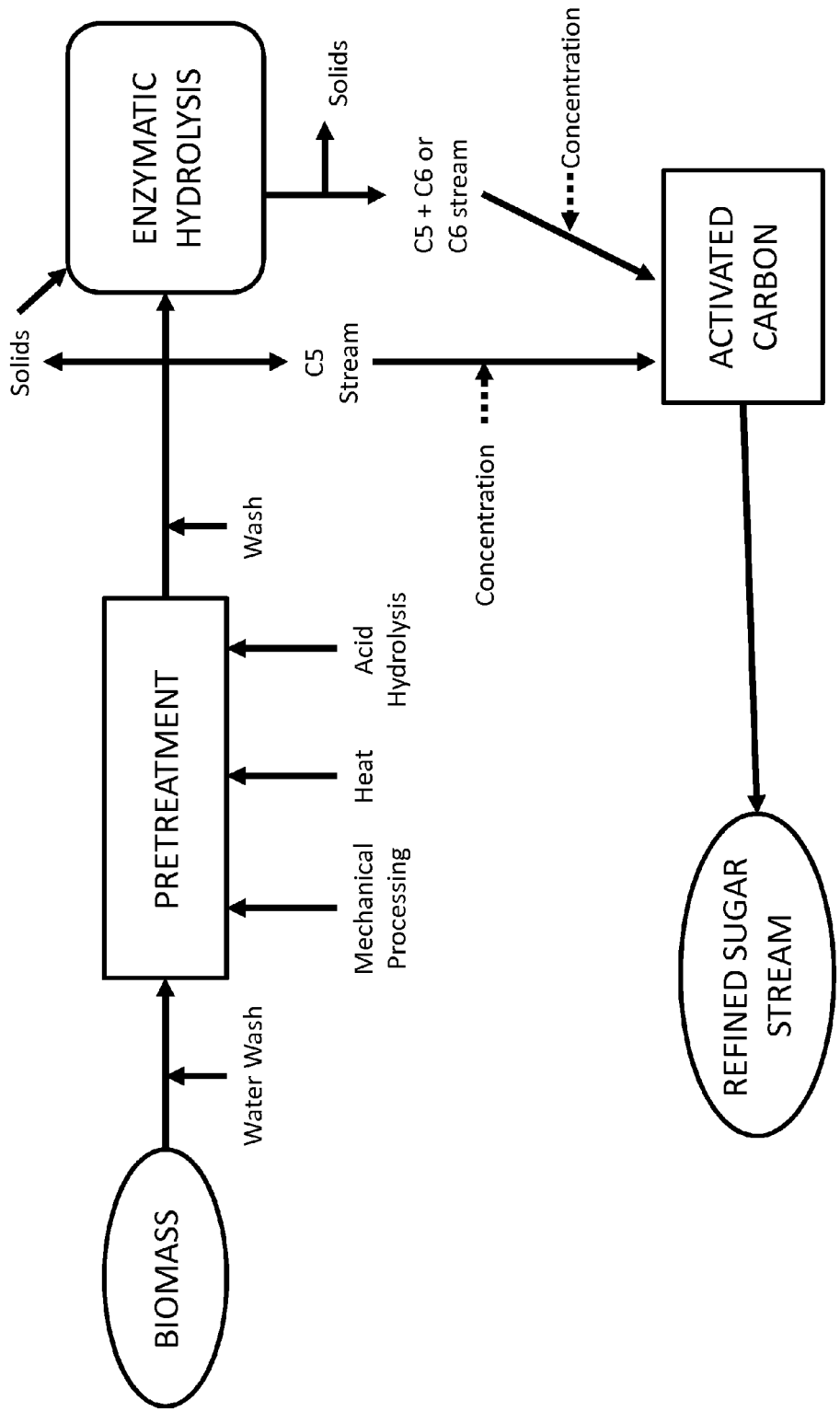
FIG. 1 is a block diagram depicting the several stage pretreatment process, showing the lignocellulosic feedstock entering into the hydrolysis process system, thereby producing sugar hydrolysate products (sugar stream) and a lignin residue solid product.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

"About" means a referenced numeric indication plus or minus 10% of that referenced numeric indication. For example, the term about 4 would include a range of 3.6 to 4.4. All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

Currently most of the global supply for fermentable refined C6 sugars is derived by processing renewable feedstocks rich in starch, such as corn, rice, cassava, wheat, sorghum and in few cases, cane sugar (comprised of glucose and fructose). Production of refined C6 sugars from these feedstocks is well established and is relatively simple because the starch is concentrated in particular plant parts (mostly seeds) and can be easily isolated and hydrolyzed to monomeric sugars using amylase enzymes. Saccharification is performed at low temperatures, resulting in less inhibitors and breakdown products. Starch is typically a white amorous powder and does not contain any interfering complex phenolics, acids, extractives, or colored compounds. Even if these are present, they are in such low quantity that, it is easy to refine and remove these compounds. These attributes have enabled corn refiners and starch processing companies then to provide highly-concentrated, refined sugars within tight specifications at low cost using anion exchange columns and low levels of sequestering agents.

Most of the bioplastics and biochemical industries including the pharmaceutical companies have therefore developed and defined their technology around the use of these sugars. As the sugar-producing industry moves over to lignocellulosic biomass-derived sugars; however, inhibitor reduction and purification becomes more of a challenge.

Lignocellulosic biomass can require higher temperatures to depolymerize the sugars contained within and, in some cases, explosion and more violent reaction with steam (explosion) and/or acid to make it ready for enzyme hydrolysis. The C5 and C6 sugars are naturally embedded in and cross-linked with lignin, extractives and phenolics. Hemicellulose has acetic ether bonds and its breakdown leads to acid formation. The high temperature and pressures used during pretreatment can result in the leaching of lignin and aromatics, which are dark brown, loading with mixed sugars, high ash, lignin aromatic fragments, inhibitors such as HMF and furfural, and acids in stream. Producing a higher sugar concentration in the sugar stream, and thus minimize evaporation cost, can require high solids concentration processing which inevitably leads to increased phenolics and inhibitor levels. Recovered sugars therefore can require expensive pretreatment and a costly refinement process to remove the substantial amount of inhibitors, sugar breakdown products, and color relative to starch-based conversion. This process can comprise multiple steps, including color removal, ion exchange and other expensive procedures performed on dilute sugar streams, after which streams are often further concentrated for customers.

These underlying complex challenges have been one of the key reasons that cellulosic-derived sugars are not only expensive, but in some cases remain challenging to compete economically with starch-based sugar technology. Biochemical and bioplastics industries, due to their stringent process operations, demand the same level of refinement for cellulosic sugars as they demand for starch-based sugars. There is a need for cellulosic-based sugar platform technology to develop unique, simple, scaleable, and feedstock flexible technology such that a higher concentration of cellulosic sugar hydrolysate can be rapidly processed, refined, clarified, and still be competitive with starch-based sugar recovery and economics. To date, most of the work at research and processing centers such as the DOE, NREL and other laboratories developing cellulosic sugar platforms, are based on dilute streams of biomass hydrolysate and refinement of sugars. But dilute streams will need further evaporation—leading to higher energy and operating cost.

Carbon, including activated carbon, can be used to decolorize and purify sugar solutions. Activated carbon, also called activated charcoal or activated coal, is a form of carbon processed to be riddled with small, low-volume pores that increase the surface area available for adsorption or chemical reactions. For purification of sugars that have been easily extracted, such as molasses, sucrose, or starch (dextrose), various methods have been developed for carbon purification of sugar solutions such as raising temperatures, flocculating with polycarbonates and polyacrylimides, varying pH and granular size. See, for example, U.S. Pat. Nos. 6,475,552, 4,288,551, 3,730,770, and 4,502,890.

Often, carbon is combined with other compounds such as lime, polyelectrolytes, and ion exchange resins) to remove impurities and color in food-based sucrose or dextrose syrups, or in paper-making operations. See, for example, US Patent Application No. 2012/0196233. No simple method of decolorizing cellulosic or lignocellulosic-derived C5 and C6 sugars with carbon has been developed. In one attempt, see US Patent application No. 2012/0211427, spherical adsorbents have been developed to provide maximum surface area similar to charcoal carbon. These, however, adsorb considerable amounts of sugars and must be carefully regenerated while separating the inhibitors. It also costs more to make such adsorbants. To date, no inexpensive carbon-based method of refining these sugar streams at high concentrations has been found that removes the inhibitors that form during pretreatment of biomass without adsorbing sugars to a great extent. The biochemicals and bioplastics industries require highly refined sugar streams for fermentation and/or synthesis of compounds such as succinic acid. To produce, for example, bioplastics such as PHA, that compete with PHA made from fossil carbohydrates, a highly refined, decolorized carbohydrate platform is desired.

Such refinement may be able to be produced from dilute streams, processed through activated carbon and then ion exchange columns, but such end processes are expensive and require concentration of the sugar stream following refinement. To reduce the cost of purified sugars for industries that need them, herein is described a novel process using activated carbon. The process minimizes the loss of sugars and sugar polymers in concentrated sugar streams derived from pretreatment of cellulosic and lignocellulosic materials, while decolorizing the sugar stream and reducing the concentration of inhibitors.

In this specification and in the claims that follow, reference will be made to a number of terms which shall be defined to have the following meanings.

Definitions

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

"Or" can be used disjunctively or conjunctively.

Unless characterized otherwise, technical and scientific terms used herein have the same meaning as commonly understood by one of ordinary skill in the art.

"Fermentive end-product" and "fermentation end-product" are used interchangeably herein to include bio fuels, chemicals, compounds suitable as liquid fuels, gaseous fuels, triacylglycerols, reagents, chemical feedstocks, chemical additives, processing aids, food additives, bioplastics and precursors to bioplastics, and other products. Examples of fermentive end-products include but are not limited to 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl) butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-) ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethyl-nonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal. undecanoate, n-dodecane, 1-dodecene, 1-dodecanol, dodecanal, dodecanoate, n-dodecane, 1-decadecene, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1, 8-dicarboxylic acid, glycerol, fucoidan, iodine, chlorophyll, carotenoid, calcium, magnesium, iron, sodium, potassium, phosphate, lactic acid, acetic acid, formic acid, isoprenoids, and polyisoprenes, including rubber. Further, such products can include succinic acid, pyruvic acid, enzymes such as cellulases, polysaccharases, lipases, proteases, ligninases, and hemicellulases and may be present as a pure compound, a mixture, or an impure or diluted form.

Fermentation end-products can include polyols or sugar alcohols; for example, methanol, glycol, glycerol, erythritol, threitol, arabitol, xylitol, ribitol, mannitol, sorbitol, dulcitol, fucitol, iditol, inositol, volemitol, isomalt, maltitol, lactitol, and/or polyglycitol.

The term "fatty acid comprising material" as used herein has its ordinary meaning as known to those skilled in the art and can comprise one or more chemical compounds that include one or more fatty acid moieties as well as derivatives of these compounds and materials that comprise one or more of these compounds. Common examples of compounds that include one or more fatty acid moieties include triacylglycerides, diacylglycerides, monoacylglycerides, phospholipids, lysophospholipids, free fatty acids, fatty acid salts, soaps, fatty acid comprising amides, esters of fatty acids and monohydric alcohols, esters of fatty acids and polyhydric alcohols including glycols (e.g. ethylene glycol, propylene glycol, etc.), esters of fatty acids and polyethylene glycol, esters of fatty acids and polyethers, esters of fatty acids and polyglycol, esters of fatty acids and saccharides, esters of fatty acids with other hydroxyl-containing compounds, etc.

The term "pH modifier" as used herein has its ordinary meaning as known to those skilled in the art and can include any material that will tend to increase, decrease or hold steady the pH of the broth or medium. A pH modifier can be an acid, a base, a buffer, or a material that reacts with other materials present to serve to raise, lower, or hold steady the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. In one embodiment, a buffer can be produced in the broth or medium or separately and used as an ingredient by at least partially reacting in acid or base with a base or an acid, respectively. When more than one pH modifiers are utilized, they can be added at the same time or at different times. In one embodiment, one or more acids and one or more bases are combined, resulting in a buffer. In one embodiment, media components, such as a carbon source or a nitrogen source serve as a pH modifier; suitable media components include those with high or low pH or those with buffering capacity. Exemplary media components include acid- or base-hydrolyzed plant polysaccharides having residual acid or base, ammonia fiber explosion (AFEX) treated plant material with residual ammonia, lactic acid, corn steep solids or liquor.

"Growth phase" is used herein to describe the type of cellular growth that occurs after the "Initiation phase" and before the "Stationary phase" and the "Death phase." The growth phase is sometimes referred to as the exponential phase or log phase or logarithmic phase.

The term "plant polysaccharide" as used herein has its ordinary meaning as known to those skilled in the art and can comprise one or more polymers of sugars and sugar derivatives as well as derivatives of sugar polymers and/or other polymeric materials that occur in plant matter. Exemplary plant polysaccharides include lignin, cellulose, starch, pectin, and hemicellulose. Others are chitin, sulfonated polysaccharides such as alginic acid, agarose, carrageenan, porphyran, furcelleran and funoran. Generally, the polysaccharide can have two or more sugar units or derivatives of sugar units. The sugar units and/or derivatives of sugar units can repeat in a regular pattern, or otherwise. The sugar units can be hexose units or pentose units, or combinations of these. The derivatives of sugar units can be sugar alcohols, sugar acids, amino sugars, etc. The polysaccharides can be linear, branched, cross-linked, or a mixture thereof. One type or class of polysaccharide can be cross-linked to another type or class of polysaccharide.

The term "saccharification" as used herein has its ordinary meaning as known to those skilled in the art and can include conversion of plant polysaccharides to lower molecular weight species that can be utilized by the organism at hand. For some organisms, this would include conversion to monosaccharides, disaccharides, trisaccharides, and oligosaccharides of up to about seven monomer units, as well as similar sized chains of sugar derivatives and combinations of sugars and sugar derivatives.

The terms "SSF" and "SHF" are known to those skilled in the art; SSF meaning simultaneous saccharification and fermentation, or the conversion from polysaccharides or oligosaccharides into monosaccharides at the same time and in the same fermentation vessel wherein monosaccharides are converted to another chemical product such as ethanol. "SHF" indicates a physical separation of the polymer hydrolysis or saccharification and fermentation processes.

The term "biomass" as used herein has its ordinary meaning as known to those skilled in the art and can include one or more biological materials that can be converted into a biofuel, chemical or other product. Biomass as used herein is synonymous with the term "feedstock" and includes corn syrup, molasses, silage, agricultural residues (corn stalks, grass, straw, grain hulls, bagasse, etc.), animal waste (manure from cattle, poultry, and hogs), Distillers Dried Solubles (DDS), Distillers Dried Grains (DDG), Condensed Distillers Solubles (CDS), Distillers Wet Grains (DWG), Distillers Dried Grains with Solubles (DDGS), woody materials (wood or bark, sawdust, timber slash, and mill scrap), municipal waste (waste paper, recycled toilet papers, yard clippings, etc.), and energy crops (poplars, willows, switchgrass, alfalfa, prairie bluestem, algae, including macroalgae, etc.). One exemplary source of biomass is plant matter. Plant matter can be, for example, woody plant matter, non-woody plant matter, cellulosic material, lignocellulosic material, hemicellulosic material, carbohydrates, pectin, starch, inulin, fructans, glucans, corn, sugar cane, grasses, switchgrass, sorghum, high biomass sorghum, bamboo, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, meat, fat, animal processing waste, and animal waste. "Feedstock" is frequently used to refer to biomass being used for a process, such as those described herein.

"Broth" is used herein to refer to inoculated medium at any stage of growth, including the point immediately after inoculation and the period after any or all cellular activity has ceased and can include the material after post-fermentation processing. It includes the entire contents of the combination of soluble and insoluble matter, suspended matter, cells and medium, as appropriate.

The term "productivity" as used herein has its ordinary meaning as known to those skilled in the art and can include the mass of a material of interest produced in a given time in a given volume. Units can be, for example, grams per liter-hour, or some other combination of mass, volume, and time. In fermentation, productivity is frequently used to characterize how fast a product can be made within a given fermentation volume. The volume can be referenced to the total volume of the fermentation vessel, the working volume of the fermentation vessel, or the actual volume of broth being fermented. The context of the phrase will indicate the meaning intended to one of skill in the art. Productivity is different from "titer" in that productivity includes a time term, and titer is analogous to concentration. Titer and Productivity can generally be measured at any time during the fermentation, such as at the beginning, the end, or at some intermediate time, with titer relating the amount of a particular material present or produced at the point in time of interest and the productivity relating the amount of a particular material produced per liter in a given amount of time. The amount of time used in the productivity determination can be from the beginning of the fermentation or from some other time, and go to the end of the fermentation, such as when no additional material is produced or when harvest occurs, or some other time as indicated by the context of the use of the term. "Overall productivity" refers to the productivity determined by utilizing the final titer and the overall fermentation time.

"Titer" refers to the amount of a particular material present in a fermentation broth. It is similar to concentration and can refer to the amount of material made by the organism in the broth from all fermentation cycles, or the amount of material made in the current fermentation cycle or over a given period of time, or the amount of material present from whatever source, such as produced by the organism or added to the broth. Frequently, the titer of soluble species will be referenced to the liquid portion of the broth, with insolubles removed, and the titer of insoluble species will be referenced to the total amount of broth with insoluble species being present, however, the titer of soluble species can be referenced to the total broth volume and the titer of insoluble species can be referenced to the liquid portion, with the context indicating the which system is used with both reference systems intended in some cases. Frequently, the value determined referenced to one system will be the same or a sufficient approximation of the value referenced to the other.

"Concentration" when referring to material in the broth or in solution generally refers to the amount of a material present from all sources, whether made by the organism or added to the broth or solution. Concentration can refer to soluble species or insoluble species, and is referenced to either the liquid portion of the broth or the total volume of the broth, as for "titer." When referring to a solution, such as "concentration of the sugar in solution", the term indicates increasing one or more components of the solution through evaporation, filtering, extraction, etc., by removal or reduction of a liquid portion.

The term "biocatalyst" as used herein has its ordinary meaning as known to those skilled in the art and can include one or more enzymes and/or microorganisms, including solutions, suspensions, and mixtures of enzymes and microorganisms. In some contexts this word will refer to the possible use of either enzymes or microorganisms to serve a particular function, in other contexts the word will refer to the combined use of the two, and in other contexts the word will refer to only one of the two. The context of the phrase will indicate the meaning intended to one of skill in the art. For example, a biocatalyst can be a fermenting microorganism.

"Pretreatment" or "pretreated" is used herein to refer to any mechanical, chemical, thermal, biochemical process or combination of these processes whether in a combined step or performed sequentially, that achieves disruption or expansion of the biomass so as to render the biomass more susceptible to attack by enzymes and/or microbes, and can include the enzymatic hydrolysis of released carbohydrate polymers or oligomers to monomers. In one embodiment, pretreatment includes removal or disruption of lignin so as to make the cellulose and hemicellulose polymers in the plant biomass more available to cellulolytic enzymes and/or microbes, for example, by treatment with acid or base. In one embodiment, pretreatment includes disruption or expansion of cellulosic and/or hemicellulosic material. In another embodiment, it can refer to starch release and/or enzymatic hydrolysis to glucose. Steam explosion, and ammonia fiber expansion (or explosion) (AFEX) are well known thermal/chemical techniques. Hydrolysis, including methods that utilize acids, bases, and/or enzymes can be used. Other thermal, chemical, biochemical, enzymatic techniques can also be used.

"Fed-batch" or "fed-batch fermentation" is used herein to include methods of culturing microorganisms where nutrients, other medium components, or biocatalysts (including, for example, enzymes, fresh organisms, extracellular broth, genetically modified plants and/or organisms, etc.) are supplied to the fermentor during cultivation, but culture broth is not harvested from the fermentor until the end of the fermentation, although it can also include "self seeding" or "partial harvest" techniques where a portion of the fermentor volume is harvested and then fresh medium is added to the remaining broth in the fermentor, with at least a portion of the inoculum being the broth that was left in the fermentor. During a fed-batch fermentation, the broth volume can increase, at least for a period, by adding medium or nutrients to the broth while fermentation organisms are present. Suitable nutrients which can be utilized include those that are soluble, insoluble, and partially soluble, including gasses, liquids and solids. In one embodiment, a fed-batch process is referred to with a phrase such as, "fed-batch with cell augmentation." This phrase can include an operation where nutrients and cells are added or one where cells with no substantial amount of nutrients are added. The more general phrase "fed-batch" encompasses these operations as well. The context where any of these phrases is used will indicate to one of skill in the art the techniques being considered.

"Sugar compounds" or "sugar streams" is used herein to indicate mostly monosaccharide sugars, dissolved, crystallized, evaporated, or partially dissolved, including but not limited to hexoses and pentoses; sugar alcohols; sugar acids; sugar amines; compounds containing two or more of these linked together directly or indirectly through covalent or ionic bonds; and mixtures thereof. Included within this description are disaccharides; trisaccharides; oligosaccharides; polysaccharides; and sugar chains, branched and/or linear, of any length. A sugar stream can consist of primarily or substantially C6 sugars, C5 sugars, or mixtures of both C6 and C5 sugars in varying ratios of said sugars. C6 sugars have a six-carbon molecular backbone and C5 sugars have a five-carbon molecular backbone.

"Crude sugar stream" is used herein to indicate a sugar stream that was produced by pretreating and hydrolyzing cellulose, hemicellulose, or lignocellulose from a biomass. A crude sugar stream has not been subjected to a purification, clean-up, or refining process. A crude sugar stream can be concentrated or a direct hydrolysis product.

"Originator sugar stream" or a "originator crude sugar stream" is used herein to indicate a sugar stream before the sugar stream was subjected to a purification, clean-up, or refining process. Therefore, a comparison of a refined sugar stream with an originator sugar stream is a comparison of a sugar stream before and after a purification, clean-up, or refining process.

"C5-rich" composition means that one or more steps have been taken to remove at least some of the C6 sugars originally in the composition. For example, a C5-rich composition can include no more than about 50% C6 sugars, nor more than about 40% C6 sugars, no more than about 30% C6 sugars, no more than about 20% C6 sugars, no more than about 10% C6 sugars, no more than about 5% C6 sugars, or it can include from about 2% to about 10% C6 sugars by weight. Likewise, a "C6-rich" composition is one in which at least some of the originally-present C5 sugars have been removed. For example, a C6-rich composition can include no more than about 50% C5 sugars, nor more than about 40% C5 sugars, no more than about 30% C5 sugars, no more than about 20% C5 sugars, no more than about 10% C5 sugars, no more than about 5% C5 sugars, or it can include from about 2% to about 10% C5 sugars by weight.

A "liquid" composition may contain solids and a "solids" composition may contain liquids. A liquid composition refers to a composition in which the material is primarily liquid, and a solids composition is one in which the material is primarily solid.

The terms "non-cellulosic" and "sugar- or starch-based" are used interchangeably and have the same meaning. For example "non-cellulosic fermentation process" is used interchangeably and means the same thing as "sugar- and starch-based fermentation process." Starch is a carbohydrate consisting of consisting of a large number of glucose units joined by glycosidic bonds. The glycosidic bonds are typically the easily hydrolysable alpha glycosidic bonds. This polysaccharide can be produced by all green plants as an energy store. There can be two types of starch molecules: the linear and helical amylose and the branched amylopectin, although amylase can also contain branches.

DESCRIPTION

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

Acid hydrolysis of lignocellulosic biomass to produce sugars can be costly and requires special equipment. The process, especially under high temperatures and pressure, can release structural carbohydrates in cellulosic biomass and can expose crystalline cellulose to enzymatic degradation. The hydrolyzed sugars produced through this pretreatment process themselves can be labile to the harsh hydrolysis conditions and can be degraded to unwanted or toxic byproducts. If exposed to acid too long, especially under high temperatures, the glucose derived from cellulose can degrade into hydroxymethylfurfural, which can be further degraded into levulinic acid and formic acid. Xylose, a hemicellulose sugar, can be degraded into furfural and further to tars and other degradation products.

Lignin is a complex polymer and the solubilization of lignin during pretreatment can produce various aromatic and phenolics. These lignin-derived compounds can be referred to as low molecular weight lignins.

For acid to completely hydrolyze the cellulose and hemicellulose in a lignocellulosic substrate, degradation of the desirable sugars and formation of the toxic byproducts may be unavoidable due to kinetic constraints. Too gentle a process, so that significant degradation of sugars is avoided, may not result in complete hydrolysis of substrate. Furthermore, the acid can be corrosive and can require special handling and equipment. Accordingly, in the last twenty years attention pretreatment has focused on enzymatic hydrolysis of cellulose with cellulase followed by fermentation of the resulting sugars to produce ethanol which in turn can be distilled to purify it sufficiently for fuel uses.

Cellulase is an enzyme complex that can include, for example, three different types of enzymes involved in the saccharification of cellulose. The cellulase enzyme complex produced by *Trichoderma reesei* QM 9414 contains the enzymes endoglucanase (E.C. 3.2.1.4), cellobiohydrolase (E.C.3.2.1.91) and 13-glucosidase (E.C.3.2.1.21). Gum et al, *Biochem. Biophys. Acta,* 446:370-86 (1976). The combined synergistic actions of these three enzymes in a mixed cellulose preparation can completely hydrolyze cellulose to D-glucose. However, cellulase may not be able to completely degrade the cellulose found in native, unpretreated lignocellulose. It appears that the hemicellulose and lignin can interfere with the access of the enzyme complex to the cellulose, probably due to their coating and binding of the cellulose fibers. Furthermore, lignin itself can bind cellulase thereby rendering it inactive or less effective for digesting cellulose. For example, raw ground hardwood can be only about 10 to 20% digestible into sugars using a cellulase preparation.

Feedstock and Pretreatment of Feedstock

In one embodiment, the feedstock (biomass) contains cellulosic, hemicellulosic, and/or lignocellulosic material. The feedstock can be derived from agricultural crops, crop residues, trees, woodchips, sawdust, paper, cardboard, grasses, algae, municipal waste and other sources.

Cellulose is a linear polymer of glucose where the glucose units are connected via β(1→4) linkages. Hemicellulose is a branched polymer of a number of sugar monomers including glucose, xylose, mannose, galactose, rhamnose and arabinose, and can have sugar acids such as mannuronic acid and galacturonic acid present as well. Lignin is a cross-linked, racemic macromolecule of mostly p-coumaryl alcohol, conferyl alcohol and sinapyl alcohol. These three polymers occur together in lignocellulosic materials in plant biomass. The different characteristics of the three polymers can make hydrolysis of the combination difficult as each polymer tends to shield the others from enzymatic attack.

In one embodiment, methods are provided for the pretreatment of feedstock used in the fermentation and production of the biofuels and chemicals. The pretreatment steps can include mechanical, thermal, pressure, chemical, thermochemical, and/or biochemical tests pretreatment prior to being used in a bioprocess for the production of fuels and chemicals, but untreated biomass material can be used in the process as well. Mechanical processes can reduce the particle size of the biomass material so that it can be more conveniently handled in the bioprocess and can increase the surface area of the feedstock to facilitate contact with chemicals/biochemicals/biocatalysts. Mechanical processes can also separate one type of biomass material from another. The biomass material can also be subjected to thermal and/or chemical pretreatments to render plant polymers more accessible. Multiple steps of treatment can also be used.

Mechanical processes include, are not limited to, washing, soaking, milling, size reduction, screening, shearing, size classification and density classification processes. Chemical processes include, but are not limited to, bleaching, oxidation, reduction, acid treatment, base treatment, sulfite treatment, acid sulfite treatment, basic sulfite treatment, ammonia treatment, and hydrolysis. Thermal processes include, but are not limited to, sterilization, ammonia fiber expansion or explosion ("AFEX"), steam explosion, holding at elevated temperatures, pressurized or unpressurized, in the presence or absence of water, and freezing. Biochemical processes include, but are not limited to, treatment with enzymes, including enzymes produced by genetically-modified plants, and treatment with microorganisms. Various enzymes that can be utilized include cellulase, amylase, β-glucosidase, xylanase, gluconase, and other polysaccharases; lysozyme; laccase, and other lignin-modifying enzymes; lipoxygenase, peroxidase, and other oxidative enzymes; proteases; and lipases. One or more of the mechanical, chemical, thermal, thermochemical, and biochemical processes can be combined or used separately. Such combined processes can also include those used in the production of paper, cellulose products, microcrystalline cellulose, and cellulosics and can include pulping, kraft pulping, acidic sulfite processing. The feedstock can be a side stream or waste stream from a facility that utilizes one or more of these processes on a biomass material, such as cellulosic, hemicellulosic or lignocellulosic material. Examples include paper plants, cellulosics plants, distillation plants, cotton processing plants, and microcrystalline cellulose plants. The feedstock can also include cellulose-containing or cellulosic containing waste materials. The feedstock can also be biomass materials, such as wood, grasses, corn, starch, or sugar, produced or harvested as an intended feedstock for production of ethanol or other products such as by biocatalysts.

In another embodiment, a method can utilize a pretreatment process disclosed in U.S. Patents and Patent Applications US20040152881, US20040171136, US20040168960, US20080121359, US20060069244, US20060188980, US20080176301, 5693296, 6262313, US20060024801, 5969189, 6043392, US20020038058, U.S. Pat. No. 5,865,898, U.S. Pat. No. 5,865,898, U.S. Pat. Nos. 6,478,965, 5,986,133, or US20080280338, each of which is incorporated by reference herein in its entirety In another embodiment, the AFEX process is be used for pretreatment of biomass. In a preferred embodiment, the AFEX process is used in the preparation of cellulosic, hemicellulosic or lignocellulosic materials for fermentation to ethanol or other products. The process generally includes combining the feedstock with ammonia, heating under pressure, and suddenly releasing the pressure. Water can be present in various amounts. The AFEX process has been the subject of numerous patents and publications.

In another embodiment, the pretreatment of biomass comprises the addition of calcium hydroxide to a biomass to render the biomass susceptible to degradation. Pretreatment comprises the addition of calcium hydroxide and water to the biomass to form a mixture, and maintaining the mixture at a relatively high temperature. Alternatively, an oxidizing agent, selected from the group consisting of oxygen and oxygen-containing gasses, can be added under pressure to the mixture. Examples of carbon hydroxide treatments are disclosed in U.S. Pat. No. 5,865,898 to Holtzapple and S. Kim and M. T. Holzapple, Bioresource Technology, 96, (2005) 1994, incorporated by reference herein in its entirety.

In one embodiment, pretreatment of biomass comprises dilute acid hydrolysis. Example of dilute acid hydrolysis treatment are disclosed in T. A. Lloyd and C. E Wyman, Bioresource Technology, (2005) 96, 1967), incorporated by reference herein in its entirety.

In another embodiment, pretreatment of biomass comprises pH controlled liquid hot water treatment. Examples of pH controlled liquid hot water treatments are disclosed in N. Mosier et al., Bioresource Technology, (2005) 96, 1986, incorporated by reference herein in its entirety.

In one embodiment, pretreatment of biomass comprises aqueous ammonia recycle process (ARP). Examples of aqueous ammonia recycle process are described in T. H. Kim and Y. Y. Lee, Bioresource Technology, (2005)96, 2007, incorporated by reference herein in its entirety.

In one embodiment, the above mentioned methods have two steps: a pretreatment step that leads to a wash stream, and an enzymatic hydrolysis step of pretreated-biomass that produces a hydrolysate stream. In the above methods, the pH at which the pretreatment step is carried out includes acid hydrolysis, hot water pretreatment, steam explosion or alkaline reagent based methods (AFEX, ARP, and lime pretreatments). Dilute acid and hot water treatment methods solubilize mostly hemicellulose, whereas methods employing alkaline reagents remove most lignin during the pretreatment step. As a result, the wash stream from the pretreatment step in the former methods contains mostly hemicellulose-based sugars, whereas this stream has mostly lignin for the high-pH methods. The subsequent enzymatic hydrolysis of the residual biomass leads to mixed sugars (C5 and C6) in the alkali based pretreatment methods, while glucose is the major product in the hydrolyzate from the low and neutral pH methods. In one embodiment, the treated material is additionally treated with catalase or another similar chemical, chelating agents, surfactants, and other compounds to remove impurities or toxic chemicals or further release polysaccharides.

In one embodiment, pretreatment of biomass comprises ionic liquid (IL) pretreatment. Biomass can be pretreated by incubation with an ionic liquid, followed by IL extraction with a wash solvent such as alcohol or water. The treated biomass can then be separated from the ionic liquid/wash-solvent solution by centrifugation or filtration, and sent to the saccharification reactor or vessel. Examples of ionic liquid pretreatment are disclosed in US publication No. 2008/0227162, incorporated herein by reference in its entirety.

In another embodiment, a method can utilize a pretreatment process disclosed in U.S. Pat. No. 4,600,590 to Dale, U.S. Pat. No. 4,644,060 to Chou, U.S. Pat. No. 5,037,663 to Dale. U.S. Pat. No. 5,171,592 to Holtzapple, et al., et al., U.S. Pat. No. 5,939,544 to Karstens, et al., U.S. Pat. No. 5,473,061 to Bredereck, et al., U.S. Pat. No. 6,416,621 to Karstens., U.S. Pat. No. 6,106,888 to Dale, et al., U.S. Pat. No. 6,176,176 to Dale, et al., PCT publication WO2008/020901 to Dale, et al., Felix, A., et al., Anim. Prod. 51, 47-61 (1990), Wais, A. C., Jr., et al., Journal of Animal Science, 35, No. 1, 109-112 (1972), which are incorporated herein by reference in their entireties.

Alteration of the pH of a pretreated feedstock can be accomplished by washing the feedstock (e.g., with water) one or more times to remove an alkaline or acidic substance, or other substance used or produced during pretreatment. Washing can comprise exposing the pretreated feedstock to an equal volume of water 2, 3, 4, 5, 6, 7, 8, 9, 10, 11, 12, 13, 14, 15, 16, 17, 18, 19, 20, 21, 22, 23, 24, 25 or more times. In another embodiment, a pH modifier can be added. For example, an acid, a buffer, or a material that reacts with other materials present can be added to modulate the pH of the feedstock. In one embodiment, more than one pH modifier can be used, such as one or more bases, one or more bases with one or more buffers, one or more acids, one or more acids with one or more buffers, or one or more buffers. When more than one pH modifiers are utilized, they can be added at the same time or at different times. Other non-limiting exemplary methods for neutralizing feedstocks treated with alkaline substances have been described, for example in U.S. Pat. Nos. 4,048,341; 4,182,780; and 5,693,296.

In one embodiment, one or more acids can be combined, resulting in a buffer. Suitable acids and buffers that can be used as pH modifiers include any liquid or gaseous acid that is compatible with the microorganism. Non-limiting examples include peroxyacetic acid, sulfuric acid, lactic acid, citric acid, phosphoric acid, and hydrochloric acid. In some instances, the pH can be lowered to neutral pH or acidic pH, for example a pH of 7.0, 6.5, 6.0, 5.5, 5.0, 4.5, 4.0, or lower. In some embodiments, the pH is lowered and/or maintained within a range of about pH 4.5 to about 7.1, or about 4.5 to about 6.9, or about pH 5.0 to about 6.3, or about pH 5.5 to about 6.3, or about pH 6.0 to about 6.5, or about pH 5.5 to about 6.9 or about pH 6.2 to about 6.7.

In another embodiment, biomass can be pre-treated at an elevated temperature and/or pressure. In one embodiment biomass is pre treated at a temperature range of 20° C. to 400° C. In another embodiment biomass is pretreated at a temperature of about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., 400° C. or higher. In another embodiment, elevated temperatures are provided by the use of steam, hot water, or hot gases. In one embodiment steam can be injected into a biomass containing vessel. In another embodiment the steam, hot water, or hot gas can be injected into a vessel jacket such that it heats, but does not directly contact the biomass.

In another embodiment, a biomass can be treated at an elevated pressure. In one embodiment biomass is pre treated at a pressure range of about 1 psi to about 30 psi. In another embodiment biomass is pre treated at a pressure or about 1 psi, 2 psi, 3 psi, 4 psi, 5 psi, 6 psi, 7 psi, 8 psi, 9 psi, 10 psi, 12 psi, 15 psi, 18 psi, 20 psi, 22 psi, 24 psi, 26 psi, 28 psi, 30 psi or more. In some embodiments, biomass can be treated with elevated pressures by the injection of steam into a biomass containing vessel. In one embodiment, the biomass can be treated to vacuum conditions prior or subsequent to alkaline or acid treatment or any other treatment methods provided herein.

In one embodiment alkaline or acid pretreated biomass is washed (e.g. with water (hot or cold) or other solvent such as alcohol (e.g. ethanol)), pH neutralized with an acid, base, or buffering agent (e.g. phosphate, citrate, borate, or carbonate salt) or dried prior to fermentation. In one embodiment, the drying step can be performed under vacuum to increase the rate of evaporation of water or other solvents. Alternatively, or additionally, the drying step can be performed at elevated temperatures such as about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C. or more.

In one embodiment of the present invention, the pretreatment step includes a step of solids recovery. The solids recovery step can be during or after pretreatment (e.g., acid or alkali pretreatment), or before the drying step. In one embodiment, the solids recovery step provided by the methods of the present invention includes the use of a sieve, filter, screen, or a membrane for separating the liquid and solids fractions. In one embodiment a suitable sieve pore diameter size ranges from about 0.001 microns to 8 mm, such as about 0.005 microns to 3 mm or about 0.01 microns to 1 mm. In one embodiment a sieve pore size has a pore diameter of about 0.01 microns, 0.02 microns, 0.05 microns, 0.1 microns, 0.5 microns, 1 micron, 2 microns, 4 microns, 5 microns, 10 microns, 20 microns, 25 microns, 50 microns, 75 microns, 100 microns, 125 microns, 150 microns, 200 microns, 250 microns, 300 microns, 400 microns, 500 microns, 750 microns, 1 mm or more. In one embodiment, biomass (e.g. corn stover) is processed or pretreated prior to fermentation. In one embodiment a method of pre-treatment includes but is not limited to, biomass particle size reduction, such as for example shredding, milling, chipping, crushing, grinding, or pulverizing. In one embodiment, biomass particle size reduction can include size separation methods such as sieving, or other suitable methods known in the art to separate materials based on size. In one embodiment size separation can provide for enhanced yields. In one embodiment, separation of finely shredded biomass (e.g. particles smaller than about 8 mm in diameter, such as, 8, 7.9, 7.7, 7.5, 7.3, 7, 6.9, 6.7, 6.5, 6.3, 6, 5.9, 5.7, 5.5, 5.3, 5, 4.9, 4.7, 4.5, 4.3, 4, 3.9, 3.7, 3.5, 3.3, 3, 2.9, 2.7, 2.5, 2.3, 2, 1.9, 1.7, 1.5, 1.3, 1, 0.9, 0.8, 0.7, 0.6, 0.5, 0.4, 0.3, 0.2, or 0.1 mm) from larger particles allows the recycling of the larger particles back into the size reduction process, thereby increasing the final yield of processed biomass. In one embodiment, a fermentative mixture is provided which comprises a pretreated lignocellulosic feedstock comprising less than about 50% of a lignin component present in the feedstock prior to pretreatment and comprising more than about 60% of a hemicellulose component present in the feedstock prior to pretreatment; and a microorganism capable of fermenting a five-carbon sugar, such as xylose, arabinose or a combination thereof, and a six-carbon sugar, such as glucose, galactose, mannose or a combination thereof. In some instances, pretreatment of the lignocellulosic feedstock comprises adding an alkaline substance which raises the pH to an alkaline level, for example NaOH. In one embodiment, NaOH is added at a concentration of about 0.5% to about 2% by weight of the feedstock. In one embodiment, pretreatment also comprises addition of a chelating agent.

Hydrolysis

In one embodiment, the biomass hydrolyzing unit provides useful advantages for the conversion of biomass to biofuels and chemical products. One advantage of this unit is its ability to produce monomeric sugars from multiple types of biomass, including mixtures of different biomass materials, and is capable of hydrolyzing polysaccharides and higher molecular weight saccharides to lower molecular weight saccharides. In one embodiment, the hydrolyzing unit utilizes a pretreatment process and a hydrolytic enzyme which facilitates the production of a sugar stream containing a concentration of a monomeric sugar or several monomeric sugars derived from cellulosic and/or hemicellulosic polymers. Examples of biomass material that can be pretreated and hydrolyzed to manufacture sugar monomers include, but are not limited to, cellulosic, hemicellulosic, lignocellulosic materials; pectins; starches; wood; paper; agricultural products; forest waste; tree waste; tree bark; leaves; grasses; sawgrass; woody plant matter; non-woody plant matter; carbohydrates; starch; inulin; fructans; glucans; corn; sugar cane; sorghum, other grasses; bamboo, algae, and material derived from these materials. This ability to use a very wide range of pretreatment methods and hydrolytic enzymes gives distinct advantages in biomass fermentations. Various pretreatment conditions and enzyme hydrolysis can enhance the extraction of sugars from biomass, resulting in higher yields, higher productivity, greater product selectivity, and/or greater conversion efficiency.

In one embodiment, the enzyme treatment is used to hydrolyze various higher saccharides (higher molecular weight) present in biomass to lower saccharides (lower molecular weight), such as in preparation for fermentation by biocatalysts such as yeasts to produce ethanol, hydrogen, or other chemicals such as organic acids including succinic acid, formic acid, acetic acid, and lactic acid. These enzymes and/or the hydrolysate can be used in fermentations to produce various products including fuels, and other chemicals.

In one example, the process for converting biomass material into ethanol includes pretreating the biomass material (e.g., "feedstock"), hydrolyzing the pretreated biomass to convert polysaccharides to oligosaccharides, further hydrolyzing the oligosaccharides to monosaccharides, and converting the monosaccharides to biofuels and chemical products. Enzymes such as cellulases, polysaccharases, lipases, proteases, ligninases, and hemicellulases, help produce the monosaccharides can be used in the biosynthesis of fermentation end-products. Biomass material that can be utilized includes woody plant matter, non-woody plant matter, cellulosic material, lignocellulosic material, hemicellulosic material, carbohydrates, pectin, starch, inulin, fructans, glucans, corn, algae, sugarcane, other grasses, switchgrass, bagasse, wheat straw, barley straw, rice straw, corncobs, bamboo, citrus peels, sorghum, high biomass sorghum, seed hulls, and material derived from these. The final product can then be separated and/or purified, as indicated by the properties for the desired final product. In some instances, compounds related to sugars such as sugar alcohols or sugar acids can be utilized as well.

Chemicals used in the methods of the present invention are readily available and can be purchased from a commercial supplier, such as Sigma-Aldrich. Additionally, commercial enzyme cocktails (e.g. Accellerase™ 1000, CelluSeb-TL, CelluSeb-TS, Cellic™ CTec, STARGEN™, Maxalig™, Spezyme.R™, Distillase.R™, G-Zyme.R™, Fermenzyme.R™ Fermgen™, GC 212, or Optimash™) or any other commercial enzyme cocktail can be purchased from vendors such as Specialty Enzymes & Biochemicals Co., Genencor, or Novozymes. Alternatively, enzyme cocktails can be prepared by growing one or more organisms such as for example a fungi (e.g. a *Trichoderma*, a *Saccharomyces*, a *Pichia*, a White Rot Fungus etc.), a bacteria (e.g. a *Clostridium*, or a coliform bacterium, a *Zymomonas* bacterium, *Sacharophagus degradans* etc.) in a suitable medium and harvesting enzymes produced therefrom. In some embodiments, the harvesting can include one or more steps of purification of enzymes.

In one embodiment, treatment of biomass comprises enzyme hydrolysis. In one embodiment a biomass is treated with an enzyme or a mixture of enzymes, e.g., endonucleases, exonucleases, cellobiohydrolases, cellulase, beta-glucosidases, glycoside hydrolases, glycosyltransferases, lyases, esterases and proteins containing carbohydrate-binding modules. In one embodiment, the enzyme or mixture of enzymes is one or more individual enzymes with distinct activities. In another embodiment, the enzyme or mixture of enzymes can be enzyme domains with a particular catalytic activity. For example, an enzyme with multiple activities can have multiple enzyme domains, including for example glycoside hydrolases, glycosyltransferases, lyases and/or esterases catalytic domains.

In one embodiment, enzymes that degrade polysaccharides are used for the hydrolysis of biomass and can include enzymes that degrade cellulose, namely, cellulases. Examples of some cellulases include endocellulases and exo-cellulases that hydrolyze beta-1,4-glucosidic bonds.

In one embodiment, enzymes that degrade polysaccharides are used for the hydrolysis of biomass and can include enzymes that have the ability to degrade hemicellulose, namely, hemicellulases. Hemicellulose can be a major component of plant biomass and can contain a mixture of pentoses and hexoses, for example, D-xylopyranose, L-arabinofuranose, D-mannopyranose, Dglucopyranose, D-galactopyranose, D-glucopyranosyluronic acid and other sugars. In one embodiment, enzymes that degrade polysaccharides are used for the hydrolysis of biomass and can include enzymes that have the ability to degrade pectin, namely, pectinases. In plant cell walls, the cross-linked cellulose network can be embedded in a matrix of pectins that can be covalently cross-linked toxyloglucans and certain structural proteins. Pectin can comprise homogalacturonan (HG) or rhamnogalacturonan (RH).

In one embodiment, hydrolysis of biomass includes enzymes that can hydrolyze starch. Enzymes that hydrolyze starch include alpha-amylase, glucoamylase, beta-amylase, exo-alpha-1,4-glucanase, and pullulanase.

In one embodiment, hydrolysis of biomass comprises hydrolases that can include enzymes that hydrolyze chitin. In another embodiment, hydrolases can include enzymes that hydrolyze lichen, namely, lichenase.

In one embodiment, after pretreatment and/or hydrolysis by any of the above methods the feedstock contains cellulose, hemicellulose, soluble oligomers, simple sugars, lignin, volatiles and ash. The parameters of the hydrolysis can be changed to vary the concentration of the components of the pretreated feedstock. For example, in one embodiment a hydrolysis is chosen so that the concentration of soluble C5 saccharides is high and the concentration of lignin is low after hydrolysis. Examples of parameters of the hydrolysis include temperature, pressure, time, concentration, composition and pH.

In one embodiment, the parameters of the pretreatment and hydrolysis are changed to vary the concentration of the components of the pretreated feedstock such that concentration of the components in the pretreated and hydrolyzed feedstock is optimal for fermentation with a microbe such as a yeast or bacterium microbe.

In one embodiment, the parameters of the pretreatment are changed to encourage the release of the components of a genetically modified feedstock such as enzymes stored within a vacuole to increase or complement the enzymes synthesized by biocatalyst to produce optimal release of the fermentable components during hydrolysis and fermentation.

In one embodiment, the parameters of the pretreatment and hydrolysis are changed such that concentration of accessible cellulose in the pretreated feedstock is 1%, 5%, 10%, 12%, 13%, 14%, 15%, 16%, 17%, 19%, 20%, 30%, 40% or 50%. In one embodiment, the parameters of the pretreatment are changed such that concentration of accessible cellulose in the pretreated feedstock is 5% to 30%. In one embodiment, the parameters of the pretreatment are changed such that concentration of accessible cellulose in the pretreated feedstock is 10% to 20%.

In one embodiment, the parameters of the pretreatment are changed such that concentration of hemicellulose in the pretreated feedstock is 1%, 5%, 10%, 12%, 13%, 14%, 15%, 16%, 17%, 19%, 20%, 21%, 22%, 23%, 24%, 25%, 26%, 27%, 28%, 29%, 30%, 40% or 50%. In one embodiment, the parameters of the pretreatment are changed such that concentration of hemicellulose in the pretreated feedstock is 5% to 40%. In one embodiment, the parameters of the pretreatment are changed such that concentration of hemicellulose in the pretreated feedstock is 10% to 30%.

In one embodiment, the parameters of the pretreatment and hydrolysis are changed such that concentration of soluble oligomers in the pretreated feedstock is 1%, 10%, 15%, 20%, 25%, 30%, 35%, 40%, 45%, 50%, 55%, 60%, 65%, 70%, 75%, 80%, 85%, 90%, 95%, or 99%. Examples of soluble oligomers include, but are not limited to, cellobiose and xylobiose. In one embodiment, the parameters of the pretreatment are changed such that concentration of soluble oligomers in the pretreated feedstock is 30% to 90%. In one embodiment, the parameters of the pretreatment and/or hydrolysis are changed such that concentration of soluble oligomers in the pretreated feedstock is 45% to 80%.

In one embodiment, the parameters of the pretreatment and hydrolysis are changed such that concentration of simple sugars in the pretreated feedstock is 1%, 5%, 10%, 12%, 13%, 14%, 15%, 16%, 17%, 19%, 20%, 30%, 40% or 50%. In one embodiment, the parameters of the pretreatment and hydrolysis are changed such that concentration of simple sugars in the pretreated feedstock is 0% to 20%. In one embodiment, the parameters of the pretreatment and hydrolysis are changed such that concentration of simple sugars in the pretreated feedstock is 0% to 5%. Examples of simple sugars include, but are not limited to, C5 and C6 monomers and dimers.

In one embodiment, the parameters of the pretreatment are changed such that concentration of lignin in the pretreated and/or hydrolyzed feedstock is 1%, 5%, 10%, 12%, 13%, 14%, 15%, 16%, 17%, 19%, 20%, 30%, 40% or 50%. In one embodiment, the parameters of the pretreatment and/or hydrolysis are changed such that concentration of lignin in the pretreated feedstock is 0% to 20%. In one embodiment, the parameters of the pretreatment and/or hydrolysis are changed such that concentration of lignin in the pretreated feedstock is 0% to 5%. In one embodiment, the parameters of the pretreatment and hydrolysis are changed such that concentration of lignin in the pretreated and/or hydrolyzed feedstock is less than 1% to 2%. In one embodiment, the parameters of the pretreatment and/or hydrolysis are changed such that the concentration of phenolics is minimized.

In one embodiment, the parameters of the pretreatment and/or hydrolysis are changed such that concentration of furfural and low molecular weight lignin in the pretreated and/or hydrolyzed feedstock is less than 10%, 9%, 8%, 7%, 6%, 5%, 4%, 3%, 2%, or 1%. In one embodiment, the parameters of the pretreatment and/or hydrolysis are changed such that concentration of furfural and low molecular weight lignin in the pretreated and/or hydrolyzed feedstock is less than 1% to 2%.

In one embodiment, the parameters of the pretreatment and/or hydrolysis are changed such that the concentration of simple sugars is at least 75% to 85%, and the concentration of lignin is 0% to 5% and the concentration of furfural and low molecular weight lignin in the pretreated feedstock is less than 1% to 2%.

In one embodiment, the parameters of the pretreatment and/or hydrolysis are changed to obtain a high concentration of hemicellulose and a low concentration of lignin. In one embodiment, the parameters of the pretreatment and/or hydrolysis are changed to obtain a high concentration of hemicellulose and a low concentration of lignin such that concentration of the components in the pretreated stock is optimal for fermentation with a microbe such as biocatalyst.

In one embodiment, more than one of these steps can occur at any given time. For example, hydrolysis of the pretreated feedstock and hydrolysis of the oligosaccharides can occur simultaneously, and one or more of these can occur simultaneously to the conversion of monosaccharides to a fuel or chemical.

In another embodiment, an enzyme can directly convert the polysaccharide to monosaccharides. In some instances, an enzyme can hydrolyze the polysaccharide to oligosaccharides and the enzyme or another enzyme can hydrolyze the oligosaccharides to monosaccharides.

In another embodiment, the enzymes can be added to the fermentation or they can be produced by microorganisms present in the fermentation. In one embodiment, the microorganism present in the fermentation produces some enzymes. In another embodiment, enzymes are produced separately and added to the fermentation.

For the overall conversion of pretreated biomass to final product to occur at high rates, it is generally necessary for each of the necessary enzymes for each conversion step to be present with sufficiently high activity. If one of these enzymes is missing or is present in insufficient quantities, the production rate of an end product will be reduced. The production rate can also be reduced if the microorganisms responsible for the conversion of monosaccharides to product only slowly take up monosaccharides and/or have only limited capability for translocation of the monosaccharides and intermediates produced during the conversion to end product. Additions of fractions obtained from pretreatment and/or pretreatment and hydrolysis can increase initial or overall growth rates. In another embodiment, oligomers are taken up slowly by a biocatalyst, necessitating an almost complete conversion of polysaccharides and oligomers to monomeric sugars.

In another embodiment, the enzymes of the method are produced by a biocatalyst, including a range of hydrolytic enzymes suitable for the biomass materials used in the fermentation methods. In one embodiment, a biocatalyst is grown under conditions appropriate to induce and/or promote production of the enzymes needed for the saccharification of the polysaccharide present. The production of these enzymes can occur in a separate vessel, such as a seed fermentation vessel or other fermentation vessel, or in the production fermentation vessel where ethanol production occurs. When the enzymes are produced in a separate vessel, they can, for example, be transferred to the production fermentation vessel along with the cells, or as a relatively cell free solution liquid containing the intercellular medium with the enzymes. When the enzymes are produced in a separate vessel, they can also be dried and/or purified prior to adding them to the hydrolysis or the production fermentation vessel. The conditions appropriate for production of the enzymes are frequently managed by growing the cells in a medium that includes the biomass that the cells will be expected to hydrolyze in subsequent fermentation steps. Additional medium components, such as salt supplements, growth factors, and cofactors including, but not limited to phytate, amino acids, and peptides can also assist in the production of the enzymes utilized by the microorganism in the production of the desired products.

Biofuel Plant and Process of Producing Biofuel:

Large Scale Fuel and Chemical Production from Biomass

Generally, there are several basic approaches to producing fuels and chemical end-products from biomass on a large scale utilizing of microbial cells. In the one method, one first pretreats and hydrolyzes a biomass material that includes high molecular weight carbohydrates to lower molecular weight carbohydrates, and then ferments the lower molecular weight carbohydrates utilizing of microbial cells to produce fuel or other products. In the second method, one treats the biomass material itself using mechanical, chemical and/or enzymatic methods. In all methods, depending on the type of biomass and its physical manifestation, one of the processes can comprise a milling of the carbonaceous material, via wet or dry milling, to reduce the material in size and increase the surface to volume ratio (physical modification).

In one embodiment, hydrolysis can be accomplished using acids, e.g., Bronsted acids (e.g., sulfuric or hydrochloric acid), bases, e.g., sodium hydroxide, hydrothermal processes, ammonia fiber explosion processes ("AFEX"), lime processes, enzymes, or combination of these. Hydrogen, and other end products of the fermentation can be captured and purified if desired, or disposed of, e.g., by burning. For example, the hydrogen gas can be flared, or used as an energy source in the process, e.g., to drive a steam boiler, e.g., by burning. Hydrolysis and/or steam treatment of the biomass can, e.g., increase porosity and/or surface area of the biomass, often leaving the cellulosic materials more exposed to the biocatalyst cells, which can increase fermentation rate and yield. Removal of lignin can, e.g., provide a combustible fuel for driving a boiler, and can also, e.g., increase porosity and/or surface area of the biomass, often increasing fermentation rate and yield. Generally, in any of the these embodiments, the initial concentration of the carbohydrates in the medium is greater than 20 mM, e.g., greater than 30 mM, 50 mM, 75 mM, 100 mM, 150 mM, 200 mM, or even greater than 500 mM.

Biomass Processing Plant and Process of Producing Products from Biomass

In one aspect, a fuel or chemical plant that includes a pretreatment unit to prepare biomass for improved exposure and biopolymer separation, a hydrolysis unit configured to hydrolyze a biomass material that includes a high molecular weight carbohydrate, and one or more product recovery system(s) to isolate a product or products and associated by-products and co-products is provided. In another aspect, methods of purifying lower molecular weight carbohydrate from solid byproducts and/or toxic impurities are provided.

In another aspect, methods of making a product or products that include combining biocatalyst cells of a microorganism and a biomass feed in a medium wherein the biomass feed contains lower molecular weight carbohydrates and unseparated solids and/or other liquids from pretreatment and hydrolysis, and fermenting the biomass material under conditions and for a time sufficient to produce a biofuel, chemical product or fermentive end-products, e.g. ethanol, propanol, hydrogen, succinic acid, lignin, terpenoids, and the like as described above, is provided.

In another aspect, products made by any of the processes described herein are also provided herein.

FIG. 1 is an example of a method for producing sugar streams from biomass by first treating biomass with an acid at elevated temperature and pressure in a hydrolysis unit. The biomass may first be heated by addition of hot water or steam. The biomass may be acidified by bubbling gaseous sulfur dioxide through the biomass that is suspended in water, or by adding a strong acid, e.g., sulfuric, hydrochloric, or nitric acid with or without preheating/presteaming/water addition. Weaker acids or organic acids, such as carbonic, oxalic, malic, and the like can also be used. During the acidification, the pH is maintained at a low level, e.g., below about 5. The temperature and pressure may be elevated after acid addition. In addition to the acid already in the acidification unit, optionally, a metal salt such as ferrous sulfate, ferric sulfate, ferric chloride, aluminum sulfate, aluminum chloride, magnesium sulfate, or mixtures of these can be added to aid in the acid hydrolysis of the biomass. The acid-impregnated biomass is fed into the hydrolysis section of the pretreatment unit. Steam is injected into the hydrolysis portion of the pretreatment unit to directly contact and heat the biomass to the desired temperature. The temperature of the biomass after steam addition is, e.g., from about 130° C. to 220° C. The acid hydrolysate is then discharged into the flash tank portion of the pretreatment unit, and is held in the tank for a period of time to further hydrolyze the biomass, e.g., into oligosaccharides and monomeric sugars. Other methods can also be used to further break down biomass. Alternatively, the biomass can be subject to discharge through a pressure lock for any high-pressure pretreatment process, or through the use of a sonic nozzle. Hydrolysate is then discharged from the pretreatment reactor, with or without the addition of water, e.g., at solids concentrations from about 10% to about 60%.

After physical hydrolysis pretreatment, the biomass may be dewatered and/or washed with a quantity of water, e.g. by squeezing or by centrifugation, or by filtration using, e.g. a countercurrent extractor, wash press, filter press, pressure filter, a screw conveyor extractor, or a vacuum belt extractor to remove acidified fluid. The acidified fluid, with or without further treatment, e.g. addition of alkali (e.g. lime) and or ammonia (e.g. ammonium phosphate), can be re-used, e.g., in the acidification portion of the pretreatment unit, or added to the fermentation, or collected for other use/treatment. Products may be derived from treatment of the acidified fluid, e.g., gypsum or ammonium phosphate.

Wash fluids can be collected to concentrate the C5 saccharides in the wash stream. At such a point, the solids can be separated from the C5 stream and the C5 stream further purified through the use of carbon filtration.

Enzymes or a mixture of enzymes can be added during pretreatment to hydrolyze, e.g. endoglucanases, exoglucanases, cellobiohydrolases (CBH), beta-glucosidases, glycoside hydrolases, glycosyltransferases, alphyamylases, chitinases, pectinases, lyases, and esterases active against components of cellulose, hemicelluloses, pectin, and starch, in the hydrolysis of high molecular weight components. If the C5 saccharides are not collected separately, they are included in the enzymatic hydrolysis of the stream. Thus enzymatic hydrolysis can produce a fairly pure C6 stream or a mixed C5 and C6 stream. Solids are removed and the C6 or the mixed stream is then refined through activated carbon treatment. If the sugar stream is not concentrated, it can be further concentrated, usually through evaporation, prior to activated carbon treatment. The carbon is removed by any separation means, filtration, filter press, centrifugation or the like, and the resulting refined sugar stream collected or further treated, depending on the intended use of the sugar stream.

A fermentor, attached or at a separate site, can be fed with hydrolyzed biomass, any liquid fraction from biomass pretreatment, an active seed culture of a biocatalyst, such as a yeast, if desired a co-fermenting microbe, e.g., another yeast or $E.\ coli$, and, if required, nutrients to promote growth of the biocatalyst or other microbes. Alternatively, the pretreated biomass or liquid fraction can be split into multiple fermentors, each containing a different strain of a biocatalyst and/or other microbes, and each operating under specific physical conditions. Fermentation is allowed to proceed for a period of time, e.g., from about 1 to about 150 hours, while maintaining a temperature of, e.g., from about 25° C. to about 50° C. Gas produced during the fermentation is swept from fermentor and is discharged, collected, or flared with or without additional processing, e.g. hydrogen gas may be collected and used as a power source or purified as a co-product.

In another aspect, methods of making a fuel or fuels that include combining one or more biocatalyst and a lignocellulosic material (and/or other biomass material) in a medium, adding a lignin fraction from pretreatment, and fermenting the lignocellulosic material under conditions and for a time sufficient to produce a fuel or fuels, e.g., ethanol, propanol and/or hydrogen or another chemical compound is provided herein.

Refining Sugar Streams with Activated Carbon

Activated carbon is a form of carbon that has been reduced in particle size and its surface is covered in low volume pores which increase the surface area for absorption. There are many types of activated carbon used in industry including powdered activated carbon (PAC) and granular activated carbon (GAC). Disclosed herein are methods and systems for refining sugar streams produced from the pretreatment and/or hydrolysis of cellulosic, hemicellulosic, or lignocellulosic material using activated carbon. The methods disclosed herein can remove inhibitors produced during the pretreatment and/or hydrolysis (e.g., HMF, furfural, etc.), de-color the sugar streams, remove aromatic and phenolic compounds, or a combination thereof. The methods disclosed herein can be used on sugar streams having a high concentration of sugar (e.g., ≥15% w/v). The methods disclosed herein can minimize the loss of sugars.

As disclosed herein, heating the activated carbon and contacting a sugar stream with the heated activated carbon can improve the refining process. For example, heated carbon can be more effective in color removal. Heated carbon can be more effective in removal of inhibitors and/or aromatic and phenolic compounds. The benefits of heated carbon can enable the refinement of higher concentration sugar streams.

As disclosed herein, acidifying a sugar stream before contacting the sugar stream with activated carbon can improve the purification process. For example, acidifying the sugar stream can result in more effective color removal, more effected inhibitor reduction, more effective phenolic and aromatic compound removal, or a combination thereof. Acidifying the sugar stream can reduce the loss of sugars during the refinement process with activated carbon.

Diatomaceous earth can be used in the refinement process with activated carbon. Diatomaceous earth can facilitate removal of activated carbon from the refined sugar stream. For example, diatomaceous earth can be included in a column containing activated carbon. Diatomaceous earth can be used to filter a mixture of activated carbon and a sugar stream. Diatomaceous earth can be added to a mixture of activated carbon and a sugar stream to improve removal by centrifugal force or by gravitational settling.

The following embodiments are provided:

Embodiment Numbers

1. A method of refining a sugar stream, the method comprising: (a) heating activated carbon to a temperature of from about 100° C. to about 300° C. to produce heat activated carbon; (b) contacting the sugar stream with the heat activated carbon for a sufficient time to produce a refined sugar stream, wherein the heat activated carbon is at a temperature greater than the sugar stream.

2. A method of refining a sugar stream, the method comprising: (a) acidifying the sugar stream to a pH of from about 1 to about 4 by adding an acid to produce an acidified sugar stream; and (b) contacting the acidified sugar stream with activated carbon for a sufficient time to produce a refined sugar stream.

3. The method of embodiment 2, further comprising heating the activated carbon to a temperature of from about 100° C. to about 300° C. to produce heat activated carbon, wherein the contacting is performed with heat activated carbon, and wherein the heat activated carbon is at a temperature greater than the sugar stream.

4. A method of producing a refined sugar stream, the method comprising: (a) pretreating or hydrolyzing a biomass comprising cellulosic, hemicellulosic, or lignocellulosic material to produce a sugar stream, wherein the sugar stream has a total sugar concentration of about 15% or greater; and (b) contacting the sugar stream with activated carbon for a sufficient time to produce the refined sugar stream.

5. The method of embodiment 4, further comprising heating the activated carbon to a temperature of from about 100° C. to about 300° C. to produce heat activated carbon, wherein the contacting is performed with heat activated carbon, wherein the heat activated carbon is at a temperature greater than the sugar stream.

6. The method of embodiment 4, further comprising acidifying the sugar stream to a pH of from about 1 to about 4 by adding an acid to produce an acidified sugar stream, wherein contacting is performed with the acidified sugar stream.

7. The method of embodiment 4, further comprising heating the activated carbon to a temperature of from about 100° C. to about 300° C. to produce heat activated carbon and acidifying the sugar stream to a pH of from about 1 to about 4 by adding an acid to produce an acidified sugar stream, wherein contacting is performed with heat activated carbon and the acidified sugar stream, wherein the heat activated carbon is at a temperature greater than the acidified sugar stream.

8. A method of refining a sugar stream, the method comprising: (a) heating activated carbon to produce heat activated carbon; (b) storing the heat activated carbon in a non-oxidizing environment; and (c) contacting the sugar stream with the heat activated carbon for a sufficient time to produce a refined sugar stream.

9. The method of embodiment 8, further comprising acidifying the sugar stream to a pH of from about 1 to about 4 by adding an acid to produce an acidified sugar stream, wherein contacting is performed with the acidified sugar stream.

10. The method of embodiment 8, further comprising pretreating or hydrolyzing a biomass comprising cellulosic, hemicellulosic, or lignocellulosic material to produce the sugar stream.

Also provided are refined sugar streams produced by the methods of any one of embodiments 1-10.

The sugar stream is a liquid. The activated carbon is a solid.

The methods disclosed herein can be performed without significant loss of sugars due to adsorption by the activated carbon. For example, the activated carbon can adsorb less than about: 25%, 20%, 15%, 10%, 5%, 4%, 3%, 2%, or 1% of the total sugars in the sugar stream during contacting. In some embodiments, the activated carbon adsorbs less than about 20% of the sugars in the sugar stream during contacting. In some embodiments, the activated carbon adsorbs less than about 10% of the sugars in the sugar stream during contacting.

The methods disclosed herein can remove one or more inhibitors from a sugar stream. The inhibitors can be produced during pretreatment or hydrolysis of biomass comprising cellulosic, hemicellulosic, or lignocellulosic material. In some embodiments, the sugar stream comprises one or more inhibitors. In some embodiments, the one or more inhibitors comprise furfural, hydroxymethylfurfural, or a combination thereof. Contacting the sugar stream with activated carbon can remove, for example, at least about: 30%, 40%, 50%, 60%, 70%, 80%, 85%, 90%, 95%, or more of at least one of the inhibitors. In some embodiments, contacting the sugar stream with activated carbon removes about 70% or more of at least one of the inhibitors from the sugar stream. In some embodiments, the sugar stream with activated carbon removes about 80% or more of at least one of the inhibitors.

The methods disclosed herein can de-colorize sugar streams. For example, contacting a sugar stream with activated carbon according to the methods disclosed herein can increase the transparency of the sugar stream by at least about: 20%, 30%, 40%, 50%, 60%, 70%, 80%, 90%, 95%, 96%, 97%, 98%, or more. The transparency of the sugar stream can be measured, for example, using a spectrophotometer. The transparency of the sugar stream can be measured using 600 nm light. In some embodiments, contacting the sugar stream with activated carbon increases the transparency of the sugar stream by about 50% or more. In some embodiments, the transparency is increased by 75% or more.

Sugar streams produced by the pretreatment or hydrolysis of biomass comprising cellulosic, hemicellulosic, or lignocellulosic material can comprise one or more aromatic or phenolic compounds. Contacting a sugar stream with activated carbon according to the methods disclosed herein can remove at least about: 20%, 30%, 40%, 50%, 60%, 70%, 80%, 90%, 95%, 96%, 97%, 98%, or more of at least one of the aromatic or phenolic compounds. In some embodiments, contacting the sugar stream with activated carbon removes about 30% or more of at least one of the aromatic or phenolic compounds from the sugar stream. In some embodiments, contacting the sugar stream with activated carbon removes about 50% or more of at least one of the aromatic or phenolic compounds. In some embodiments, contacting the sugar stream with activated carbon removes about 70% or more of at least one of the aromatic or phenolic compounds.

Heating the activated carbon can be performed at a temperature of, for example, about: 150° C. to 900° C., 150° C. to 750° C., 150° C. to 500° C., 150° C. to 400° C., 150° C. to 300° C., 150° C. to 250° C., 150° C. to 225° C., 150° C. to 200° C., 150° C. to 175° C., 175° C. to 750° C., 175° C. to 500° C., 175° C. to 400° C., 175° C. to 300° C., 175° C. to 250° C., 175° C. to 225° C., 175° C. to 200° C., 200° C. to 500° C., 200° C. to 400° C., 200° C. to 300° C., 200° C. to 250° C., or 200° C. to 225° C. Heating the activated carbon can be performed at a temperature of, for example, about: 150° C. 160° C., 170° C., 180° C., 190° C., 210° C., 220° C., 230° C., 240° C., 260° C., 270° C., 280° C., 290° C., 300° C., 350° C., 400° C., 450° C., 500° C., 550° C., 600° C., 700° C., 800° C., or 900° C. In some embodiments, heating the activated carbon is to a temperature of from about 150° C. to about 250° C. In some embodiments, heating the activated carbon is to a temperature of from about 175° C. to about 225° C. In some embodiments, heating the activated carbon is to a temperature of about 200° C.

Heating the activated carbon can be performed, for example, for a time of about 1 hour to about 48 hours, about 1 hour to about 36 hours, about 1 hour to about 24 hours, about 1 hour to about 18 hours, about 1 hour to about 12 hours, about 1 hour to about 6 hours, about 2 hours, about 3 hours, about 4 hours, about 6 hours, about 7 hours, about 8 hours, about 9 hours, about 10 hours, about 11 hours, about 13 hours, about 14 hours, about 15 hours, about 17 hours, about 19 hours, about 20 hours, about 21 hours, about 22 hours, or about 23 hours. In some embodiments, heating the activated carbon is for a time of from about 1 hour to about 48 hours. In some embodiments, heating the activated carbon is for a time of from about 4 hours to about 24 hours.

In some embodiments, the temperature of the heat activated carbon during contacting is greater than room temperature. In some embodiments, the temperature of the heat activated carbon during contacting is about 65° C. or greater. In some embodiments, the temperature of the heat activated carbon during contacting is about 100° C. or greater.

In some embodiments, the temperature of the heat activated carbon during contacting is from about 50° C. to about 250° C. In some embodiments, the temperature of the heat activated carbon during contacting is from about 75° C. to about 200° C. In some embodiments, the temperature of the heat activated carbon during contacting is about 200° C.

The heat activated carbon can be at a temperature of, for example, about: 25° C. to 250° C., 25° C. to 225° C., 25° C. to 200° C., 25° C. to 175° C., 25° C. to 150° C., 25° C. to 100° C., 25° C. to 50° C., 50° C. to 225° C., 50° C. to 200° C., 50° C. to 175° C., 50° C. to 150° C., 50° C. to 100° C., 100° C. to 225° C., 100° C. to 200° C., 100° C. to 175° C., 100° C. to 150° C., 150° C. to 225° C., 150° C. to 200° C., 150° C. to 175° C., 175° C. to 225° C., or 175° C. to 200° C. when contacted with the sugar stream. In some embodiments, the activated carbon is at a temperature of from about 150° C. to about 250° C. during contacting. In some embodiments, the activated carbon is at a temperature of from about 175° C. to about 225° C. during contacting. In some embodiments, the activated carbon is at a temperature of about 200° C. during contacting.

In some embodiments, heating the activated carbon is performed in an oven. In some embodiments, heating the activated carbon is performed in an autoclave. In some embodiments, heating the activated carbon is performed in a vacuum.

In some embodiments, the heat activated carbon is used within, for example, about: 24 hours, 12 hours, 4 hours, 2 hours, 1 hour, 45 minutes, 30 minutes, 15 minutes, 10 minutes, 5 minutes, or 1 minute of heating. In some embodiments, contacting is performed within about 4 hours of heating. In some embodiments, contacting is performed within about 1 hour of heating. In some embodiments, contacting is performed within about 45 minutes of heating. In some embodiments, contacting is performed within about 30 minutes of heating.

In some embodiments, the heat activated carbon is stored in a non-oxidizing environment before contacting.

In some embodiments, the heat activated carbon is stored in an inert gas before contacting. In some embodiments, the inert gas is nitrogen, argon, helium, neon, krypton, xenon, radon, carbon dioxide, or a combination thereof.

In some embodiments, the heat activated carbon is in an oxygen-free environment before contacting.

In some embodiments, the heat activated carbon is stored is a water-free environment before contacting.

The sugar stream can be acidified before contacting the sugar stream with activated carbon. Acidifying the sugar stream can lower the pH of the sugar stream to, for example, from about 1 to about 4, from about 1 to about 3, from about 1.5 to about 3, from about 1 to about 2, about 1, about 2, about 3, about 4 or less, about 3 or less, about 2 or less, or about 1 or less. In some embodiments, acidifying the sugar stream is to the pH of from about 1.5 to about 3.

The sugar stream can have been produced by pretreating and/or hydrolyzing biomass according to any of the methods disclosed herein. In some embodiments, the sugar stream was produced by pretreating or hydrolyzing a biomass comprising cellulosic, hemicellulosic, or lignocellulosic material. In some embodiments, pretreating or hydrolyzing the biomass comprises mechanical size reduction, hot water treatment, acid treatment, base treatment, steam explosion, acid-catalyzed steam explosion, ammonia fiber/freeze explosion, enzymatic hydrolysis, or a combination thereof. In some embodiments, pretreating or hydrolyzing the biomass comprises mechanical size reduction, hot water treatment, acid treatment, base treatment, steam explosion, acid-catalyzed steam explosion, ammonia fiber/freeze explosion, enzymatic hydrolysis, or a combination thereof. In some embodiments, pretreating or hydrolyzing the biomass comprises mechanical size reduction, acid treatment and enzymatic hydrolysis.

In some embodiments, the sugar stream was produced by (1) pretreating a biomass comprising lignocellulosic material with hot water or an acid to solubilize hemicellulose in the biomass, (2) substantially separating solubilized hemicellulose from remaining lignocellulosic solids, and (3) enzymatically hydrolyzing cellulose in the remaining lignocellulosic solids.

In some embodiments, the sugar stream was produced by: (a) pretreating a biomass comprising cellulosic, hemicellulosic, or lignocellulosic material to produce a pretreated biomass comprising solid particles and optionally a yield of C5 monomers and/or dimers that is at least 50% of a theoretical maximum, wherein pretreating comprises: (i) hydration of the biomass in an aqueous medium to produce a hydrated biomass, (ii) mechanical size reduction of the hydrated biomass to produce the solid particles, and (iii) heating the hydrated biomass for a time sufficient to produce the pretreated biomass comprising the optional yield of C5 monosaccharides and/or disaccharides; and (b) hydrolyzing the pretreated biomass composition with one or more enzymes for a time sufficient to produce the sugar stream. In some embodiments, the aqueous medium comprises and acid. In some embodiments, the acid is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

In some embodiments, the sugar stream is a crude sugar stream.

In some embodiments, the sugar stream is a hydrolysate from the pretreatment and hydrolysis of a biomass comprising cellulose, hemicellulose, or lignocellulose.

In some embodiments, the sugar stream has a total sugar concentration of, for example, about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 15% w/v to about 60% w/v, about 15% w/v to about 50% w/v, about 15% w/v to about 40% w/v, about 15% w/v to about 30% w/v, about 15% w/v to about 20% w/v, about 5% w/v, about 15% w/v, about 25% w/v, about 35% w/v, about 45% w/v, or about 55% w/v. In some embodiments, the sugar stream has a total sugar concentration of at least about 15%, 20%, 25%, 30%, 35%, 40%, 45%, 50%, 55%, 60%, or more w/v. In some embodiments, the sugar stream has a total sugar concentration of from about 5% to about 60%. In some embodiments, the sugar stream has a total sugar concentration of from about 15% to about 40%.

In some embodiments, the sugar stream comprises C5 sugars, C6 sugars, or a combination thereof. In some embodiments, sugars in the sugar stream are monomers, dimers, or a combination thereof.

The sugar stream can be a C5-enriched sugar stream. For example, at least about: 50%, 60%, 70%, 75%, 80%, 85%, 90%, 95%, 96%, 97%, 98%, 99% of the sugars in the sugar stream can be C5 sugars. In some embodiments, at least about 70% of sugars in the sugar stream are C5 sugars. In some embodiments, at least about 80% of sugars in the sugar stream are C5 sugars. In some embodiments, at least about 90% of sugars in the sugar stream are C5 sugars.

The sugar stream can be a C6-enriched sugar stream. For example, at least about: 50%, 60%, 70%, 75%, 80%, 85%, 90%, 95%, 96%, 97%, 98%, 99% of the sugars in the sugar stream can be C6 sugars. In some embodiments, at least about 80% of sugars in the sugar stream are C6 sugars. In some embodiments, at least about 90% of sugars in the sugar stream are C6 sugars. In some embodiments, at least about 95% of sugars in the sugar stream are C6 sugars.

Some embodiments further comprise heating the sugar stream prior to contacting with the activated carbon. The sugar stream can be heated to, for example, about 40° C. to about 100° C., about 40° C. to about 80° C., about 50° C. to about 80° C., about 60° C. to about 80° C., about 70° C. to about 80° C., about 45° C., about 55° C., about 65° C., or about 70° C. In some embodiments, the sugar stream is at a temperature of from about 45° C. to about 100° C. In some embodiments, the sugar stream is at a temperature of from about 55° C. to about 75° C.

The time sufficient for producing a refined sugar stream can be, for example, about 1 hour to about 48 hours, about 1 hour to about 36 hours, about 1 hour to about 24 hours, about 1 hour to about 18 hours, about 1 hour to about 12 hours, about 1 hour to about 6 hours, about 2 hours, about 3 hours, about 4 hours, about 6 hours, about 7 hours, about 8 hours, about 9 hours, about 10 hours, about 11 hours, about 13 hours, about 14 hours, about 15 hours, about 17 hours, about 19 hours, about 20 hours, about 21 hours, about 22 hours, or about 23 hours. In some embodiments, the sufficient time is from about 30 minutes to about 5 hours. In some embodiments, the sufficient time is from about 1 hour to about 2 hours.

In some embodiments, the activated carbon is granular activated carbon, powdered activated carbon, graphene or a combination thereof. In some embodiments, the activated carbon is powdered activated carbon.

In some embodiments, the activated carbon is contained in the sugar stream in an amount of about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 2% w/v, about 3% w/v, about 4% w/v, about 5% w/v, about 6% w/v, about 7% w/v, about 8% w/v, about 9% w/v, about 15% w/v, about 25% w/v, about 35% w/v, or about 40% w/v during contacting. In some embodiments, the activated carbon is contained within the sugar stream at a concentration of from about 1% to about 20% during contacting. In some embodiments, the activated carbon is contained within the sugar stream at a concentration of from about 5% to about 15% during contacting. In some embodiments, the activated carbon is contained within the sugar stream at a concentration of about 10% during contacting.

In some embodiments, the activated carbon has a particle size of from about 5 microns to about 40 microns, about 5 microns to about 30 microns, about 5 microns to about 20 microns, less than about 40 microns, less than about 30 microns, less than about 20 microns, less than about 10 microns, or less than about 5 microns. In some embodiments, the activated carbon has a particle size of from about 5 microns to about 40 microns. In some embodiments, the activated carbon has a particle size averaging from about 5 microns to about 10 microns.

In some embodiments, the sugar stream is agitated, mixed, stirred, blended, shaken, sonicated, subjected to bubbling with a gas, subjected to bubbling with an inert gas, or any combination thereof during some or all of the contacting.

Some embodiments further comprise contacting the sugar stream with diatomaceous earth. In some embodiments, the diatomaceous earth is contained in the sugar stream during contacting in an amount of about 0.1% w/v to about 10% w/v, about 0.1% w/v to about 8% w/v, about 0.1% w/v to about 6% w/v, about 0.1% w/v to about 4% w/v, about 0.1% w/v to about 2% w/v, about 0.5% w/v, about 1% w/v, about 1.5% w/v, about 2.5% w/v, about 3.5% w/v, about 4.5% w/v, about 5.5% w/v, about 6.5% w/v, about 7.5% w/v, about 8.5% w/v, or about 9.5% w/v. In some embodiments, the diatomaceous earth is contained in the sugar stream during contacting in an amount of from about 0.1% w/v to about 2% w/v.

Some embodiments further comprise removing the activated carbon from the sugar stream after the sufficient time. Activated carbon can be removed, for example, by centrifugation, gravity settling, filtration, or a combination thereof.

In some embodiments, the sugar stream is contacted with the activated carbon in a column filtration system. The column filtration system can have diatomaceous earth in addition to the activated carbon. The column filtration system can be a counter current column filtration system. For example, the sugar stream can enter the bottom of the column and flow up through the activated carbon bed. A portion of the charcoal can be removed from the bottom of the column, for example and be replaced by fresh activated carbon added to the top of the column.

Also provided herein are the refined sugar streams produced by any of the methods disclosed herein.

Also disclosed are refined sugar stream comprising one or more of the following: (a) a concentration of total sugars that is at least about 15% w/v; (b) a concentration of one or more inhibitors that is at least about 70% less than an originator sugar stream; (c) a concentration of one or more aromatic or phenolic compounds that is at least about 30% less than the originator sugar stream; or (d) a transparency that is at least 50% higher than the originator sugar stream, wherein the refined sugar stream was contacted with activated carbon. The refined sugar stream can have been produced using any of the methods disclosed herein.

The sugar stream is a liquid. The activated carbon is a solid.

In some embodiments, the refined sugar stream has the concentration of total sugars of, for example, about 15% w/v to about 60% w/v, about 15% w/v to about 50% w/v, about 15% w/v to about 40% w/v, about 15% w/v to about 30% w/v, about 15% w/v to about 20% w/v, about 15% w/v, about 25% w/v, about 35% w/v, about 45% w/v, or about 55% w/v. In some embodiments, the refined sugar stream has the concentration of total sugars of at least about: 15%, 20%, 25%, 30%, 35%, 40%, 45%, 50%, 55%, 60%, or more w/v. In some embodiments, the concentration of total sugars is from about 15% to about 60% w/v.

In some embodiments, the refined sugar stream has a concentration of total sugars of from about 5% to about 60%. In some embodiments, the refined sugar stream has a concentration of total sugars of from about 15% to about 40%.

In some embodiments, the refined sugar stream comprises the concentration of one or more inhibitors that is at least about 70% less than an originator sugar stream. In some embodiments, the one or more inhibitors comprise furfural, hydroxymethylfurfural, or a combination thereof. In some embodiments, the concentration of one or more inhibitors is at least about 80% less than in the sugar stream that was not refined with activated carbon. In some embodiments, the concentration of one or more inhibitors is at least about 90% less than in the sugar stream that was not refined with activated carbon.

In some embodiments, the refined sugar stream comprises the concentration of one or more aromatic or phenolic compounds that is at least about 30% less than the originator sugar stream. The concentration of one or more aromatic or phenolic compounds can be least about: 40%, 50%, 60%, 70%, 75%, 80%, 85%, 90%, 95%, 96%, 97%, 98%, or 99% less than the originator sugar stream. In some embodiments, at least one of the aromatic or phenolic compounds is a lignin hydrolysis product. In some embodiments, the concentration of one or more aromatic or phenolic compounds is at least about 50% less than in the originator sugar stream.

In some embodiments, the concentration of one or more aromatic or phenolic compounds is at least about 70% less than in the originator sugar stream.

In some embodiments, the refined sugar stream comprises the transparency that is at least 50% higher than the originator sugar stream. The transparency of the refined sugar stream can be: 55%, 60%, 65%, 70%, 75%, 80%, 85%, 90%, 95%, 96%, 97%, 98%, or 99% greater than the originator sugar stream. In some embodiments, the transparency is measured at 600 nm. In some embodiments, the transparency is at least 75% higher than in the originator sugar stream.

The originator sugar stream can have been produced by pretreating and/or hydrolyzing biomass according to any of the methods disclosed herein. In some embodiments, the originator sugar stream was produced by pretreating or hydrolyzing a biomass comprising cellulosic, hemicellulosic, or lignocellulosic material.

In some embodiments, pretreating or hydrolyzing the biomass comprises mechanical size reduction, hot water treatment, acid treatment, base treatment, steam explosion, acid-catalyzed steam explosion, ammonia fiber/freeze explosion, enzymatic hydrolysis, or a combination thereof. In some embodiments, pretreating or hydrolyzing the biomass comprises mechanical size reduction, acid treatment and enzymatic hydrolysis.

In some embodiments, the originator sugar stream was produced by (1) pretreating a biomass comprising lignocellulosic material with hot water or an acid to solubilize hemicellulose in the biomass, (2) substantially separating solubilized hemicellulose from remaining lignocellulosic solids, and (3) enzymatically hydrolyzing cellulose in the remaining lignocellulosic solids.

In some embodiments, the originator sugar stream was produced by: (a) pretreating a biomass comprising cellulosic, hemicellulosic, or lignocellulosic material to produce a pretreated biomass comprising solid particles and optionally a yield of C5 monomers and/or dimers that is at least 50% of a theoretical maximum, wherein pretreating comprises: (i) hydration of the biomass in an aqueous medium to produce a hydrated biomass, (ii) mechanical size reduction of the hydrated biomass to produce the solid particles, and (iii) heating the hydrated biomass for a time sufficient to produce the pretreated biomass comprising the optional yield of C5 monosaccharides and/or disaccharides; and (b) hydrolyzing the pretreated biomass composition with one or more enzymes for a time sufficient to produce the sugar stream. In some embodiments, the aqueous medium comprises and acid. In some embodiments, the acid is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

In some embodiments, the originator sugar stream is a crude originator sugar stream.

In some embodiments, the originator sugar stream is a hydrolysate from the pretreatment and hydrolysis of a biomass comprising cellulose, hemicellulose, or lignocellulose.

In some embodiments, the sugar stream comprises C5 sugars, C6 sugars, or a combination thereof.

The refined sugar stream can be a C5-enriched sugar stream. For example, at least about: 50%, 60%, 70%, 75%, 80%, 85%, 90%, 95%, 96%, 97%, 98%, 99% of the sugars in the refined sugar stream can be C5 sugars. In some embodiments, at least about 70% of sugars in the refined sugar stream are C5 sugars. In some embodiments, at least about 80% of sugars in the refined sugar stream are C5 sugars. In some embodiments, at least about 90% of sugars in the refined sugar stream are C5 sugars.

The refined sugar stream can be a C6-enriched sugar stream. For example, at least about: 50%, 60%, 70%, 75%, 80%, 85%, 90%, 95%, 96%, 97%, 98%, 99% of the sugars in the refined sugar stream can be C6 sugars. In some embodiments, at least about 80% of sugars in the refined sugar stream are C6 sugars. In some embodiments, at least about 90% of sugars in the refined sugar stream are C6 sugars. In some embodiments, at least about 95% of sugars in the refined sugar stream are C6 sugars.

In some embodiments, sugars in the refined sugar stream are monomers, dimers, or a combination thereof.

The following embodiments are also provided:

Embodiment Numbers

1. A method of refining a sugar stream, comprising contacting the sugar stream with activated carbon.
2. The method of embodiment 1, wherein the activated carbon is powdered activated carbon (PAC), granular activated carbon (GAC), graphene, or a combination thereof.
3. The method of embodiment 1 or embodiment 2, wherein the activated carbon has a particle size of from about 5 microns to about 40 microns, about 5 microns to about 30 microns, about 5 microns to about 20 microns, less than about 40 microns, less than about 30 microns, less than about 20 microns, less than about 10 microns, or less than about 5 microns.
4. The method of any one of embodiments 1-3, wherein the activated carbon has a particle size ranging from about 5 microns to about 10 microns.

In one aspect, provided herein is a method of refining a sugar stream, comprising contacting the sugar stream with activated carbon.

In some embodiments, the activated carbon is powdered activated carbon (PAC), granular activated carbon (GAC), graphene, or a combination thereof.

In some embodiments, the activated carbon has a particle size of from about 5 microns to about 40 microns, about 5 microns to about 30 microns, about 5 microns to about 20 microns, less than about 40 microns, less than about 30 microns, less than about 20 microns, less than about 10 microns, or less than about 5 microns.

In some embodiments, the activated carbon has a particle size ranging from about 5 microns to about 10 microns.

In some embodiments, the contacting is conducted at a temperature of about 40° C. to about 80° C., about 50° C. to about 80° C., about 60° C. to about 80° C., about 70° C. to about 80° C., about 45° C., about 55° C., about 65° C., or about 70° C.

In some embodiments, the contacting is conducted for a time period of about 1 hour to about 48 hours, about 1 hour to about 36 hours, about 1 hour to about 24 hours, about 1 hour to about 18 hours, about 1 hour to about 12 hours, about 1 hour to about 6 hours, about 2 hours, about 3 hours, about 4 hours, about 6 hours, about 7 hours, about 8 hours, about 9 hours, about 10 hours, about 11 hours, about 13 hours, about 14 hours, about 15 hours, about 17 hours, about 19 hours, about 20 hours, about 21 hours, about 22 hours, or about 23 hours.

In some embodiments, the activated carbon is contained in the sugar stream in an amount of about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 2% w/v, about 3% w/v, about 4% w/v, about 5% w/v, about 6% w/v, about 7% w/v, about 8% w/v, about 9% w/v, about 15% w/v, about 25% w/v, about 35% w/v, or about 40% w/v.

In some embodiments, wherein the pH of the sugar stream is: from about 1 to about 3, from about 1 to about 2, about 1, about 2, about 3, about 3 or less, about 2 or less, or about 1 or less.

In some embodiments, the method further comprises contacting the sugar stream with diatomaceous earth.

In some embodiments, the diatomaceous earth is contained in the sugar stream in an amount of: about 0.1% w/v to about 10% w/v, about 0.1% w/v to about 8% w/v, about 0.1% w/v to about 6% w/v, about 0.1% w/v to about 4% w/v, about 0.1% w/v to about 2% w/v, about 0.5% w/v, about 1% w/v, about 1.5% w/v, about 2.5% w/v, about 3.5% w/v, about 4.5% w/v, about 5.5% w/v, about 6.5% w/v, about 7.5% w/v, about 8.5% w/v, or about 9.5% w/v.

In some embodiments, the sugar stream is agitated, mixed, stirred, blended, shaken, sonicated, subjected to bubbling with a gas, subjected to bubbling with an inert gas, or any combination thereof during some or all of the contacting.

In some embodiments, the sugar stream comprises C5 sugars, C6 sugars, or a combination thereof.

In some embodiments, the amount of sugars in the sugar stream is: about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 5% w/v, about 15% w/v, about 25% w/v, about 35% w/v, about 45% w/v, or about 55% w/v.

In some embodiments, the method further comprises, after the contacting, conducting a purification.

In some embodiments, the purification is a flocculation, a filtration, a centrifugation, or any combination thereof.

In some embodiments, the activated carbon, before the contacting, is activated by heating.

In some embodiments, the heating is conducted for a time period of about 1 hour to about 48 hours, about 1 hour to about 36 hours, about 1 hour to about 24 hours, about 1 hour to about 18 hours, about 1 hour to about 12 hours, about 1 hour to about 6 hours, about 2 hours, about 3 hours, about 4 hours, about 6 hours, about 7 hours, about 8 hours, about 9 hours, about 10 hours, about 11 hours, about 13 hours, about 14 hours, about 15 hours, about 17 hours, about 19 hours, about 20 hours, about 21 hours, about 22 hours, or about 23 hours.

In some embodiments, the heating is conducted at a temperature of: about 150° C. to about 300° C., about 150° C. to about 250° C., about 150° C. to about 200° C., about 160° C., about 170° C., about 180° C., about 190° C., about 210° C., about 220° C., about 230° C., about 240° C., about 260° C., about 270° C., about 280° C., or about 290° C.

In some embodiments, the heating is conducted under vacuum.

In some embodiments, the method further comprises, after the contacting, or after the conducting a purification, or after the contacting and the conducting a purification, concentrating the sugar stream.

In some embodiments, the sugar stream comprises water, an alcohol, an acid, or a combination thereof.

In some embodiments, the sugar stream, prior to the contacting, is subjected to an enzymatic hydrolysis.

In some embodiments, wherein the sugar stream, prior to the contacting, is subjected to a pretreatment.

In some embodiments, the sugar stream is derived from a biomass.

In some embodiments, is provided an isolated, refined sugar stream produced by the method of any one of the above embodiments.

In some embodiments, the isolated, refined sugar stream is substantially colorless or colorless.

In some embodiments is provided an isolated sugar stream comprising activated carbon and optionally at least one of diatomaceous earth, an acid, an alcohol, or any combination thereof.

In some embodiments, in the isolated sugar stream the activated carbon is powdered activated carbon (PAC), granular activated carbon (GAC), graphene, or a combination thereof.

In some embodiments, the activated carbon has a particle size of from about 5 microns to about 40 microns, about 5 microns to about 30 microns, about 5 microns to about 20 microns, less than about 40 microns, less than about 30 microns, less than about 20 microns, less than about 10 microns, or less than about 5 microns.

In some embodiments, the isolated sugar stream has a pH of from about 1 to about 3, from about 1 to about 2, about 1, about 2, about 3, about 3 or less, about 2 or less, or about 1 or less.

In some embodiments, the activated carbon is contained in the sugar stream in an amount of about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 2% w/v, about 3% w/v, about 4% w/v, about 5% w/v, about 6% w/v, about 7% w/v, about 8% w/v, about 9% w/v, about 15% w/v, about 25% w/v, about 35% w/v, or about 40% w/v.

In some embodiments, the isolated sugar stream comprises C5 sugars, C6 sugars, or a combination thereof.

In some embodiments, the amount of sugar in the sugar stream is: about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 5% w/v, about 15% w/v, about 25% w/v, about 35% w/v, about 45% w/v, or about 55% w/v.

In some embodiments is provided a method of producing a sugar stream comprising C5 and C6 sugars from a biomass composition comprising cellulose, hemicellulose, and/or lignocellulose, the method comprising:

(a) pretreating the biomass composition comprising cellulose, hemicellulose, and/or lignocellulose to produce a pretreated biomass composition comprising solid particles and optionally a yield of C5 monomers and/or dimers that is at least 50% of a theoretical maximum, wherein pretreating comprises:

(i) hydration of the biomass composition in a non-neutral pH aqueous medium to produce a hydrated biomass composition, (ii) mechanical size reduction of the hydrated biomass composition to produce the solid particles, and (iii) heating the hydrated biomass composition for a time sufficient to produce the pretreated biomass composition comprising the optional yield of C5 monomers and/or dimers that is at least 50% of the theoretical maximum;

(b) hydrolyzing the pretreated biomass composition with one or more enzymes for a time sufficient to produce the composition comprising C6 and C5 sugars;

(c) washing the composition to recover a sugar stream substantially enriched for C6 and/or C5 sugars; and (d) contacting the sugar stream with activated carbon to produce a clarified sugar stream.

In some embodiments, at least 50% of the solid particles in the pretreated biomass composition are from about 0.1 mm to about 1 mm in size.

In some embodiments, all of the solid particles in the pretreated biomass are less than 7.5 mm in size.

In some embodiments, all of the solid particles in the pretreated biomass are less than 1 mm in size.

In some embodiments, the C5 monomers and/or dimers in the pretreated biomass composition are monomers.

In some embodiments, the yield of C5 monomers and/or dimers is at least 80% of the theoretical maximum.

In some embodiments, the pretreated biomass composition further comprises a yield of glucose that is less than about 20% of the theoretical maximum.

In some embodiments, the hydrated biomass composition comprises from about 1% to about 20% solids by dry biomass weight.

In some embodiments, the non-neutral pH aqueous medium is at from about 30° C. to about 70° C.

In some embodiments, hydration of the biomass composition is for about 1 minute to about 60 minutes.

In some embodiments, the non-neutral aqueous medium comprises an acid or a base at from about 0.1% to about 5% v/w by dry biomass weight.

In some embodiments, the non-neutral pH aqueous medium comprises the acid that is sulfuric acid, peroxyacetic acid, lactic acid, formic acid, acetic acid, citric acid, phosphoric acid, hydrochloric acid, sulfurous acid, chloro acetic acid, dichloroacetic acid, trichloroacetic acid, trifluoroacetic acid, oxalic acid, benzoic acid, or a combination thereof.

In some embodiments, mechanical size reduction comprises cutting, steam injection, steam explosion, acid-catalyzed steam explosion, ammonia fiber/freeze explosion (AFEX) or a combination thereof.

In some embodiments, heating of the hydrated biomass composition is at a temperature of from about 100° C. to about 250° C.

In some embodiments, heating of the hydrated biomass composition is performed at a pressure of from about 100 PSIG to about 150 PSIG.

In some embodiments, the time sufficient to produce the yield of C5 monomers and/or dimers is from about 1 minute to about 30 minutes.

In some embodiments, pretreating the biomass composition further comprises dewatering the hydrated biomass composition to from about 10% to about 40% solids by dry biomass weight.

In some embodiments, heating comprises steam explosion, acid-catalyzed steam explosion, ammonia fiber/freeze explosion (AFEX), or a combination thereof.

In some embodiments, the pretreating is performed in a continuous mode of operation.

In some embodiments, the pretreating is performed in a total time of from about 15 minutes to about 45 minutes.

In some embodiments, the one or more enzymes comprise one or more hemicellulases and/or one or more cellulases.

In some embodiments, the one or more enzymes are at a total level from about 1% to about 20% w/w by dry biomass weight.

In some embodiments, the method further comprises adjusting the water content of the pretreated biomass composition to from about 5% to about 30% solids by dry biomass weight prior to hydrolyzing.

In some embodiments, the composition comprising C6 and C5 sugars comprises glucose, xylose, mannose, galactose, rhamnose, arabinose, or a combination thereof.

In some embodiments, the composition comprising C6 and C5 sugars is an aqueous composition.

In some embodiments, the composition comprising C6 and C5 sugars comprises glucose in a yield that is greater than 55% of a theoretical maximum at 21 hours of hydrolysis.

In some embodiments, the biomass composition comprises alfalfa, algae, bagasse, bamboo, corn stover, corn cobs, corn kernels, corn mash, corn steep liquor, corn steep solids, distiller's grains, distiller's dried solubles, distiller's dried grains, condensed distiller's solubles, distiller's wet grains, distiller's dried grains with solubles, *eucalyptus*, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheat bran, willows, wood, plant cells, plant tissue cultures, tissue cultures, or a combination thereof.

In some embodiments, mechanical size reduction does not comprise milling.

In some embodiments, the activated carbon is powdered activated carbon (PAC), granular activated carbon (GAC), graphene, or a combination thereof.

In some embodiments, the activated carbon has a particle size of from about 5 microns to about 40 microns, about 5 microns to about 30 microns, about 5 microns to about 20 microns, less than about 40 microns, less than about 30 microns, less than about 20 microns, less than about 10 microns, or less than about 5 microns.

In some embodiments, the activated carbon has a particle size ranging from about 5 microns to about 10 microns.

In some embodiments, the contacting is conducted at a temperature of: about 40° C. to about 80° C., about 50° C. to about 80° C., about 60° C. to about 80° C., about 70° C. to about 80° C., about 45° C., about 55° C., about 65° C., or about 70° C.

In some embodiments, the contacting is conducted for a time period of: about 1 hour to about 48 hours, about 1 hour to about 36 hours, about 1 hour to about 24 hours, about 1 hour to about 18 hours, about 1 hour to about 12 hours, about 1 hour to about 6 hours, about 2 hours, about 3 hours, about 4 hours, about 6 hours, about 7 hours, about 8 hours, about 9 hours, about 10 hours, about 11 hours, about 13 hours, about 14 hours, about 15 hours, about 17 hours, about 19 hours, about 20 hours, about 21 hours, about 22 hours, or about 23 hours.

In some embodiments, the activated carbon is contained in the sugar stream in an amount of: about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 2% w/v, about 3% w/v, about 4% w/v, about 5% w/v, about 6% w/v, about 7% w/v, about 8% w/v, about 9% w/v, about 15% w/v, about 25% w/v, about 35% w/v, or about 40% w/v.

In some embodiments, the pH of the sugar stream is: from about 1 to about 3, from about 1 to about 2, about 1, about 2, about 3, about 3 or less, about 2 or less, or about 1 or less.

In some embodiments, the method further comprises contacting the sugar stream with diatomaceous earth.

In some embodiments, the diatomaceous earth is contained in the sugar stream in an amount of: about 0.1% w/v to about 10% w/v, about 0.1% w/v to about 8% w/v, about 0.1% w/v to about 6% w/v, about 0.1% w/v to about 4% w/v, about 0.1% w/v to about 2% w/v, about 0.5% w/v, about 1% w/v, about 1.5% w/v, about 2.5% w/v, about 3.5% w/v, about 4.5% w/v, about 5.5% w/v, about 6.5% w/v, about 7.5% w/v, about 8.5% w/v, or about 9.5% w/v.

In some embodiments, the sugar stream is agitated, mixed, stirred, blended, shaken, sonicated, subjected to bubbling with a gas, subjected to bubbling with an inert gas, or any combination thereof during some or all of the contacting.

In some embodiments, the sugar stream comprises C5 sugars, C6 sugars, or a combination thereof.

In some embodiments, the amount of sugars in the sugar stream is: about 1% w/v to about 60% w/v, about 1% w/v to about 50% w/v, about 1% w/v to about 40% w/v, about 1% w/v to about 30% w/v, about 1% w/v to about 20% w/v, about 1% w/v to about 10% w/v, about 5% w/v, about 15% w/v, about 25% w/v, about 35% w/v, about 45% w/v, or about 55% w/v.

In some embodiments, the method further comprises, after the contacting, conducting a purification.

In some embodiments, the purification is a flocculation, a filtration, a centrifugation, or any combination thereof.

In some embodiments, the activated carbon, before the contacting, is activated by heating.

In some embodiments, the heating is conducted for a time period of about 1 hour to about 48 hours, about 1 hour to about 36 hours, about 1 hour to about 24 hours, about 1 hour to about 18 hours, about 1 hour to about 12 hours, about 1 hour to about 6 hours, about 2 hours, about 3 hours, about 4 hours, about 6 hours, about 7 hours, about 8 hours, about 9 hours, about 10 hours, about 11 hours, about 13 hours, about 14 hours, about 15 hours, about 17 hours, about 19 hours, about 20 hours, about 21 hours, about 22 hours, or about 23 hours.

In some embodiments, the heating is conducted at a temperature of about 150° C. to about 300° C., about 150° C. to about 250° C., about 150° C. to about 200° C., about 160° C., about 170° C., about 180° C., about 190° C., about 210° C., about 220° C., about 230° C., about 240° C., about 260° C., about 270° C., about 280° C., or about 290° C.

In some embodiments, the heating is conducted under vacuum.

In some embodiments, the method further comprises, after the contacting, or after the conducting a purification, or after the contacting and the conducting a purification, concentrating the sugar stream.

In some embodiments, the sugar stream comprises water, an alcohol, an acid, or a combination thereof.

In some embodiments, the sugar stream, prior to the contacting, is subjected to an enzymatic hydrolysis.

In some embodiments, the sugar stream, prior to the contacting, is subjected to a pretreatment.

In some embodiments, the sugar stream is derived from a biomass.

In some embodiments is provided an isolated, refined sugar stream produced by the method of any one of the above embodiments.

In some embodiments is provided a clarified sugar stream comprising C5 and/or C6 sugars produced by any of the above embodiments.

In some embodiments is provided a system for producing a refined sugar stream, comprising: a purification unit configured to refine the sugar stream by the method of any previous method embodiment.

In some embodiments, the system further comprises, upstream of the purification unit a concentrator configured to concentrate the sugar stream before it is fed to the purification unit.

In some embodiments, the system further comprises, upstream of the concentrator, a hydrolysis unit configured to perform a hydrolysis on a biomass to create a sugar stream.

In some embodiments, the system further comprises, upstream of the acid hydrolysis unit, a pretreatment unit, configured to pretreat a biomass by at least one of mechanical processing, heat, acid hydrolysis, or any combination thereof.

In some embodiments, the system further comprises, upstream of the pretreatment unit, a washing unit configured to wash a biomass before the biomass is fed to the pretreatment unit.

In some embodiments, the system further comprises, upstream of the hydrolysis unit and downstream of the pretreatment unit, a washing unit configured to wash pretreated biomass before the pretreated biomass is fed to the hydrolysis unit.

In another aspect, the products made by any of the processes described herein is provided.

EXAMPLES

The following examples serve to illustrate certain embodiments and aspects and are not to be construed as limiting the scope thereof.

Example 1

Activated carbon is a form of carbon that has been reduced in particle size and its surface is covered in low volume pores which increase the surface area for absorption. There are many types of activated carbon used in industry and these serve various purposes. To compare and contrast the differences in use of powdered activated carbon (PAC) and granular activated carbon (GAC), comparisons were made based on the level of inhibitors removed (acetic acid, HMF and Furfural), the level of color removed, and the level of various aromatics measured by the UV-spectrometer on the HPLC.

To activate the carbon, 500 grams of PAC (Sigma Aldrich c9157 activated carbon) was placed into a hot air oven and heated for 12 hours at 200° C. One 10 g sample of PAC was sequestered and placed into a 250 mL shake flask. 100 g of GAC (Fisher Scientific 05690-A) was placed into a hot air oven and heated for 12 hours at 200° C. One 10 g sample of GAC was sequestered and placed into a 250 mL shake flask. Both of these flasks were then replaced into the oven at 200° C. for 1 hour. The carbon samples were then removed to be tested with their respective sugar solutions.

A stock sugar stream from corn stover was prepared in a 90:10 ratio of C6 to C5 monomeric sugar hydrolysate with 40% total sugars (wt/v). The sugar solution was adjusted to pH 2.0 using concentrated sulfuric acid. Then 5 mL of acetic acid, 2.5 g of 5-Hydroxymethyl 2-furaldehyde (HMF) and 2.5 mL of Furfural were added to the stock sugar solution which was then heated to 65° C. for 1 hour with agitation. A 2 mL sample of the stock solution was analyzed using HPLC. Three 100 mL sugar stream samples were used to produce, respectively, a control, a "GAC" carbon treatment to which 10 g of GAC was added, and a "PAC" carbon treatment to which 10 g of PAC was added. All flasks were agitated at 65° C. for 2 hours.

Each of the three samples were analyzed with a spectrometer following treatment and filtration to remove any trace carbon. Measurements were recorded at 600 nm wavelength and water used as the baseline set to equal 100% light transmittance.

Samples were characterized via HPLC using a Shimadzu HLPC system. The detectors used were an RID-10A for characterizing sugars and organic acids along with HMF and Furfural. The SPD-20A UV detector was used to characterize aromatics and phenolics found within the sugar solutions eluted through a BIORAD Aminex HPX-87H Column (300×7.8 mm). Analysis was performed using a 0.01N $H_2SO_4$ mobile phase that was prepared using dd$H_2O$ and >95% pure $H_2SO_4$, and degassed for 10 minutes using a Helium purge. The mobile phase was maintained at a flow rate of 0.6 mL/min and in combination with a 64 injection volume, 65° C. oven temperature, and a backpressure of ~580 psi. Under these conditions, each sample was void of solids using a 0.2 micron filter and subjected to a 45 minute run time.

Table 1 shows the results of the color removal of the activated carbon streams from spectrometer readings.

TABLE 1

| Sample | % transmittance | % reduction in color |
| --- | --- | --- |
| Control | 62.0 | 0.0 |
| GAC | 70.4 | 22.1 |
| PAC | 99.9 | 99.7 |

Figure 2:
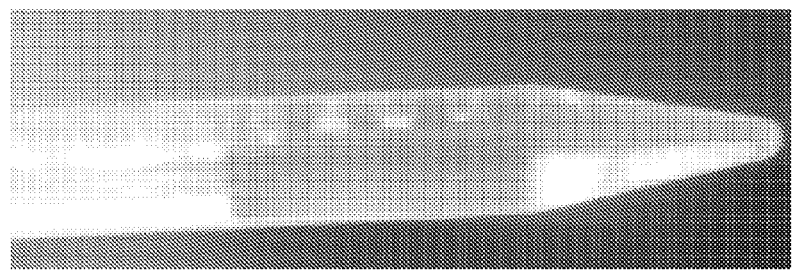
FIGS. 2A, 2B, and 2C depict the difference in treatment of a sugar stream without carbon (2A), with GAC (2B) and with PAC (2C).
Figure 2:
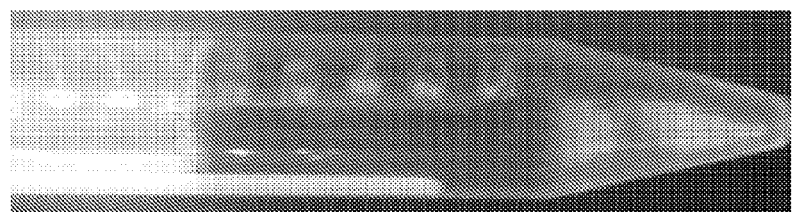
Figure 2:
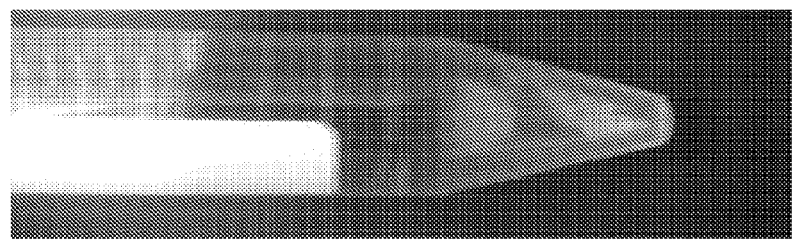

FIGS. 2A, 2B and 2C show the visible results following filtration of all three samples. There is no change is the control (FIG. 2A), considerable change with granular activated carbon treatment (FIG. 2B), and almost complete removal of color using powdered activated carbon (FIG. 2C).

Table 2 shows the reduction of the inhibitors acetic acid, HMF and Furfural with the use of GAC versus PAC.

TABLE 2

| Sample Name | Glucose (g/L) | Xylose (g/L) | Arabinose (g/L) | Acetic Acid (g/L) | HMF (g/L) | Furfural (g/L) |
| --- | --- | --- | --- | --- | --- | --- |
| Control | 383.31 | 35.52 | 0.29 | 12.96 | 5.09 | 5.00 |
| GAC | 366.43 | 32.82 | 0.30 | 11.71 | 0.29 | 0.21 |
| PAC | 382.58 | 35.10 | 0.31 | 11.67 | 0.61 | 0.48 |

Figure 3:
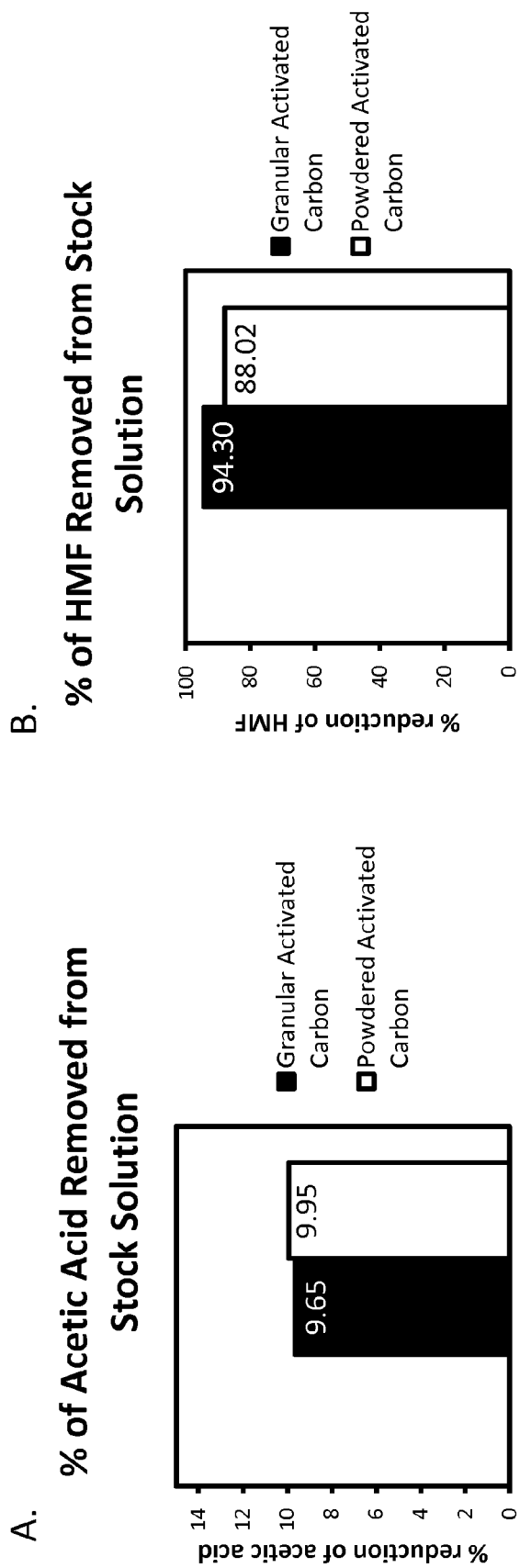
FIGS. 3A and 3B are graphs depicting the removal of acetic acid and HMF, respectively, from a sugar stream using GAC and PAC.
Figure 4:
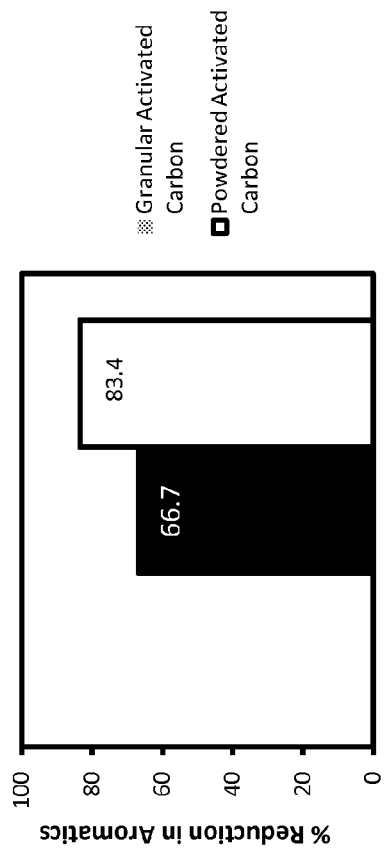
FIGS. 4A and 4B graphs depicting the removal of furfural and reduction of phenolics, respectively, from a sugar stream using GAC and PAC.
Figure 4:
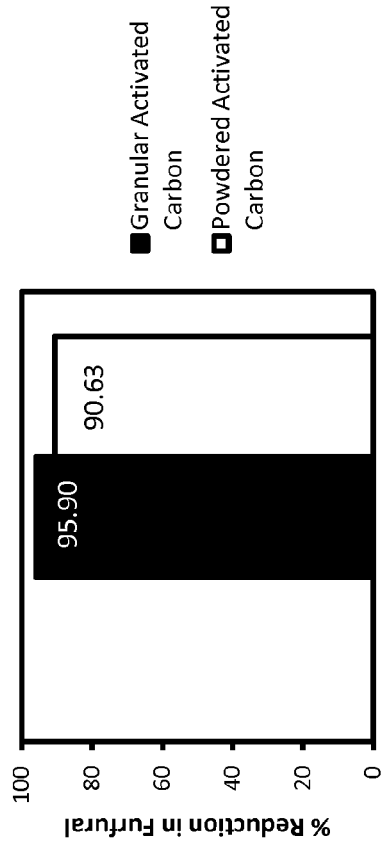

FIGS. 3A, 3B, 4A, and 4B show the graphical representation of the percentage of reduction for each of the three inhibitor levels. FIG. 3A indicates the percentage of acetic acid removed using GAC and PAC. FIG. 3B indicates the percentage of HMF removed from the corn stover stock solution using GAC and PAC. FIG. 4A indicates the percentage of furfural removed from the corn stover stock solution using GAC and PAC. FIG. 4B indicates the percentage reduction in the level of phenolics and aromatics.

Table 3 displays the level of phenolics and aromatics detected by the HPLC using a UV detector. The level of phenolics and aromatics are displayed by taking the entire peak area displayed from 0-45 minutes of the HPLC run at 205 nm.

TABLE 3

| Sample | Total Peak Area Detected | Percentage of Total Peak Area Reduction - based on control |
|---|---|---|
| Control | 158551825 mV | N/A |
| GAC | 52842525 mV | 66.7% |
| PAC | 26359915 mV | 83.4% |

Figure 5:
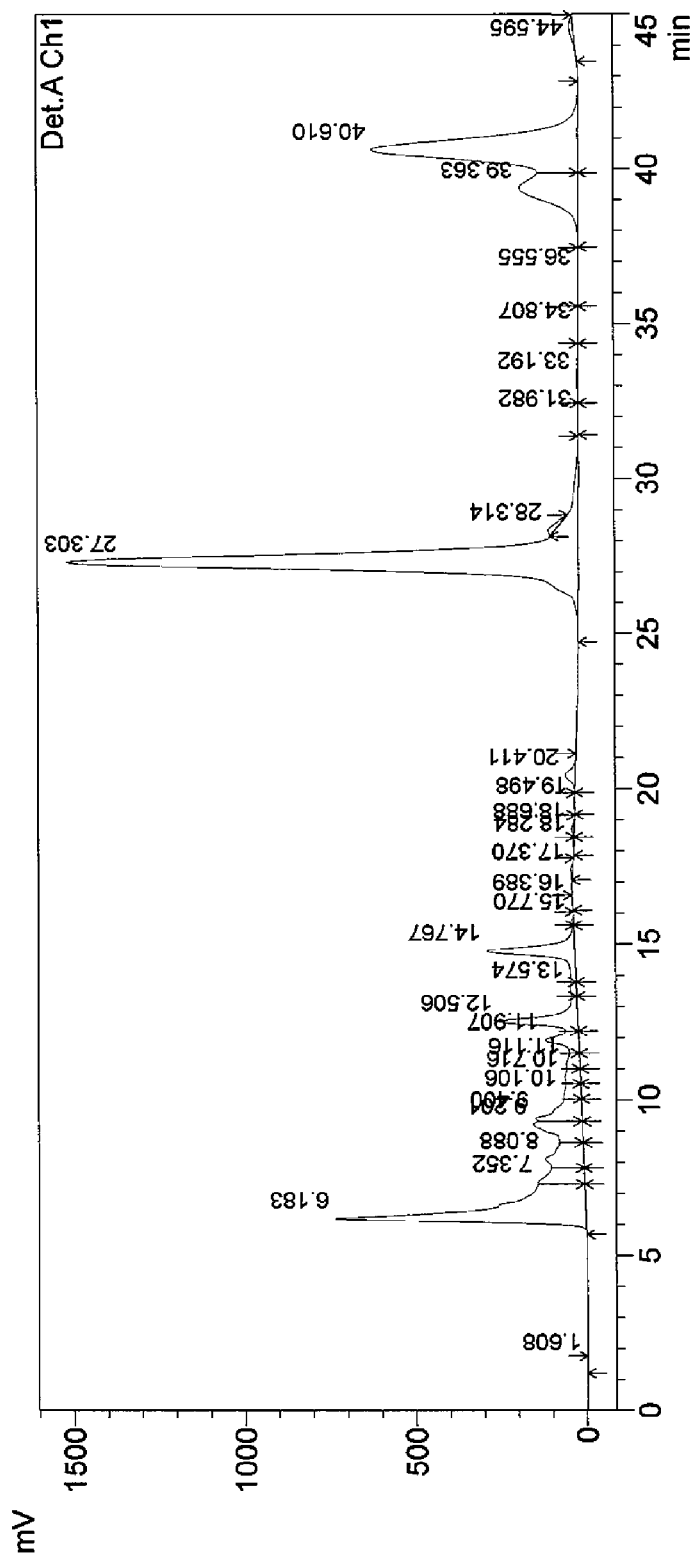
FIGS. 5A, 5B, and 5C show the UV-detector peaks of the control (5A), the GAC-treated (5B), and PAC-treated sugar hydrolysates (5C).
Figure 5:
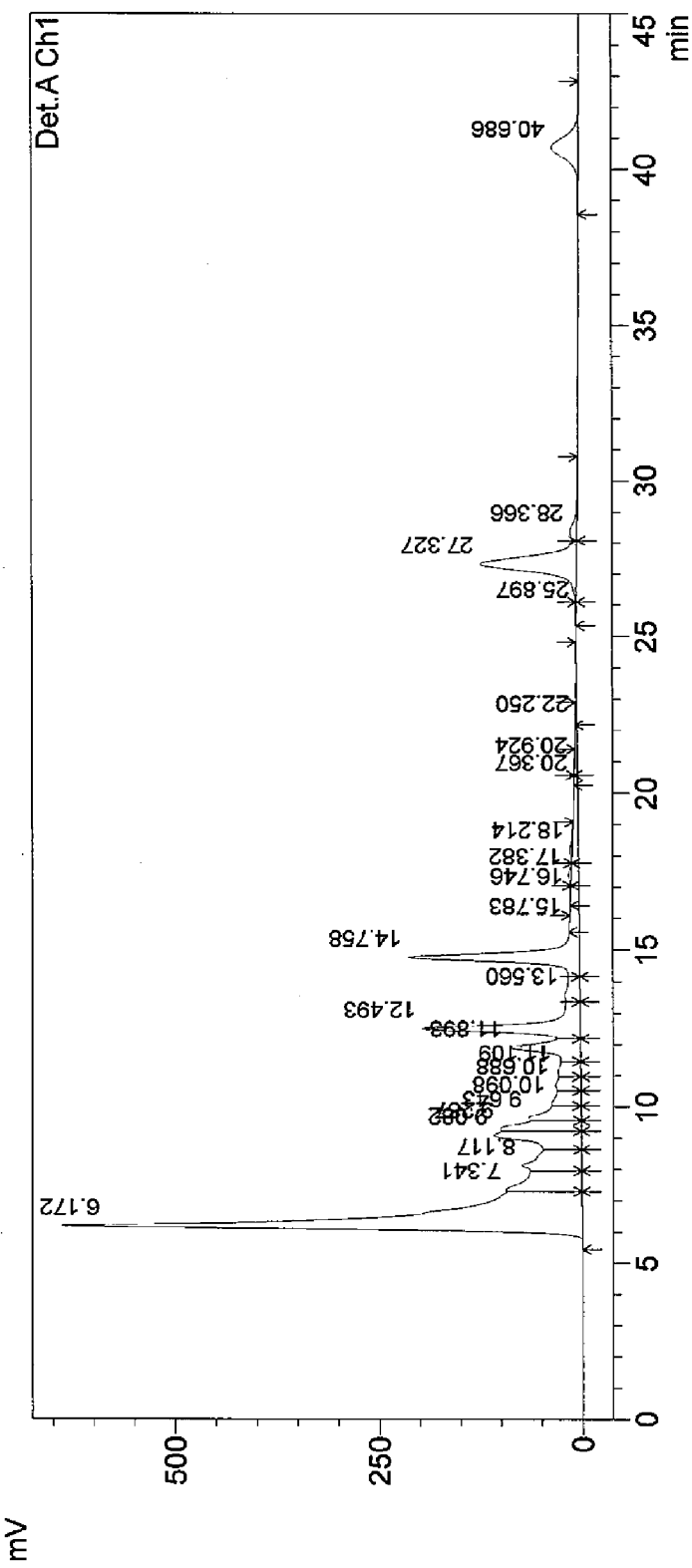
Figure 5:
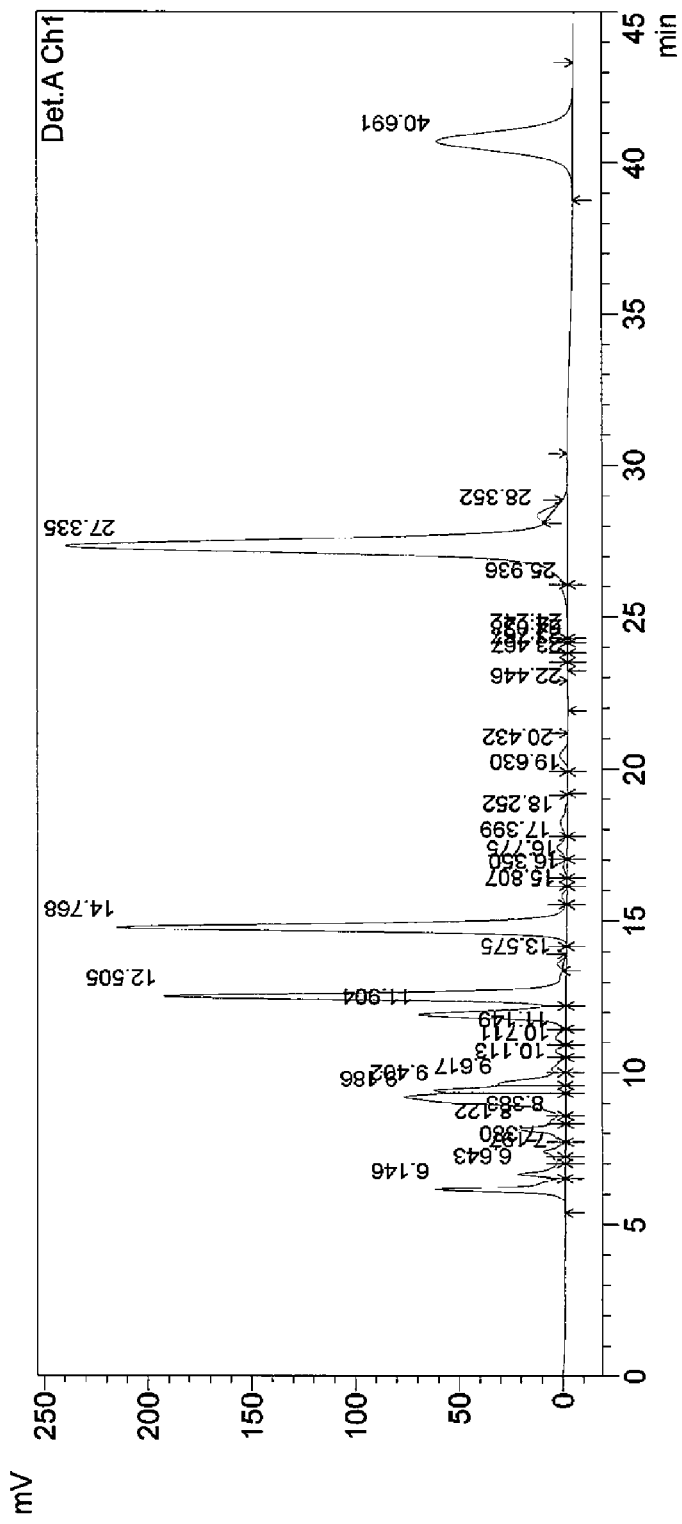

FIGS. 5A, 5B, and 5C show the UV-detector peaks of the control, the GAC-treated, and PAC-treated sugar hydrolysates, respectively.

There is a clear indication that both powdered activated carbon and granular activated carbon have the ability to sequester HMF and Furfural from monomeric sugar hydrolysates. GAC has a slightly greater edge in sequestering HMF and Furfural (~95% removal compared to ~90% removal for PAC). However, PAC has a better ability to sequester color, (99.7% compared to 22.1%) and aromatics (83.4% compared to 66.7%) from the broth than the GAC. The one factor that separates these two carbon types more than anything else is the ability to sequester color by the PAC.

Example 2

The activated carbon used was purchased or prepared in a powder form. The particle size was between 5 to 40 microns. Larger particle size, (75 microns or above) may remove impurities but not necessarily the color. The temperature of the carbon was raised to 200° C. prior to contact with the sugar syrup. This was typically done by the use of an oven for a period ranging from 4 hours to 24 hours but other means and times can be used.

The sugar syrup used for high concentration purification was 50% w/v at highest concentration, and was achieved through evaporation of the pretreatment liquor and maintenance at 50° C. or higher. The carbon is added to the solution while the solution and the carbon are still hot. Heated carbon can be more effective in color removal. The carbon was heated to 200° C. and the liquor typically kept at no less than 50° C. The pH of the sugar syrup can also be important. Dropping the pH of the sugar solution to about 2 before adding carbon can yield better clarification when the cellulosic stream is at a sugar concentration above 15% total sugars. Without heating the carbon, the sugar solution can retain full color if it is concentrated to 15% w/v or higher.

Clarification of a 50% sugar solution (hardwood derived sugars) was carried out as follows. The hardwood was pretreated using a Comet 10L reactor with 3% $SO_2$ (v/wt of dry solids) at 195° C. for 10 minutes. Following pretreatment, the hardwood was washed to remove C5 sugars. The hardwood was then enzymatically hydrolyzed and then concentrated to 50% total sugars using evaporation.

Following concentration, pH of the hardwood was adjusted to 2.0 using concentrated sulfuric acid. The hardwood was then heated at 50° C. and retained at that temperature for 1 hour. After heating the sugars, 10 g (20% wt/vol) of carbon, activated at 200° C. for 24 hours, was added to the sugars. Diatomaceous earth (0.6 g) was also added to the 50 mL sugar solution (1.25% wt/vol) to facilitate carbon removal during filtration. The solution was then maintained at 50° C. overnight. The solution was centrifuged and filtered using a 0.22 micron filter.

A sample of the 50% sugar solution was analyzed by HPLC before and after clarification to track the loss of sugar absorbed by the activated carbon during clarification. The results are shown in Table 4.

TABLE 4

| Description | Glucose (g/L) | Xylose (g/L) | Acetic Acid (g/L) |
|---|---|---|---|
| Hardwood before activated carbon treatment | 509 | 66 | 6.9 |
| Hardwood after activated carbon treatment | 451 | 56 | 3.6 |

Example 3

The combination of activated carbon and diatomaceous earth for clarification of cellulosic samples has never been shown to work at sugar concentrations at or above 12% total sugars. In one embodiment, the process was modified to improve clarification and successfully refine sugars at concentrations of 20, 30, 40% or higher. The clarification of sugars at higher (industrial) concentrations gives greater advantages for downstream processing, obviating the need for further evaporation.

The pH of a 28% sugar solution derived from corn stover was adjusted from 4.8 to 1.7 using concentrated sulfuric acid. Following the pH adjustment, the stover solution was subdivided and diluted to various concentrations ranging from 10% total sugars to 25% total sugars. These sugar solutions were preheated using a Kuhner shaker set at 65° C. which rotated at 100 rpm for 1 hour. Each sugar concentration sample was then subjected to different levels of activated carbon (2%, 3%, 5%, 10% wt/vol of liquid hydrolysate). Each sample was also subjected to 1.25% diatomaceous earth to increase settling velocity and ease separation of activated carbon from the mother liquor. The solutions were allowed to agitate for 2 hours at 65° C. Following agitation, each sample was centrifuged and filtered through a 0.22 micron filter. An HPLC analysis of the samples was performed and the optical density of each clarified solution also recorded to gauge the amount of color removed by carbon.

Figure 6:
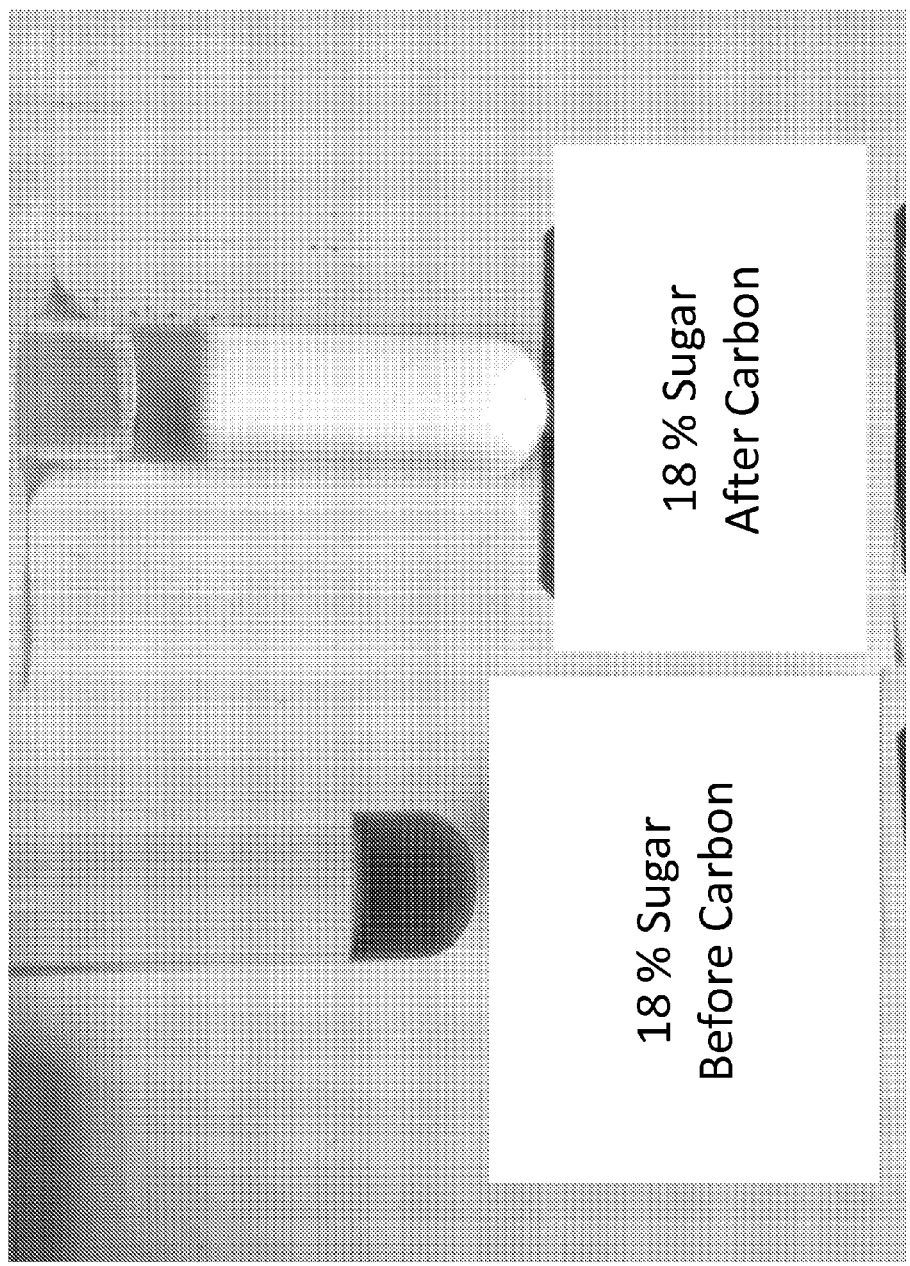
FIG. 6 is a picture of an 18% sugar stream before and after carbon refinement.
Figure 7:
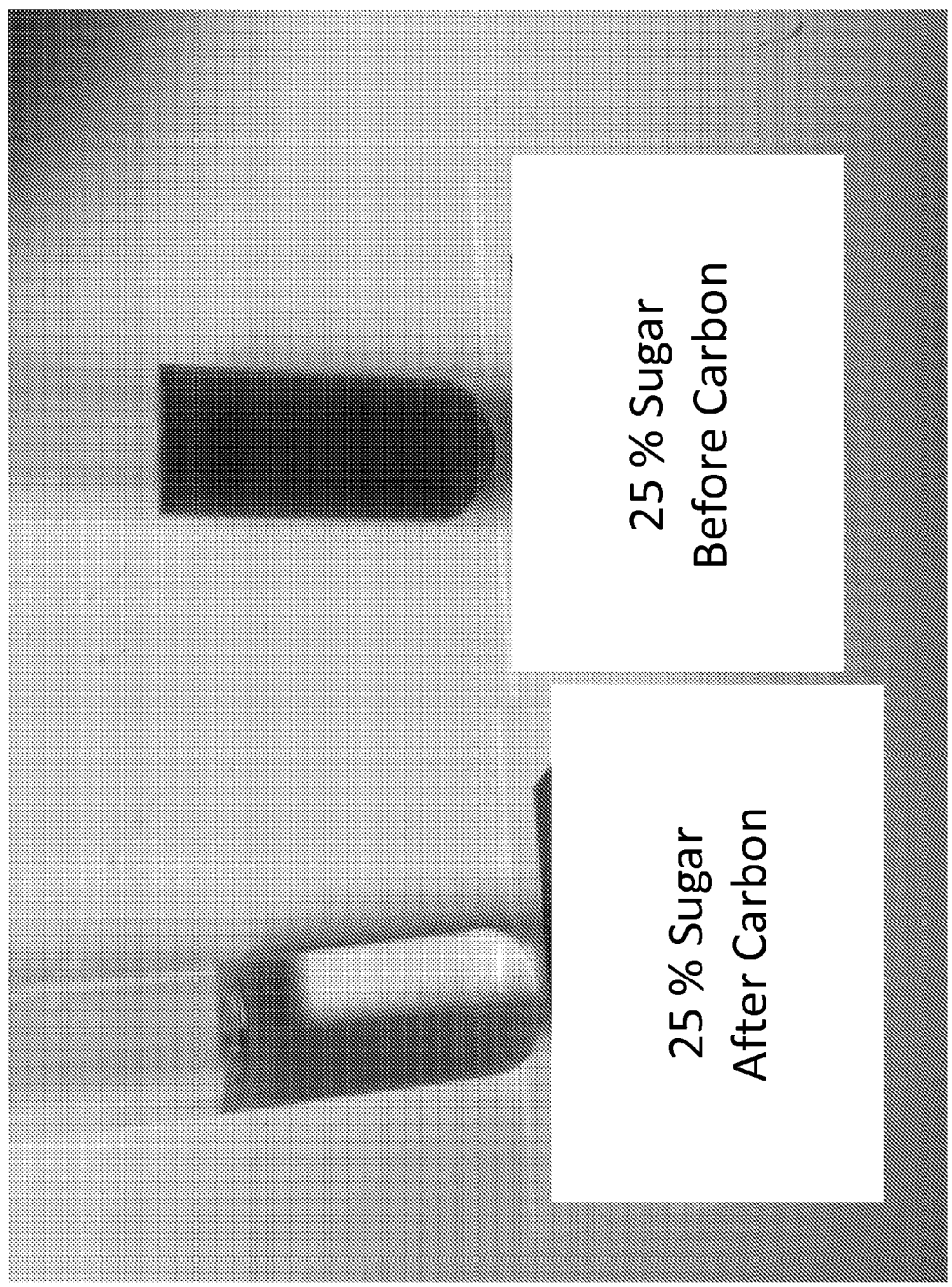
FIG. 7 is a picture of a 25% sugar stream before and after carbon refinement.

Table 5 shows the optical density (OD) of each sugar solution before and after treatment with activated carbon using distilled water as a baseline. FIG. 6 shows the difference of an 18% sugar solution before (left) and after (right) treatment with 10% activated carbon. The sample treated with carbon cannot be distinguished from water by the naked eye. FIG. 7 is an example of a 25% sugar solution before (right) and after (left) treatment with 10% activated carbon.

TABLE 5

| Description (Samples prior to carbon addition) | OD ($H_2O$ Baseline) % trans |
|---|---|
| 10% sugar | 39.2 |
| 13.4% sugar | 36.8 |
| 17.9% sugar | 30.8 |
| 24.9% sugar | 13.2 |

| Description (Samples post carbon addition) | OD ($H_2O$ baseline) % trans | Transparency Improvement (%) |
|---|---|---|
| 10% total sugar; 5% Activated Carbon | 95.2 | 56 |
| 10% Sugar; 10% AC | 99.6 | 60.4 |
| 13.4% Sugar; 2% AC | 80.8 | 44 |

TABLE 5-continued

| | | |
|---|---|---|
| 13.4% Sugar; 3% AC | 86 | 49.2 |
| 13.4% Sugar; 5% AC | 93.8 | 57 |
| 13.4% Sugar; 10% AC | 99.2 | 62.4 |
| 17.9% Sugar; 2% AC | 70.4 | 39.6 |
| 17.9% Sugar; 3% AC | 75.8 | 45 |
| 17.9% Sugar; 5% AC | 84.4 | 53.6 |
| 17.9% Sugar; 10% AC | 98 | 67.2 |
| 24.9% Sugar; 2% AC | 42.2 | 29 |
| 24.9% Sugar; 3% AC | 45.2 | 32 |
| 24.9% Sugar; 5% AC | 59.2 | 46 |
| 24.9% Sugar; 10% AC | 85.2 | 72 |

Previous data showed no reduction in color when sugar solutions were concentrated above 15% total sugars. This data shows significant reduction above 20% sugars simply by adjusting the pH, thus indicating the important role of pH in clarification.

Example 4

A 16% sugar solution (C5+C6 sugar) was derived from corn stover and pretreated through standard processing and enzyme hydrolysis conditions. HMF, acetic acid and furfural were added to the solution to inflate the inhibitor level and determine if activated carbon would remove a significant portion of the inhibitors. A sample of the solution was taken for HPLC analysis. The solution was divided into two samples. The first sample served as the control (no carbon treatment), the second was treated with activated carbon to determine if it could extract the inhibitors.

The activated carbon was heated to 200° C. in an oven for 4 hours and a portion added to the second sample. Both samples were allowed to agitate for 12 hours at 125 rpm and 50° C. The samples were then filtered and analyzed via HPLC.

Figure 8:
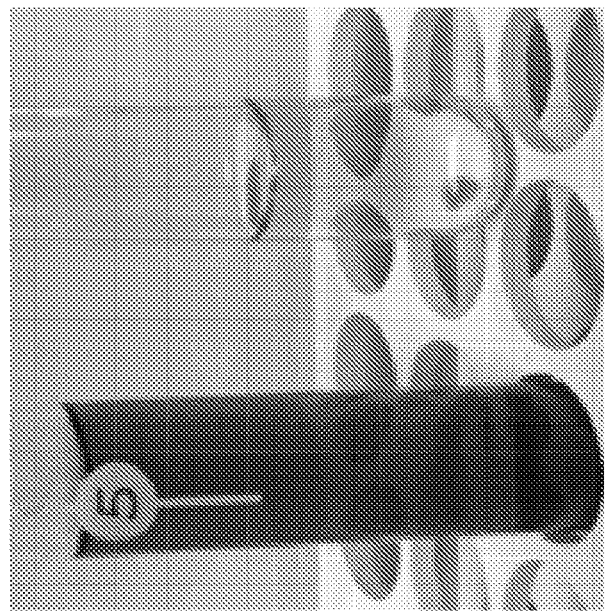
FIGS. 8A and 8B show a 16% and a 12% sugar stream, respectively, before and after activated carbon treatment.
Figure 8:
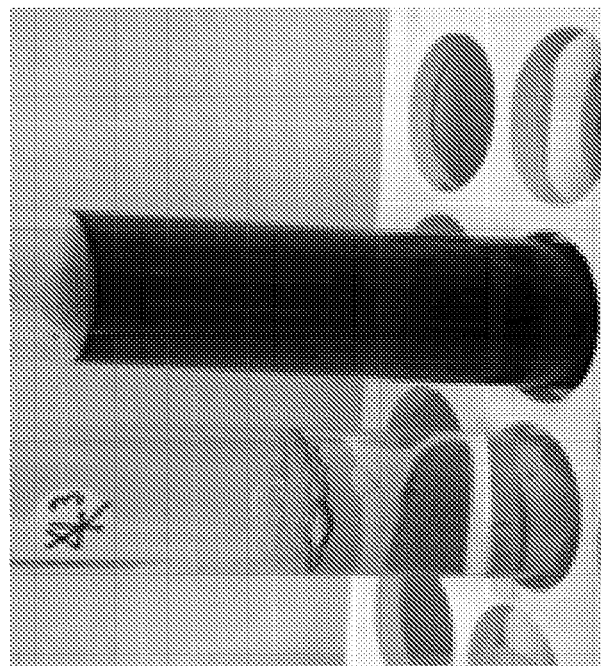

FIGS. 8A and 8B show pictures of sugar stream samples treated with activated carbon under the conditions described above. In FIG. 8A, the untreated 16% stream is shown in the tube on the right and the treated sample on the left. In FIG. 8B, an untreated 12% stream is shown in the tube on the left and the treated sample on the right. In addition the level of phenolics or aromatics in the 16% broth were analyzed using UV at 205 and 289 nM. Due to lignin heterogeneity, the control sample was analyzed by UV analysis and the % reduction the peak area were determined and correlated to reduction in aromatic lignin. The percentage reduction of the phenolic peaks from the UV spectra are as follows:

A 55% reduction at 7.3 min retention peak

A 31% reduction at 29.1 min retention peak

A 44% reduction at 39.1 min. retention peak

Figure 9:
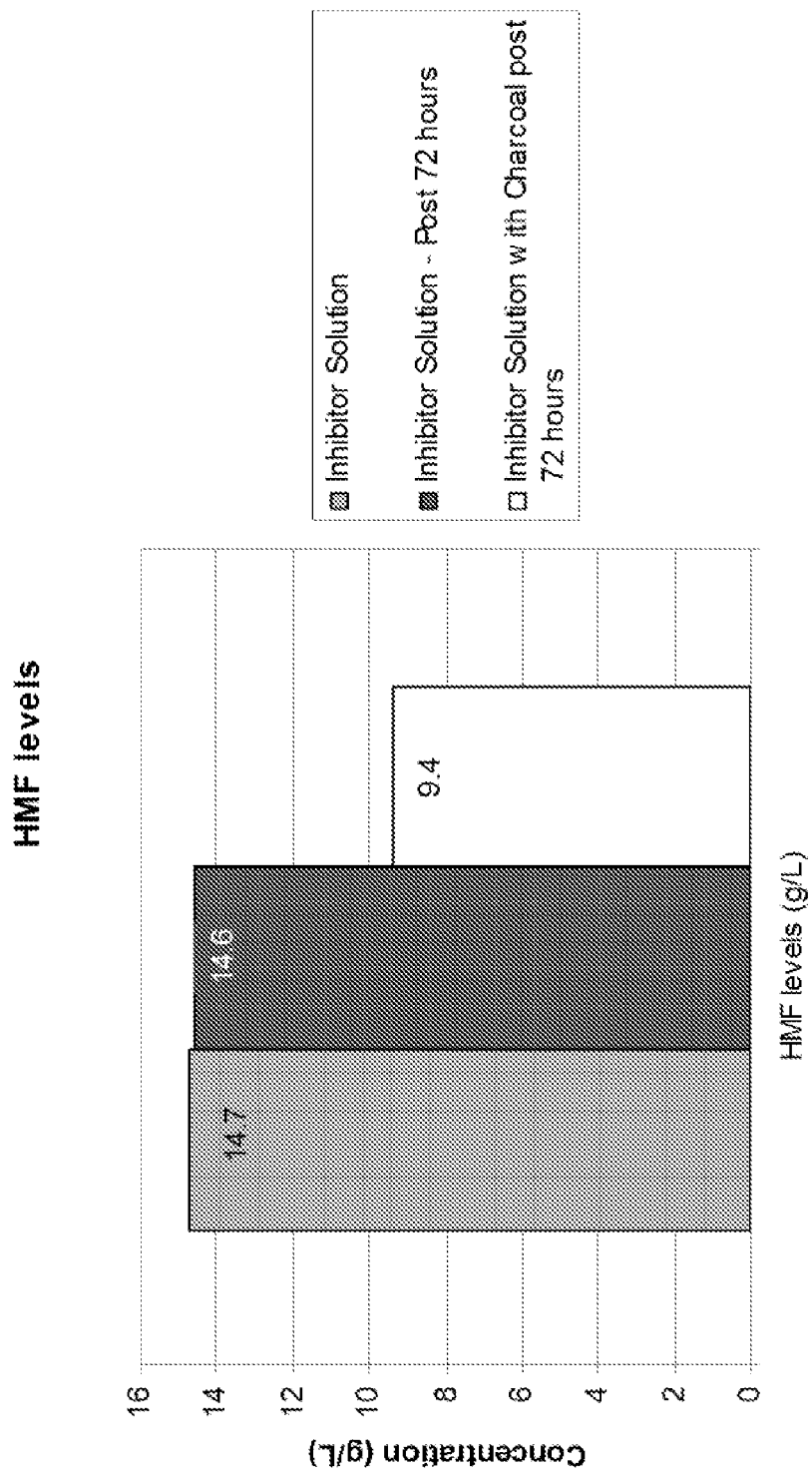
FIG. 9 is a graph comparing the results of carbon filtration efficiency in removing HMF.
Figure 10:
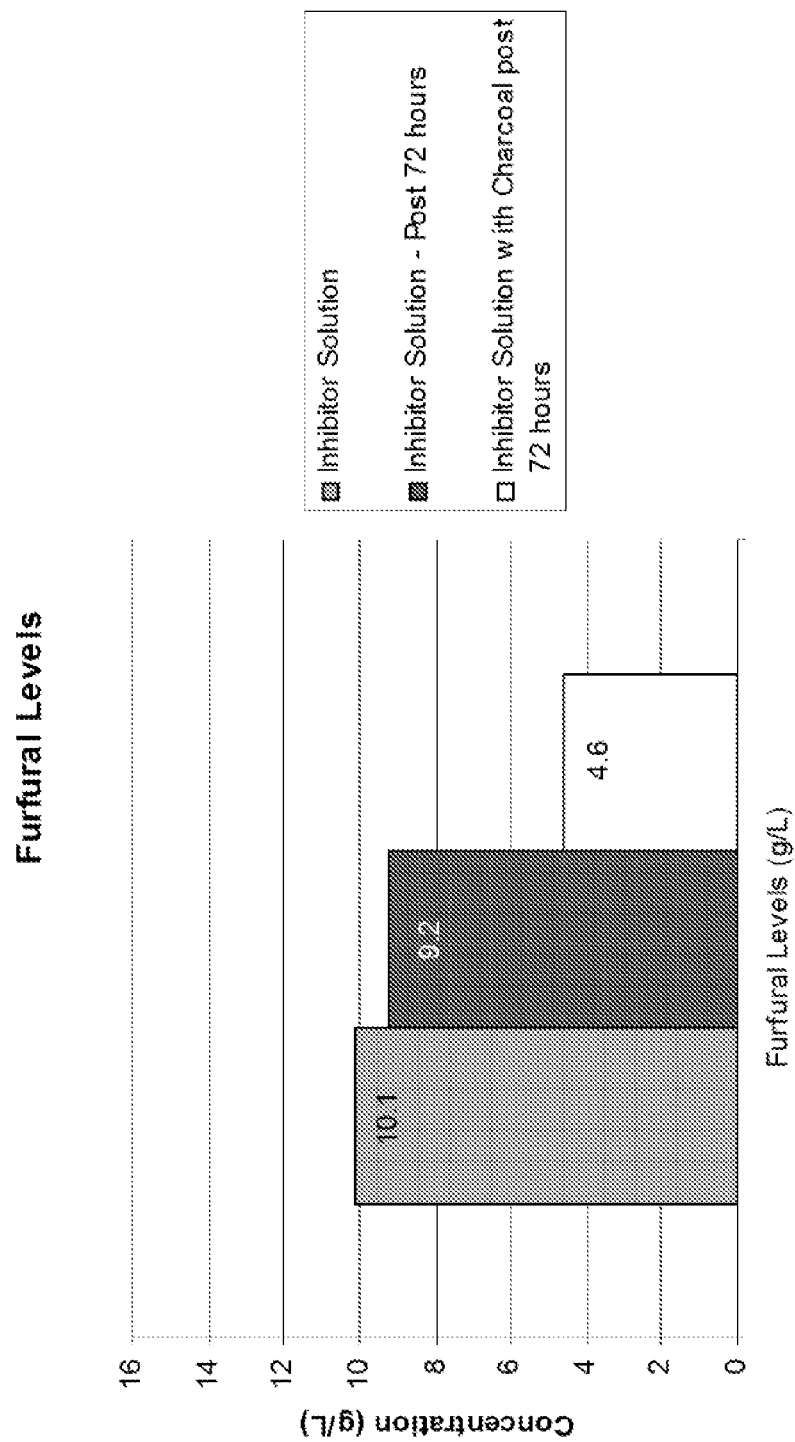
FIG. 10 is a graph comparing the results of carbon filtration efficiency in removing furfural.
Figure 11:
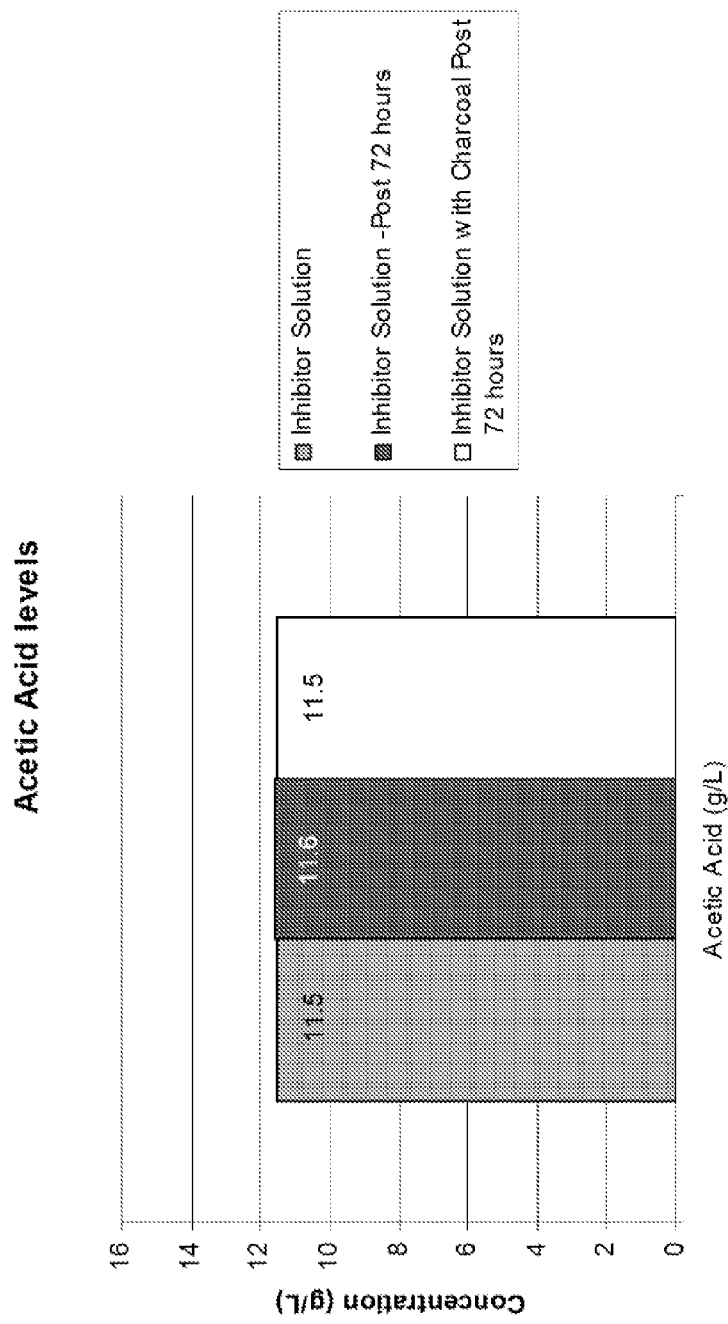
FIG. 11 is a graph comparing the results of carbon filtration efficiency in removing acetic acid.

FIGS. 9-11 show how each of the inhibitor levels were altered by the presence of activated carbon. Not only is there a significant color reduction from the use of activated carbon, there is also a reduction in both HMF and Furfural. The HMF levels from the use of activated carbon were reduced from 14.6 g/L to 9.4 g/L which is a 38% reduction (FIG. 9). The furfural levels were reduced from 10.1 g/L to 4.6 g/L which is a 55% reduction (FIG. 10). There was little or no reduction in acetic acid levels (FIG. 11) or in the levels of sugars in the broth.

Two samples of treated (refined) and untreated (crude) were analyzed for trace metal differences. These samples consisted of 20% C6 rich sugars prepared from pretreated wheat straw. The results are presented in Table 6 below.

TABLE 6

| Trace Metal Profile | C6 rich Wheat Straw - Refined (ppm) | C6 rich Wheat Straw - Crude (ppm) |
|---|---|---|
| Aluminum | 18 | <3.3 |
| Antimony | <0.033 | <0.33 |
| Arsenic | 0.33 | <0.17 |
| Barium | 0.37 | 0.21 |
| Cadmium | <0.033 | <0.33 |
| Calcium | <0.0033 | 0.037 |
| Chromium | 160 | 44 |
| Cobalt | 0.35 | 0.70 |
| Copper | 0.058 | <0.050 |
| Iron | 0.27 | <0.17 |
| Lead | 12 | 1.1 |
| Magnesium | <0.012 | <0.12 |
| Manganese | 38 | 12 |
| Nickel | 2.7 | 0.2 |
| Phosphorus | 0.24 | 0.17 |
| Potassium | 99 | 91 |
| Selenium | 0.36 | <0.50 |
| Silver | <0.017 | <0.17 |
| Sodium | 210 | 120 |
| Sulfur | 1200 | 280 |
| Tin | 0.094 | <0.33 |
| Vanadium | 0.12 | <0.13 |
| Zinc | 0.33 | <0.33 |

The refined stream includes several elements showing a higher concentration than the crude stream. There is a significant increase in sulfur due to the pH drop to 2.0 during the refinement process. There are also increases found in Sodium, Potassium, Nickel, Manganese, Lead, Chromium and Aluminum. This is likely the result of elements in the diatomaceous earth filter used to re-capture the carbon from the solution.

Example 5

This example illustrates a procedure for clarification and de-colorization of a sugar stream using heated powdered activated carbon (PAC). The sugar stream is produced by the pretreatment and hydrolyzation of biomass comprising cellulose, hemicellulose, and/or lignocellulose. If necessary, the sugar stream is concentrated to greater than about 15% sugars w/v before clarification and de-colorization.

Powdered activated carbon (Sigma Aldrich C9157 cell culture grade) having a 5-10 micron particle size is heated to 200° C. for from 4 hours to 24 hours. The sugar stream is adjusted to a pH of about 2 using sulfuric acid and heated to about 65° C. While still hot, the heated PAC is added to the sugar stream at about 10% w/v and mixed thoroughly. The mixture is maintained at about 65° C. for from 1 to 2 hours with continuous mixing.

Diatomaceous earth is added to the PAC/sugar mixture to about 1% w/v and the mixture is centrifuged to facilitate carbon removal. The centrifuged mixture is then subjected to back end filtration using diatomaceous earth (Pure D brand) that is formed into a cake in a buchner funnel.

Figure 12:
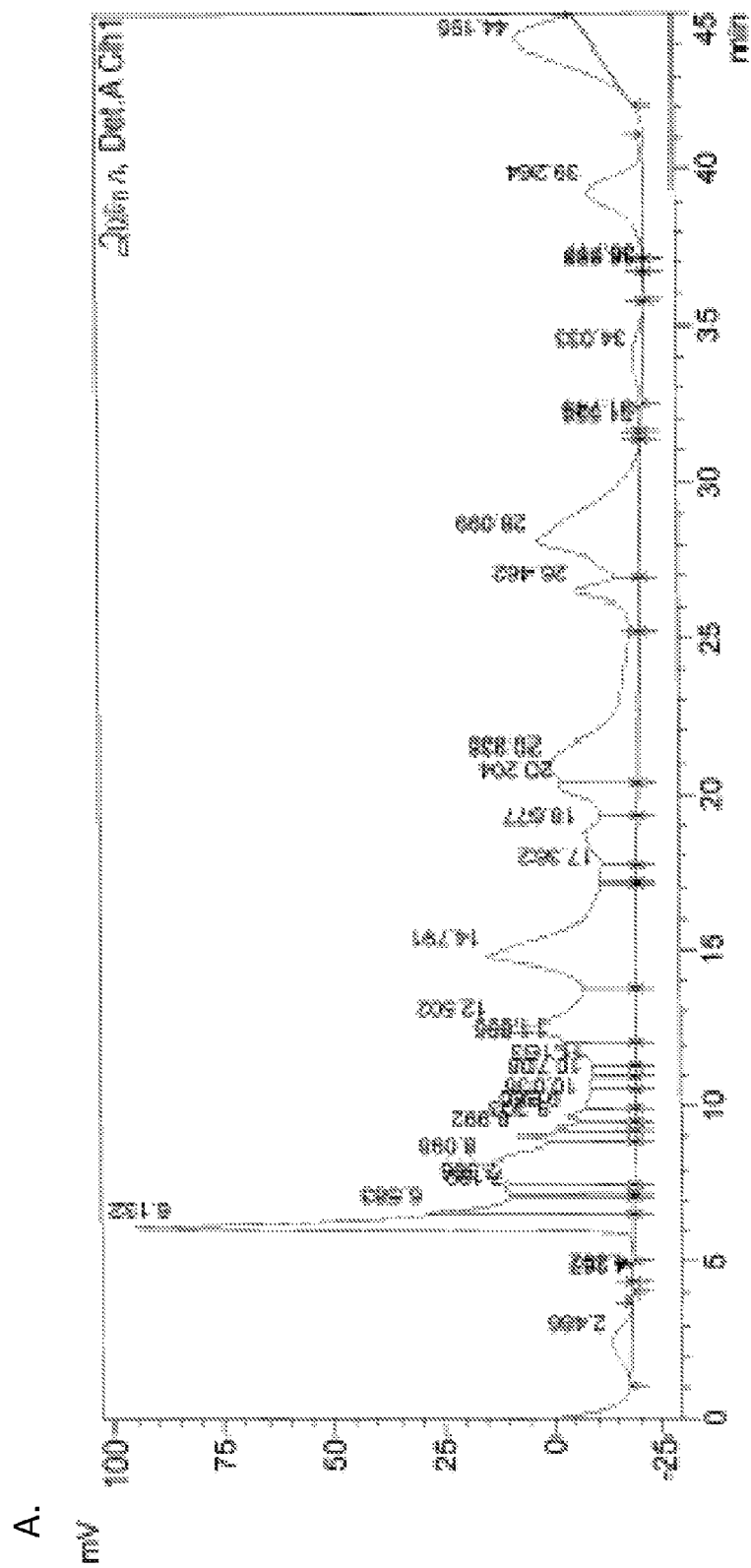
FIGS. 12A and 12B show the UV-detector peaks of a control (12A), and PAC-treated sugar hydrolysates (12B).
Figure 12:
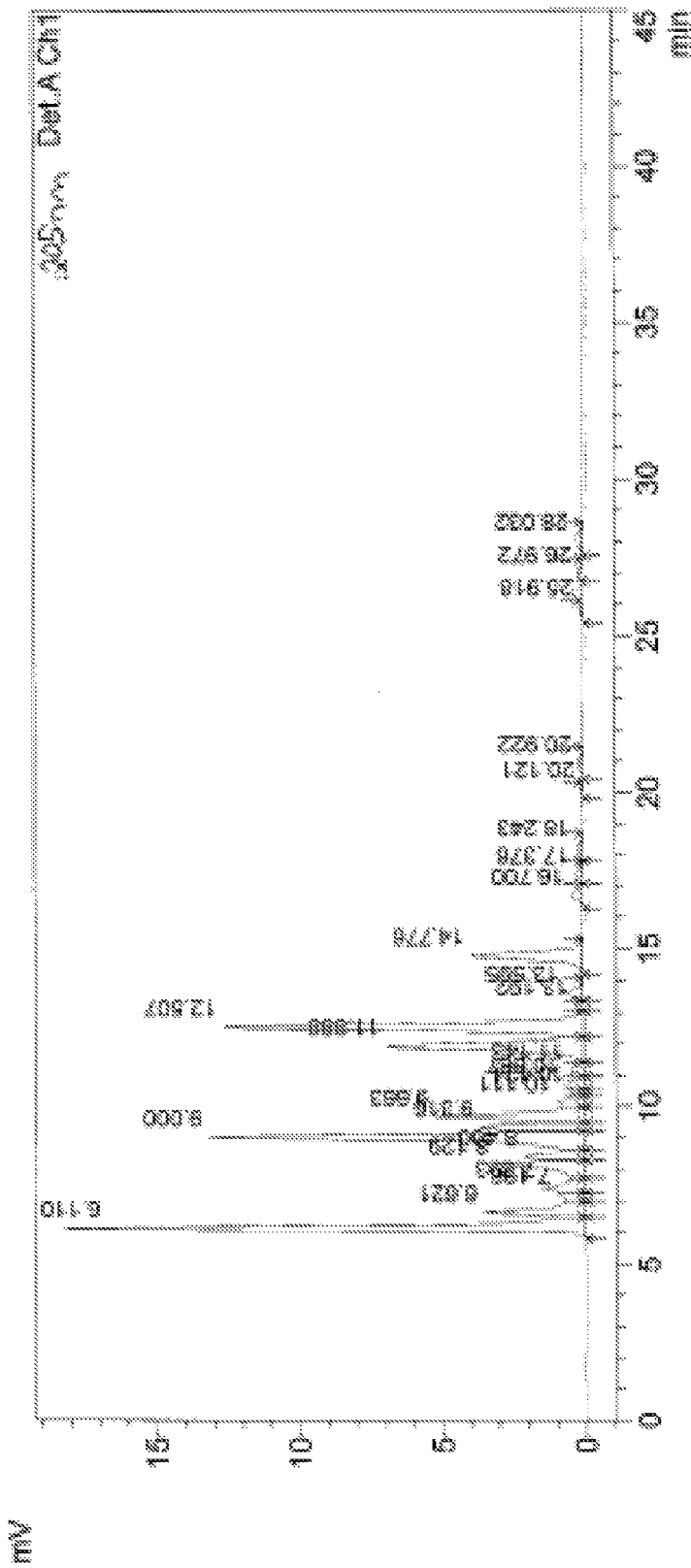

FIG. 12 illustrates the UV-detector peaks of a control (A), and carbon filtered sugar streams, respectively. The sugar stream was produced by pretreatment and hydrolysis of corn stover and was at a concentration of about 40% sugar. The UV-spectra were measured at 205 nm. The reduction in total peak area indicates that levels of phenolics and aromatics were reduced by 95.6%.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of refining a sugar stream, the method comprising:
    (a) acidifying the sugar stream to a pH of from about 1 to about 4 by adding an acid to produce an acidified sugar stream;
    (b) heating activated carbon to a temperature of from about 100°C. to about 300°C. to produce heat activated carbon; and
    (c) contacting the acidified sugar stream with the heat activated carbon for a sufficient time to produce a refined sugar stream.

2. The method of claim 1, wherein the heat activated carbon is at a higher temperature than the acidified sugar stream during the contacting.

3. The method of claim 1, further comprising pretreating or hydrolyzing a biomass comprising cellulosic, hemicellulosic, or lignocellulosic material to produce the sugar stream.

4. The method of claim 1, wherein the refined sugar stream comprises at least about 30% less of one or more inhibitors than the sugar stream.

5. The method of claim 4, wherein the one or more inhibitors comprise hydroxymethylfurfural, furfural, or a combination thereof.

6. The method of claim 1, wherein the refined sugar stream has a transparency that is at least about 20% higher than the sugar stream when measured at 600 nm.

7. The method of claim 1, wherein the refined sugar stream comprises at least about 30% less phenolic and aromatic compounds than the sugar stream when measured at 205 nm or 289 nm.

8. The method of claim 1, wherein the sugar stream comprises at least about 15% w/v of one or more sugars.

9. The method of claim 1, wherein the heat activated carbon is at from 2% to about 10% w/v in the sugar stream during the contacting.

10. The method of claim 1, further comprising removing the heat activated carbon from the refined sugar stream.

11. The method of claim 10, wherein removing the heat activated carbon from the refined sugar stream comprises adding diatomaceous earth to the sugar stream.

12. A method of refining a sugar stream, the method comprising:
    (a) heating activated carbon to a temperature of from about 100° C. to about 300° C. to produce heat activated carbon;
    (b) contacting the sugar stream with the heat activated carbon for a sufficient time to produce a refined sugar stream, wherein the heat activated carbon is at a temperature greater than the sugar stream.

13. The method of claim 12, wherein the heat activated carbon is at from 2% to about 10% w/v in the sugar stream during the contacting.

14. The method of claim 12, wherein the refined sugar stream comprises at least about 30% less of one or more inhibitors than the sugar stream.

15. The method of claim 14, wherein the one or more inhibitors comprise hydroxymethylfurfural, furfural, or a combination thereof.

16. The method of claim 12, wherein the refined sugar stream has a transparency that is at least about 20% higher than the sugar stream when measured at 600 nm.

17. The method of claim 12, wherein the refined sugar stream comprises at least about 70% less phenolic and aromatic compounds than the sugar stream when measured at 205 nm or 289 nm.

18. The method of claim 12, wherein the heat activated carbon is at from 2% to about 10% w/v in the sugar stream during the contacting.

* * * * *